United States Patent [19]

Hayano et al.

[11] Patent Number: 5,578,466
[45] Date of Patent: Nov. 26, 1996

[54] RECOMBINANT CO-EXPRESSION SYSTEM OF PROTEIN DISULFIDE ISOMERASE GENE, YEAST RECEPTOR PROTEIN ERD2 GENE AND A FOREIGN PRODUCT POLYPEPTIDE GENE, AND A PROCESS FOR PRODUCING THE FOREIGN POLYPEPTIDE USING SUCH SYSTEM

[75] Inventors: Toshiya Hayano; Setsuko Katoh; Nobuhiro Takahashi; Masanori Suzuki; Keiichi Honma, all of Iruma-gun, Japan

[73] Assignee: Tonen Corporation, Tokyo, Japan

[21] Appl. No.: 872,673

[22] Filed: Apr. 17, 1992

[30] Foreign Application Priority Data

Apr. 18, 1991 [JP] Japan .................................. 3-114074
Oct. 30, 1991 [JP] Japan .................................. 3-311601

[51] Int. Cl.$^6$ ......................... C12N 1/19; C12N 15/14; C12N 15/62
[52] U.S. Cl. ................ 435/69.7; 435/69.1; 435/69.6; 435/254.2
[58] Field of Search ............... 435/69.1, 254.2, 435/69.6, 69.7; 536/23.5, 23.2, 23.4

[56] References Cited

FOREIGN PATENT DOCUMENTS

| 0293793 | 12/1988 | European Pat. Off. . |
|---|---|---|
| 0319641 | 6/1989 | European Pat. Off. . |
| WO89/07140 | 8/1989 | WIPO . |

OTHER PUBLICATIONS

Gatenby, A. A., et al. (1990) Trends Biotechnol. 8:354–58.
Buchner, J., et al. (1991) Curr. Opinion Biotechnol. 2:532–38.
Hlodan, R., et al. (1991) Biotechnol. Gen. Engr. Rev. 9:47–88.
Semenza, J. C., Hardwick, K. G., Dean, N. and Pelham, H. R. B. (1990) Cell 61, 1349–1357.
Lewis, M. J. and Pelham, H. R. B. (1990) Nature 348, 162–163.
Edman, J. C. et al., Nature 317, 267–270, 1985.
Pihlajaniemi, T. et al. (1987) The EMBO J. 6, 643–649.
Schein, C. H., Bio/Technology 7, 1141–1148, 1989.
Freedman, R. B., Cell 57, 1069–1072, 1989.
J. Semenza et al., *Cell*, 61:1349–1357 (1990).
K. Yamauchi et al., *Biocheical and Biophysical Research Communications*, 146(3):1485–1492 (1987).
Murano, S. and Pelham, H. R. B. (1987) Cell 48, 899–907.
Pelham, H. R. B., Hardwick, K. G. and Lewis, M. J. (1988) The EMBO Journal 7, 1757–1762.
Pelham, H. R. B. (1990) TIBS 15, 483–486.

*Primary Examiner*—Garnette D. Draper
*Assistant Examiner*—David L. Fitzgerald
*Attorney, Agent, or Firm*—David G. Conlin; Peter F. Corless

[57] ABSTRACT

The present invention is directed to a transformant comprising the following expression units in a co-expressible state:

an expression unit containing a gene coding for a receptor protein ERD2 from yeast or analog thereof which is capable of binding to a protein localizing in endoplasmic reticulum and having a signal for staying therein;

an expression unit containing a gene coding for said protein localizing in endoplasmic reticulum; and an expression unit containing a foreign gene coding for a polypeptide which is a subject of function of said protein localizing in endoplasmic reticulum, and to a transformant comprising, in a co-expressible state, a fusion gene which is composed of a DNA fragment coding for a human serum albumin prepro-sequence and a foreign gene coding for a useful polypeptide. The present invention is also directed to a process for producing said polypeptide by co-expressing said genes in said transformant such that the polypeptide is predominantly secreted out of the transformant cell. Consequently, the invention has an advantage of improving the productivity of said polypeptide.

15 Claims, 15 Drawing Sheets

Fig. 2

```
                                HSA PREPRO-        PDI
                                SEQUENCE
···ATG AAG TGG GTT ACC TTC ATC TCT TTG TTG TTC TTG TTC TCT TCT GCT TAC TCT AGA AGG GGC GCC CCC GAG GAG GAC CAC···
···Met Lys Trp Val Thr Phe Ile Ser Leu Leu Phe Leu Phe Ser Ser Ala Tyr Ser Arg Arg Gly Ala Pro Glu Glu Asp His···
```

94,000 —

67,000 —  ← PDI 43,000 —

30,000 —

20,000 —

14,000 —
M 69 70 71 72 73 74 75 76

1: pAH/HIS23
2: pAHhPDIyI/HIS23

1, 3, 5, 7, 9 : pAH/HIS23
2, 4, 6, 8, 10: pAHhPDILy1/HIS23
11: HSA STANDARD 0.25ug
12: HSA STANDARD 0.5ug 1, 3, 5, 7, 9: pAH/HIS23
2, 4, 6, 8, 10: pAHhPDILy1/HIS23

RECOMBINANT CO-EXPRESSION SYSTEM OF PROTEIN DISULFIDE ISOMERASE GENE, YEAST RECEPTOR PROTEIN ERD2 GENE AND A FOREIGN PRODUCT POLYPEPTIDE GENE, AND A PROCESS FOR PRODUCING THE FOREIGN POLYPEPTIDE USING SUCH SYSTEM

BACKGROUND OF THE INVENTION

1. Field of the Invention

This invention relates to a co-expression system which comprises a gene coding for protein disulfide isomerase (PDI), a gene coding for an yeast receptor protein ERD2 or analog thereof and a foreign gene coding for a useful polypeptide and to a process for the production of said polypeptide using said system. PDI is an enzyme which enhances formation of the higher-order structure of polypeptides through its function of catalyzing the exchange reaction of a disulfide bond(s) in the polypeptides.

2. Prior Art

Studies on the in vitro refolding of denatured proteins have revealed the presence of both isomerization reactions of a disulfide bond and of a proline peptide as factors for determining a folding rate of polypeptides (Freedman, *Cell*, vol.57, pp.1069–1072, 1989; Fisher and Schmid, *Biochemistry*, vol.29, pp.2205–2212, 1990). As enzymes which catalyze these slow reactions during the polypeptide folding, peptidyl prolyl cis-trans isomerase (PPI) has been found in the latter case, and protein disulfide isomerase (PDI) and thioredoxin in the former case. According to in vitro experiments, these enzymes accelerate a refolding rate of denatured proteins, thus indicating a possibility of applying them to the in vitro refolding of inactive proteins produced by genetic engineering techniques (Schein, *Bio/Technology*, vol.7, pp.1141–1148, 1989; J. Udaka, *Nippon Nogei Kagaku Kaishi*, vol. 64, pp. 1035–1038, 1990).

Since PDI is soluble in water and can be isolated relatively easily from the liver of mammals, its properties as a catalyst have been studied in detail. PDI catalyzes the exchange reaction between thiol/disulfide bonds and is capable of undergoing formation, isomerization or reduction of the disulfide bond in protein substrates (Freedman, *Cell*, vol.57, pp.1069–1072, 1989). It is known that, in vitro, PDI enhances the formation or exchange reaction of a disulfide linkage(s) in molecules of a single domain protein such as RNase and of a multiple domain protein such as serum albumin, or enhances the formation of an intermolecular disulfide bond(s) in a protein having a subunit structure such as immunoglobulin, procollagen or the like (Freedman, *Nature*, vol.329, p. 196, 1987).

PDI from Mammals exists usually as a homodimer of the polypeptide having a molecular weight of about 57,000 and shows a highly acidic pI value (4.2 to 4.3).

The PDI gene from rat liver has been isolated. The amino acid sequence deduced from the DNA sequence of the PDI gene indicated that PDI has an intramolecular duplicate structure consisting of two homologous units. One of these two homologous units has a homology to the amino acid sequence of thioredoxin, indicating that its active site has an amino acid sequence similar to that of thioredoxin (Edman et al., *Nature*, vol.317, pp.267–270, 1985). Thioredoxin enhances the reduction of a disulfide bond in insulin and the exchange reaction of a disulfide bond in RNase in vivo, which indicate that thioredoxin plays a similar role to PDI in the in vivo folding process of proteins (Pigict and Schuster, *Proc. Natl. Acad. Sci.*, U.S.A., vol.83, pp.7643–7647, 1986).

Although the amount of PDI present in a mammalian living body differs depending on the type of tissues and the differentiation stage of cells, such a difference is probably attributed to the existence of certain secretory proteins. In addition, PDI is localized abundantly in the endoplasmic reticulum through which a protein destined for secretion is known to pass. On the basis of these facts, it is assumed that PDI catalyzes or accelerates the formation of a disulfide bond(s) in secretory proteins newly synthesized within cells. Such an assumption is supported by the results of a study on the biosynthesis of γ-gliadin in a cell-free protein synthesis system, that the formation of a disulfide bond in conjunction with the translation of γ-gliadin hardly occurs when an endoplasmic reticulum fraction from which PDI was washed out in advance is used, while the disulfide bond formation is restored by the addition of PDI (Bulleid and Freedman, *Nature*, vol.335, pp.649–651, 1988).

In addition to the disulfide bond formation, PDI functions in other post-translational modifications of proteins. For example, the multifunctional property of PDI in connection with the protein modifications has been suggested on the basis of its homology to a catalytic unit, β-subunit, of prolyl-4-hydroxylase which catalyzes hydroxylation of proline residues in collagen, to a glycosylation site binding protein that recognizes a signal sequence Asn-X-Ser/Thr of a peptide to which a sugar chain is bound during N-glycosylation process of synthetic protein (Pihlajaniemi et al., *EMBO J.*, vol.6, pp.643–649, 1987; Geetha-Habib et al., *Cell*, vol.54, pp.1053–1060, 1988), to a thyroid hormone binding protein (triiodo-L-thyronine binding protein; Cheng et al., *J. Biol. Chem.*, vol.262, pp.11221–11227, 1987), etc. In addition to these facts, some molecular species having partly homologous amino acid sequences to PDI have been found though they are different from the PDI. For example, certain gonadotropic hormones such as follitropin and lutropin contain amino acid sequences homologous to an amino acid sequence which is regarded as an active site of PDI, and these hormones catalyze the isomerization of a disulfide bond (Boniface et al., *Science*, vol.247, pp.61–64, 1990). Also, phospholipase C, an enzyme which hydrolyzes phosphatidylinositol-4,5-bisphosphate into 1,2-diacyl glycerol and inositol-1,4,5-triphosphate, has a domain homologous to PDI in its molecule (Bennett et al., *Nature*, vol.334, pp.268–270, 1988). In consequence, PDI and PDI-like molecules seem to have many functions in a markedly wide range of vital phenomena, both intracellularly and extracellularly.

Although the PDI has extensive functions as described above, a main effect of PDI is to form a protein (or a protein complex) having a natural higher-order structure by catalyzing the isomerization of an intramolecular or intermolecular disulfide bond(s). In many cases, however, an almost stoichiometric amount of PDI is required to attain an optimum reaction rate. It is expected therefore that an intramolecular or intermolecular isomerization rate of a disulfide bond will be slow when a disulfide isomerase has a low activity, and such a slow reaction rate will entail a low formation efficiency of a protein having a suitable disulfide bond(s). It is thought that such a low disulfide isomerase activity is one causes of the formation of insoluble molecular aggregates of various eukaryote-originated proteins (especially secretory proteins) in *Escherichia coli*. Although *E. coli* contains thioredoxin which is superior to PDI in terms of the activity as a disulfide reductase, the isomerase activity of thioredoxin is low. On the contrary, since an intramolecular disulfide bond(s) can often be found in secretory proteins, it is thought that a disulfide bond activity resulted from disulfide isomerization is high in cells or tissues which have a high secretion ability. This was indicated strongly by a comparative study on the relative PDI mRNA contents in various rat tissues, in which the contents in organs were found to be liver>pancreas, kidney>lung>spermary, spleen>heart>brain in order (Edman et al., Nature, vol.314, pp.267–270, 1985).

Since polypeptides are synthesized in the cytoplasm which has reducing environment in the cells, a disulfide bond which is necessary for the proper folding of a polypeptide will not be formed efficiently in the reducing condition. Such a condition is generated for example in prokaryotic cells which have no compartments. Taking this into consideration, prokaryotic cells and eukaryotic cells may be different from each other in terms of factors concerning the formation of a disulfide bond and of conditions which enable its formation. When useful proteins (most of them are secretory proteins) are produced by recombinant DNA techniques, it is necessary to form a disulfide bond under certain conditions which are suitable for each protein to be produced. To accomplish such conditions, a host cell should have a suitable compartment and a large amount of a disulfide-forming enzyme (i.e., disulfide isomerase) which is localized in the compartment.

In eukaryotes, secretory proteins are transported outside the cell through the endoplasmic reticulum, Golgi body and secretory granules, and such a secretion process is regarded as a passive flow which is called "bulk flow". On the other hand, proteins localizing in the cavity of endoplasmic reticulum were initially thought to stay therein via such a process that the corresponding proteins synthesized were incorporated into the endoplasmic reticulum in the similar manner to the secretory protein and then transferred along the "bulk flow", but sent back again from Golgi body to the endoplasmic reticulum by a certain mechanism. Thereafter, primary structures of various proteins localizing in the mammalian endoplasmic reticulum have been determined. From some of these proteins, such as a protein disulfide isomerase (PDI), a glucose-regulated protein 78 (grp78, the same as Bip which is an immunoglobulin heavy chain binding protein) and a glucose-regulated protein 94 (grp94), a common C-terminal sequence "KDEL" ("HDEL" in the case of yeast) consisting of 4 amino acid residues was found. In addition, it was suggested that, in yeast cells, this sequence acts as a signal for allowing proteins to localize in the endoplasmic reticulum, because a mutant protein of Grp78 lacking in KDEL sequence is secreted extracellularly and because lysozyme, in spite of its secretory nature, can stay in the endoplasmic reticulum when the "HDEL" sequence is bound to its C-terminus (Munro, S. and Pelham, H. R. B., Cell, vol.48, p.899, 1987; Pelham, H. R. B., Hardwick, K. G. and Lewis, M. J., EMBO J., vol.7, p.1757, 1988). In consequence, it was considered that an endoplasmic reticulum or Golgi body contains receptor molecules specific for the "KDEL" or "HDEL" sequence, and that the receptor controls localization of a protein having such a sequence on its C-terminus.

Thereafter, a receptor for the signal "HDEL" was identified in yeast by the analysis of a yeast mutant erd2 in which a protein having "HDEL" sequence does not stay in the endoplasmic reticulum but transfers along its secretion process, and the receptor for the signal KDEL was also identified in mammals by the analysis in which anti-idiotype antibodies specific for "KDEL" sequence were used (Semenza, J. C., Hardwick, K. G., Dean, N. and Pelham, H. R. B., Cell, vol. 61, p. 1349, 1990; Vaux, D., Tooze, J. and Fuller, S., Nature, vol.345, p.495, 1990). Gene structure of the yeast "HDEL" receptor has been revealed from which its primary amino acid sequence was deduced, with an estimated molecular weight of 26 kd. On the other hand, the mammalian "KDEL" receptor identified by the use of anti-idiotype antibodies has been reported to have a molecular weight of 72 kd, thus indicating that the mammalian receptor is probably different from the above yeast receptor. Thereafter, a gene coding for a protein homologous to the yeast "HDEL" receptor has been cloned in mammals by cross-hybridization (Lewis, M. J. and Pelham, H. R. B., Nature, vol.348, p.162, 1990). However, it is not clear whether the two different signal receptors function with mutual relationship or independently in mammals.

In addition to the "KDEL" and "HDEL" sequences, other homologous sequences such as "DDEL", "ADEL", "SDEL", "RDEL", "KEEL", "QEDL", "HIEL", "HTEL" and "KQDL" are known as signals for staying in endoplasmic reticulum, and polypeptides having these sequences are considered to stay in endoplasmic reticulum by associating with the aforementioned receptor molecules (Pelham, H. R. B., TIBS, vol.15, p.483, 1990).

However, nothing is in practice known about an in vivo system in which PDI is contained in a large quantity in a suitable compartment in the coexistence of a useful target protein, the PDI being capable of acting on the protein. Moreover, in spite of the applicability of PDI to the in vitro refolding of denatured proteins and to the improved productivity of secretory proteins in cells, this enzyme has been prepared only by direct purification from the internal organs. In addition, there are no reports on the interspecific expression of PDI, and on the establishment of a process for its production by means of genetic engineering or a process in which the productivity of a useful polypeptide is improved by the combination of the PDI gene with a gene coding for the polypeptide.

SUMMARY OF THE INVENTION

An object of the present invention is to provide a transformant comprising the following expression units integrated on yeast chromosome in a co-expressible state:

- an expression unit containing a gene coding for a receptor protein ERD2 from yeast or analog thereof which is capable of associating with (or binding to) a protein localizing in endoplasmic reticulum and having a signal for staying therein; and
- an expression unit containing a gene coding for said protein localizing in endoplasmic reticulum and having a signal for staying therein.

Preferably, the gene coding for a protein localizing in endoplasmic reticulum and having a signal for staying therein is selected from the group consisting of a human protein disulfide isomerase (PDI) gene and a fusion gene which is composed of a DNA fragment coding for a human serum albumin (HSA) prepro-sequence and the isomerase gene. According to one aspect of the invention, said fusion gene has a base sequence coding for the −24 to +491 amino acid sequence shown in SEQ ID NO:2.

Another object of the present invention is to provide a transformant comprising an expression unit containing a foreign gene coding for a polypeptide which is a subject of function of said protein localizing in endoplasmic reticulum, other than the two expression units described above, the three expression units being integrated on yeast chromosome.

Still another object of the present invention is to provide a fusion gene for use in an expression of PDI, which is composed of a DNA fragment coding for a HSA prepro-sequence and a gene coding for the PDI.

Other object of the present invention is to provide a process for the production of a polypeptide which comprises co-expressing a human PDI gene and a foreign gene coding for the polypeptide to be produced, in the above-described transformant comprising these genes so as to produce the polypeptide. The present invention further provides a process for the production of a polypeptide which comprises secreting it predominantly out of the transformant cell through the co-expression of said genes.

Other objects and advantages will be made apparent as the description progresses.

BRIEF DESCRIPTION OF THE DRAWINGS

FIG. 2 shows a boundary of the HSA prepro-sequence and the PDI gene on an expression plasmid.

DETAILED DESCRIPTION OF THE INVENTION

The present invention has been completed by finding a fusion gene for expression of PDI which is composed of a DNA fragment coding for a human serum albumin (HSA) prepro-sequence and a gene coding for human PDI, as well as a co-expression system comprising. PDI gene, yeast ERD2 gene and a certain polypeptide gene in which the three different genes are expressed simultaneously in one cell.

The following describes the present invention in detail:

Clones containing a human PDI cDNA are isolated from the human liver and placenta λgt11 cDNA libraries (Clontech, US) by the following procedures:

An $E.\ coli$ strain is infected with phage from the human liver and placenta λgt11 cDNA libraries, after which DNAs from the phage grown are fixed on a filter. Separately from this, positive clones are screened by hybridization using a 40 met synthetic oligomer DNA as a probe which corresponds to the complementary strand of a nucleic acid sequence (243–282) of human proline 4-hydroxylase (the same protein as PDI) cDNA (Pihlajaniemi, T. et al., *EMBO J.*, vol.6, p.643, 1987). The phage DNA obtained is digested with EcoRI, and the resultant 150 bp insert DNA is used as a probe for screening the PDI cDNA. Using the probe, the phage DNAs fixed on the filter are screened to isolate positive clones.

Thereafter, a plurality of positive clones obtained in such a manner are digested with EcoRI and isolate EcoRI insert DNA fragments are isolated. A restriction map of the insert of each clone is made. From the comparison of these maps with that reported by Pihlajaniemi et al., it was estimated that the full length human PDI cDNA was covered by a clone (pHPDI16) from liver and a clone (pHPDIp4) from placenta.

Determination of DNA sequences of the two clones revealed that these clones encoded human PDI cDNA consisting of 2454 base pairs in full length as shown in the SEQ ID No:1. An amino acid sequence deduced from the DNA sequence is also shown in the SEQ ID No:1. In the amino acid sequence, a mature protein seems to be composed of 491 amino acids from $Asp^1$ to $Leu^{491}$, and the 17 amino acid polypeptide preceding $Asp^1$ seems to be a signal peptide.

According to the present invention, there is provided a fusion gene for use in the expression and production of PDI, which is composed of a DNA fragment coding for a HSA prepro-sequence and the aforementioned human PDI gene.

Figure 1A:
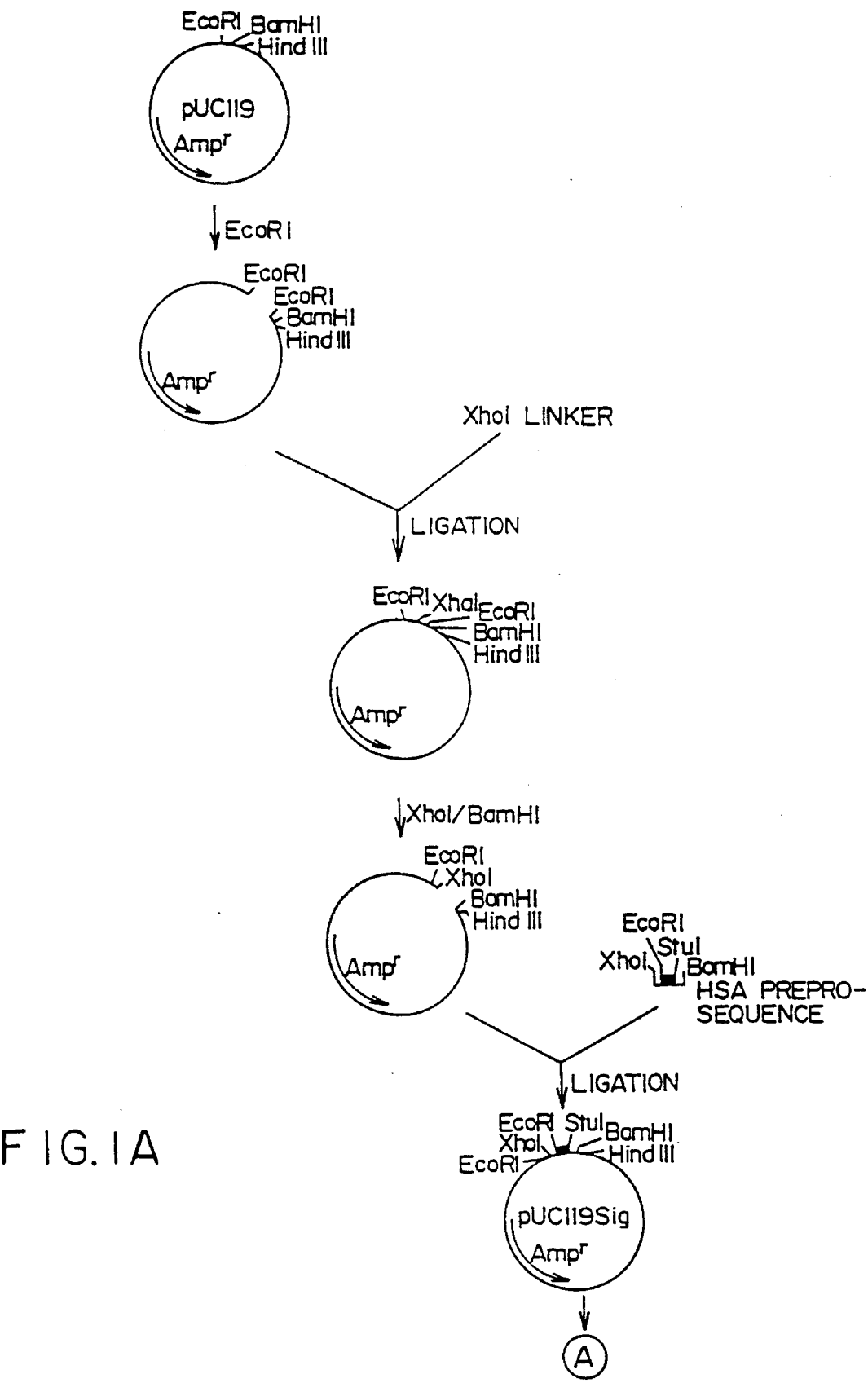
FIGS. 1A, 1B and 1C illustrate construction of the expression plasmid pAHhPDILyl.
Figure 1B:
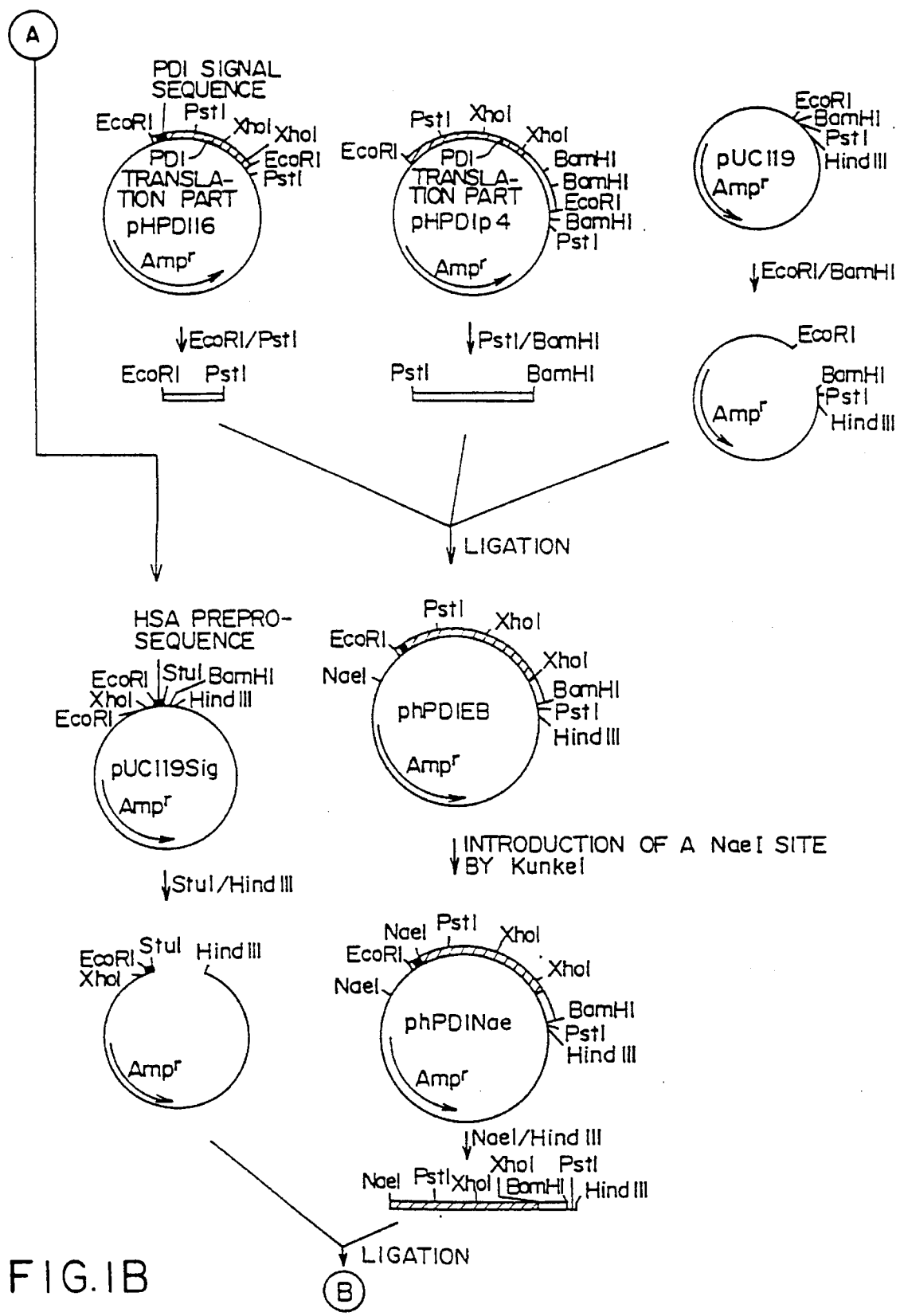
Figure 1C:
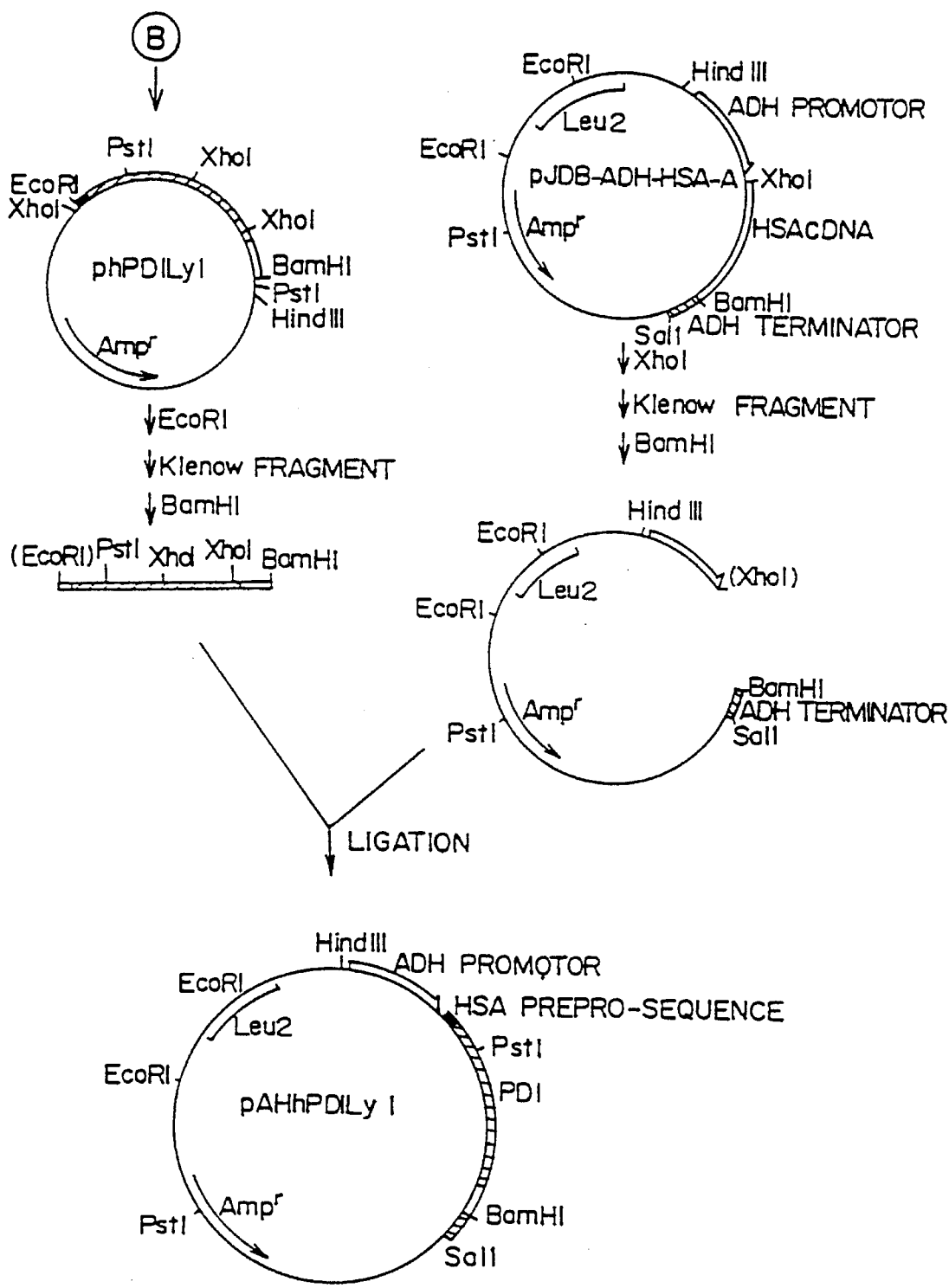

As shown in FIGS. 1A, 1B and 1C the fusion gene is constructed in general by arranging the preprosequence-encoding DNA fragment at the upstream side of the PDI gene. In this instance, however, a leader sequence for transporting human PDI into an appropriate compartment (considered to be endoplasmic reticulum) is not always limited to the HSA prepro-sequence, and other signal sequences or preprosequences may also be used as the leader sequence.

More particularly, said fusion gene may be prepared as follows:

The aforementioned clones pHPDI16 and pHPDIp4 DNAs are double-digested with EcoRI/PstI and PstI/BamHI, respectively, to produce DNA fragments of about 490 bp and about 1.3 kbp respectively, the fragments recovered are ligated with a plasmid vector pUC119 which was digested with EcoRI and BamHI to produce phPDIEB in which a NaeI cleavage site is then introduced into the boundary between the PDI signal sequence and the PDI sequence by the Kunkel's method (Kunkel, T. A., *Proc. Natl. Acad. Sci., U.S.A.*, vol.82, p.488, 1985) so as to give use to phPDINae, and thereafter the phPDINae is digested with NaeI and HindIII to give a PDI DNA fragment of about 1.7 kb which does not contain the PDI signal sequence.

Separately from this, pUC119 is digested with EcoRI, and the resultant digest is ligated with the following XhoI linker:

5'-AATTCTCGAG
        GAGCTCTTAA-5'.

After double-digesting the product with XhoI and BamHI, the digest is ligated with a prepro-sequence of HSA to produce pUC119Sig which is subsequently digested with StuI and HindIII to give a DNA fragment of about 3.2 kb A method for synthesizing the HSA preprosequence will be described later in Examples.

Thereafter, the 1.7 kb DNA fragment from phPDINae and the 3.2 kb DNA fragment from pUC119Sig origin are ligated together to produce phPDILyl which is in turn digested with EcoRI, blunt-ended with Klenow fragment, and digested with BamHI, thereby giving a fusion gene in which a leader sequence is modified and in which the human PDI gene is fused to the downstream side of the HSA preprosequence (FIG. 2).

Process for the preparation of the fusion gene according to the present invention is not limited to the above-described techniques, provided that said fusion gene has an ability for expressing PDI. Although analogs of the inventive fusion gene are not included within the scope of the present invention, it is obvious that they can be prepared easily from a corresponding gene of any animal origin other than human.

According to one embodiment of the present invention, said fusion gene has a DNA sequence coding for the −24 to +491 amino acid sequence shown in the SEQ ID No. 2. Instead of the PDI gene therein, a DNA sequence coding for the +1 to +491 amino acid sequence ($Asp^1$-$Leu^{491}$) shown in SEQ ID NO:1 may also be applied. In these instances, all genes which substantially have the same function as that of said DNA sequences, for example, derivatives having nucleotide sequences based on the degeneracy of codon, are included within the scope of the present invention. According to another embodiment of the present invention, an example of such a fusion gene includes the sequence between nucleotide 1 to nucleotide 1545 shown in SEQ ID No. 2.

An expression vector used for the insertion of the linked gene of the present invention thereinto should replicate in a host cell and have the ability for expressing therein. In general, such a useful vector contains replicon and regulatory sequences which are derived from a species compatible with a host to be used, as well as a replication origin and a marker sequence which enables selection of a phenotype from transformed cells.

As a vector for use in the construction of the expression vector, the plasmid pJDB-ADH-HSA-A (FIGS. 1A, 1B and 1C) which has been disclosed in Japanese Patent Application Laying-Open (KOKAI) No. 2-117384 filed by the present applicant may be used conveniently. This plasmid contains HSA cDNA, as well as yeast alcohol dehydrogenase I (ADH I) promoter, ADH I terminator, ampicillin resistance gene ($Amp^r$) and Leu2 gene. The HSA cDNA is removed from this plasmid by digesting it with XhoI, blunting with Klenow fragment, and then digesting with BamHI. The 5'-end of the DNA fragment of about 8 kb thus obtained is dephosphorylated, and the resultant fragment is ligated with the aforementioned fusion gene of the present invention to give the expression vector pAHhPDILyl. In this process, other type of vectors can be used provided that they are capable of expressing the fusion gene.

Examples of hosts for use in the expression of human PDI include prokaryotes such as *E. coli, Bacillus subtilis*, etc and eukaryotes such as yeast, etc. Preferred is a host cell capable of secreting the mature PDI via processing. Preferably, the host cell is yeast such as *Saccharomyces cerevisiae*, more preferably yeast strain AH22. It is obvious that eukaryotes other than yeast, for example animal cells, can be used as the host cell. Incorporation of the expression vector into a host cell can be carried out easily by conventional means such as calcium chloride, protoplast (or spheroplast)-polyethylene glycol, electroporation, etc. When the plasmid pAHhPDILyl is used as an expression vector, a desired transformant may be obtained by culturing transformed cells on SD(-Leu) plate and screening colonies grown on the plate.

A process for the production of a recombinant type human PDI comprises the steps of:

constructing an expression vector which can replicate in a host cell and express the fusion gene of the present invention therein;

isolating a host cell transformed with said expression vector;

culturing the obtained transformant under such conditions that the fusion gene can be expressed, thereby secreting said recombinant human PDI; and recovering the recombinant PDI.

Figure 4:
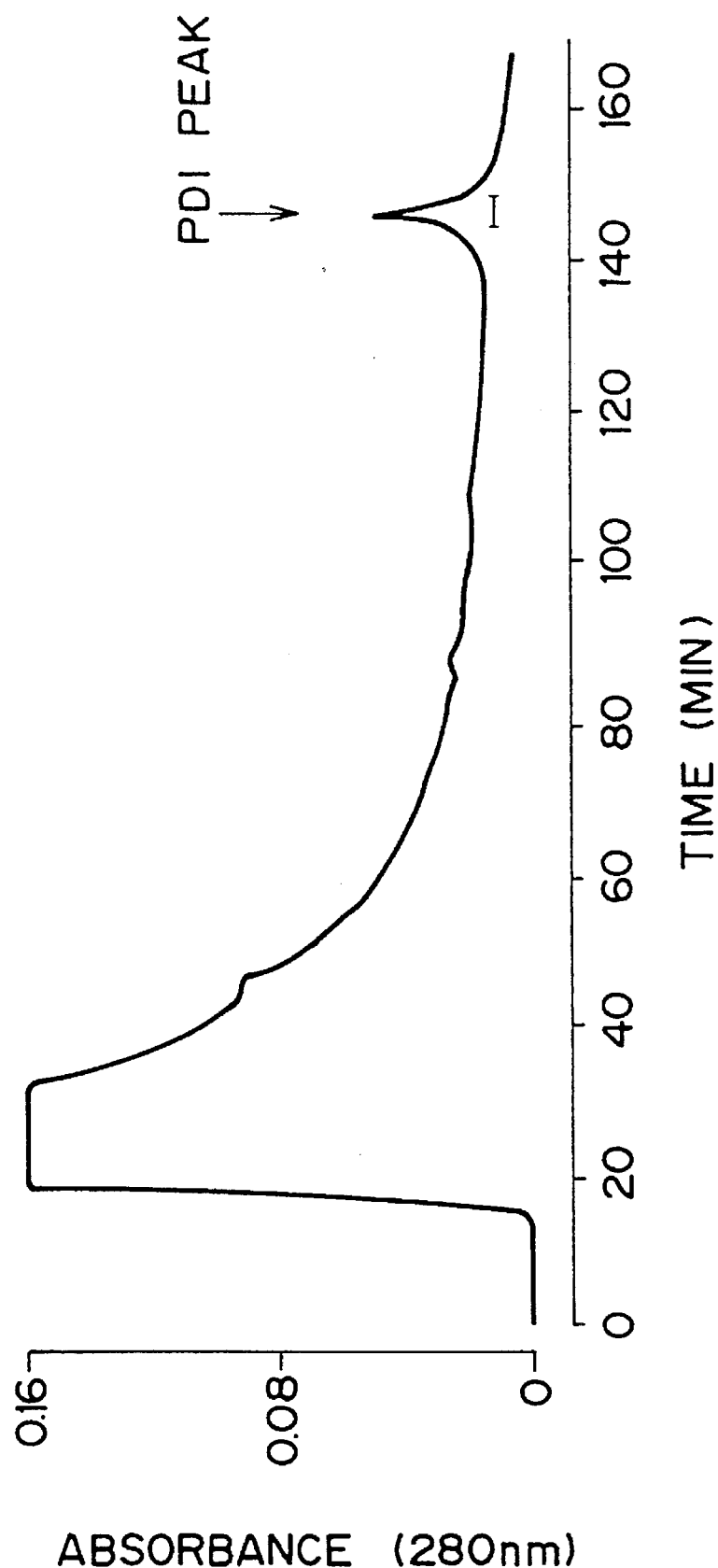
FIG. 4 illustrates the separation of a recombinant human PDI by hydrophobic column chromatography.

The recombinant human PDI can be purified easily by separating the transformed cells from a cultured medium by centrifugation, disrupting the cells if necessary, concentrating the supernatant by ultrafiltration or the like, and then subjecting the concentrate to hydrophobic column chromatography. Though not particularly limited, TSK-gel Phenyl-5PW hydrophobic column (Tosoh, Japan) may be used in the chromatography. In this case, the recombinant human PDI may be eluted by linear gradient of from 0.85 to 0M ammonium sulfate in Borate buffer (pH 8.0) containing KCl (FIG. 4). It was confirmed that the purified recombinant human PDI has a molecular weight of about 55 kDa based on the SDS-polyacrylamide gel electrophoresis analysis (FIG. 5), and practically has PDI activity as the results of determination of a degree of the refolding of scrambled ribonuclease A (see Examples).

In comparison with the natural type human PDI, it has been found that the recombinant human PDI thus prepared has the same amino acid sequence except that its N-terminal amino acid is changed from Asp to Gly, as shown in SEQ ID NO:3.

The present invention further provides a transformant comprising a fusion gene which is composed of a human PDI gene and a DNA fragment coding for a HSA preprosequence, and a foreign gene coding for a polypeptide to be produced, in a co-expressible state.

The fusion gene and the foreign gene in the transformant may be located on the same or different chromosome(s), provided that they are mutually present in a co-expressible state. Transformation of a host cell can be carried out for example by inserting the fusion gene and the foreign gene into the same or different vector(s) and introducing the resulting vector or vectors into the host cell by conventional means such as lithium chloride, protoplast (or spheroplast)-polyethylene glycol, electropotation, etc.

The foreign gene may encode a polypeptide of any type, provided that the polypeptide contains at least one disulfide linkage because the catalytic effect of an amplified and expressed PDI, that is, acceleration of the formation or exchange reaction of a disulfide bond(s) in polypeptide, is directly exhibited. In addition, the present invention can be applied to a case in which the PDI activity exerts influence on proteins relating to gene expression, polypeptide folding or transport, thereby indirectly improving the productivity of proteins encoded by the foreign genes. According to the embodiment of the present invention, the foreign gene is a gene coding for HSA.

The term "polypeptide" as used herein means a short- or long-chain peptide and protein.

Examples of hosts include prokaryotes such as *E. coli, Bacillus subtilis*, etc and eukaryotes such as yeast, animal cells, etc. Preferred is a host cell capable of secreting a mature polypeptide through post-translational modification and processing, more preferably eukaryotes, and most preferably yeast.

The present invention also provides a process for producing a polypeptide, which comprises the following steps of:

co-expressing a human PDI gene and a foreign gene coding for the polypeptide to be produced, in the above-described transformant so as to produce the polypeptide; and recovering the polypeptide.

Figure 8:
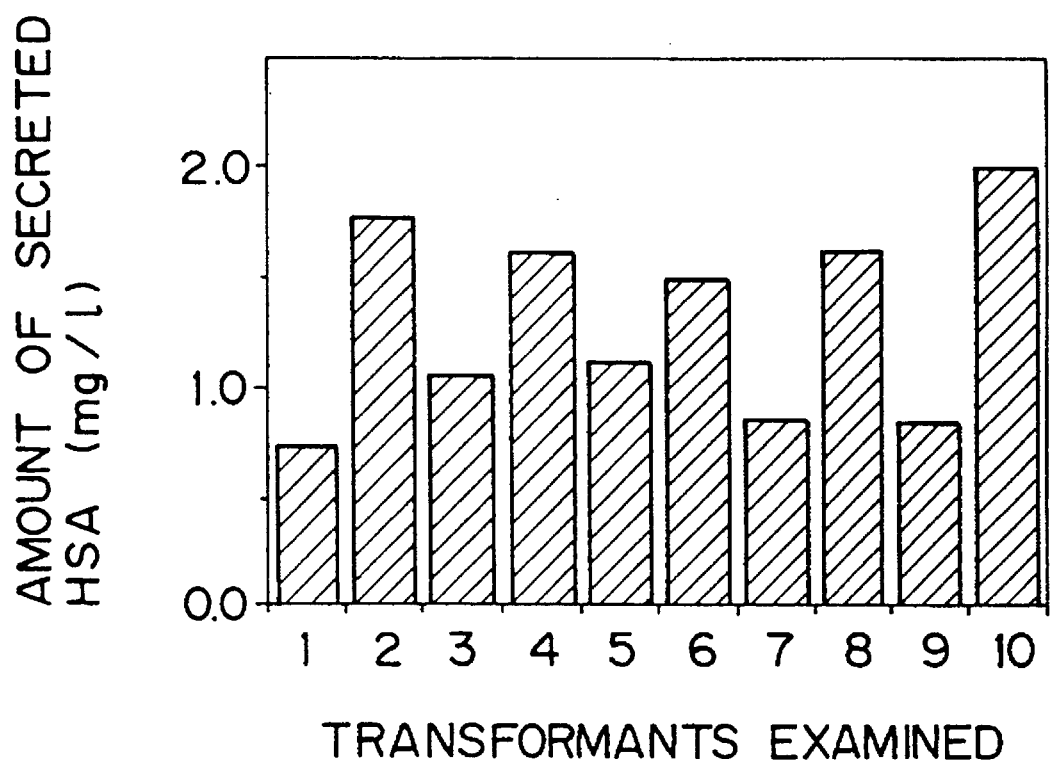
FIG. 8 shows the result of densitometric determination of the amount of secreted HSA using the SDS-polyacrylamide gel electrophoresis gel of FIG. 7.

When PDI is co-expressed within an HSA-producing yeast strain (pAHhPDILy1/HIS23) transformed with a human PDI expression plasmid in an appropriate medium, a secretion level of HSA practically increases by about 60% in average in comparison with the case of a non-transformed HSA-producing yeast strain (pAH/HIS23) (FIG. 8).

Although we do not intend the present invention to restrict by theory, the increase in the secretion level of HSA by co-expression can be explained as follows:

HSA is a protein containing 17 disulfide bonds. It is known also that formation of its higher-order structure is enhanced in the presence of a stoichiometric amount of PDI in in vitro refolding experiments of a denatured protein.

HSA is secreted from the yeast strain HIS23 as a watersoluble molecule, but some of the HSA molecules are also detectable within the yeast cell. When the intracellular HSA was analyzed by SDS-polyacrylamide gel electrophoresis, it was detected as a single band with the same mobility as that of a normal HSA molecule in the presence of a reducing agent, while detected as discontinuous bands having a larger molecular weight than normal HSA in the absence of a reducing agent, clearly showing a different behavior from that of normal HSA. These results indicate that the presence of intracellular HSA molecules is based upon the incomplete formation of an intramolecular disulfide bond(s). In a yeast strain allowed PDI to co-express together with HSA, however, an intracellular HSA molecule was detected as a more narrow band on a SDS-polyacrylamide gel electrophoresed without a reducing agent when compared with an intracellular HSA sample prepared from a yeast strain which can not co-express a foreign PDI cDNA together with HSA. This indicate that PDI enhances the formation of a normal disulfide bond(s) in the HSA molecule and thereby assists the formation of the higher-order structure of HSA molecule more efficiently. Accordingly, it is suggested that the co-expression of PDI reduces chances of causing the association of HSA molecules having unstable structure and their decomposition by proteases in the host cell, thereby increasing the secretion of HSA molecules.

When the amount of HSA mRNA in the HIS23 in which PDI was co-expressed is compared with the amount in a control without co-expression by means of Northern blotting, increase in the amount of HSA mRNA can be found in the former cells in which the PDI gene was expressed. These results suggest that PDI exerts influence not only directly on HSA molecules but also on the transcription level of the HSA gene. However, it seems to be reasonable that the increment of HSA production level is based on the direct influence of PDI on HSA molecules by their coexistence in endoplasmic reticulum, because the increase in the amount of secreted HSA has a correlation to an increased level of the secretion of human PDI out of the yeast cell. In addition, when the amounts of HSA and PDI secreted from the HIS23 cells are compared with each other, PDI is secreted in several times larger amounts than HSA, and the level of human PDI detectable within the cells is also higher than HSA. These results, therefore, indicate that PDI is localized in the endoplasmic reticulum of the yeast cells in an enough amount to enhance the in vitro refolding of a denatured HSA, which also supports the direct effect of PDI on HSA.

Thus, it is highly possible that the effect of the co-expression of PDI on an increment of the amount of secreted HSA is based on the direct influence of PDI on the formation of the higher-order structure of HSA. In consequence, such a similar secretion-improving effect can also be expected in other general secretory proteins in which the formation of a disulfide bond(s) contributes to the formation and stability of their higher-order structures, by highly amplified co-expression of PDI in the same host cell.

The present invention also provides a transformant comprising the following expression units integrated on yeast chromosome in a co-expressible state:

an expression unit containing a gene coding for a receptor protein ERD2 from yeast or analog thereof which is capable of binding to a protein localizing in endoplasmic reticulum and having a signal for staying therein; and an expression unit containing a gene coding for said protein localizing in endoplasmic reticulum and having a signal for staying therein.

Such a transformant is useful for the preparation of another transformant cell capable of secreting a useful polypeptide predominantly out of a transformant, by transforming its host cell with an expression vector which contains a foreign gene coding for the polypeptide, said polypeptide being a subject of function of the aforesaid protein localizing in endoplasmic reticulum.

The wording "protein localizing in endoplasmic reticulum and having a signal for staying therein" as used herein is intended to include any protein which can localize in the endoplasmic reticulum cavity after in vivo protein synthesis, which has a signal for staying in endoplasmic reticulum, such as amino acid sequence "KDEL (SEQ ID NO:5)", "HDEL (SEQ ID NO:6)", "DDEL (SEQ ID NO:7)", "ADEL (SEQ ID NO:8)", "SDEL (SEQ ID NO:9)", "RDEL (SEQ ID NO: 10)", "KEEL (SEQ ID NO:11)", "QEDL (SEQ ID NO:12)", "HIEL (SEQ ID NO:13)", "HTEL (SEQ ID NO:14)", "KQDL (SEQ ID NO:15)" and the like, on the C-terminus of the protein, and which is capable of binding to a receptor protein ERD2 from yeast or analog thereof. Examples of such a type of proteins include PDI, glucose-regulated protein 78 (grp78), glucose-regulated protein 94 (grp94), etc. Preferred is a protein having a useful function for a polypeptide, more preferably PDI. The PDI is known as an enzyme which catalyzes the exchange reaction of a thiol/disulfide bond and rises a rate of the refolding of a denatured protein (Schein, *Bio/Technology*, vol.7, pp. 1141–1148, 1989; Freedman, *Cell*, vol. 57, pp. 1069–1072, 1989). According to the present invention, the above-mentioned protein localizing in endoplasmic reticulum also includes a protein which has no said signal natively on its C-terminus but has been modified by genetic engineering techniques so as to provide it with the signal.

The wording "receptor protein ERD2 from yeast or analog thereof" as used herein means an receptor protein from yeast which is capable of accepting any protein localizing in endoplasmic reticulum and having a signal for staying therein. An example of the DNA sequence encoding the ERD2 protein is a sequence reported by Semenza et al. (Semenza, J. C., Hardwick, K. G., Dean, N. and Pelham, H. R. B., *Cell*, vol.61, p.1349, 1990) which is included herein as reference, although any other modified DNA sequence may also be included provided that the modification does not spoil the function of the ERD2. Such a modified DNA sequence is, for example, a DNA sequence coding for a "KDEL" receptor from mammals which has a high homology to the ERD2 protein (Lewis, M. J. and Pelham, H. R. B., *Nature*, vol. 348, p. 162, 1990).

The following describes a process for the preparation of an expression vector which comprises a gene coding for the yeast ERD2. It should be understood, however, that the vector obtained by the process is a representative one and that it is not intended to limit to the vector alone.

Figure 9:
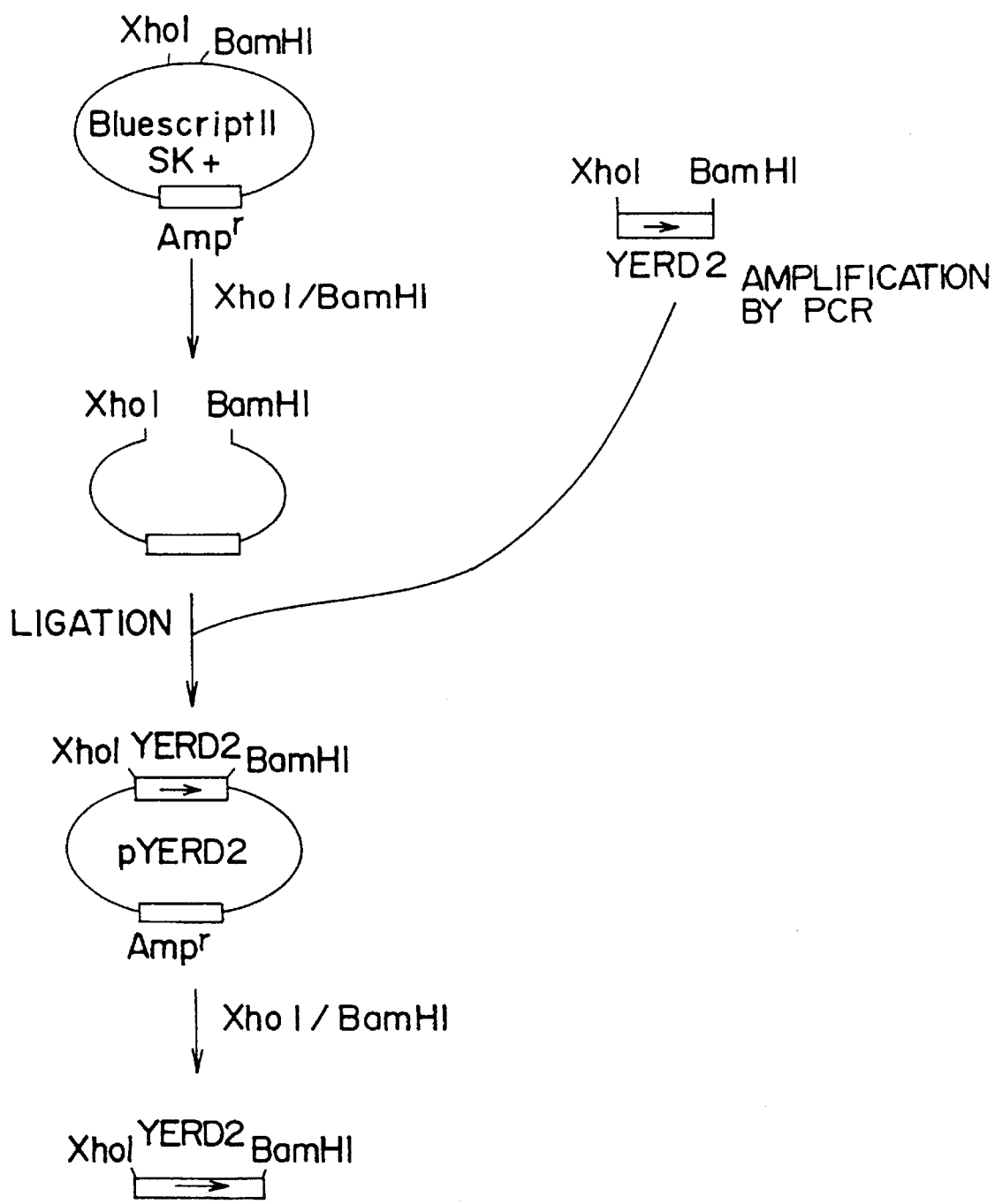
FIG. 9 illustrates a preparation of the XhoI-BamHI restriction fragment of YERD2.

A gene encoding the yeast ERD2 is obtained by the polymerase chain reaction (PCR) technique (Mullis, K. B. and Faloona, F., *Meth. Enzymol.*, vol.155, p.335, 1987) using a genomic DNA prepared from the yeast strain S288C as a template. Primers used are: 5'-TTTTTCTCGAGTAAG-CAATGAATCCGTT-3' (SEQ ID NO:16) and 5'-AAAAAG-GATCCTGCGAACACTATTTAAA-3' (SEQ ID NO:17), which were designed based on the DNA sequence of the yeast ERD2 gene (Semenza, J. C., Hardwick, K. G., Dean, N. and Pelham, H. R. B., *Cell*, vol.61, p.1349, 1990). The ERD2 gene obtained is inserted into a XhoI/BamHI site of the plasmid vector BluescriptII SK+ and then subcloned (FIG. 9).

A vector for use in the incorporation of the ERD2 gene is capable of expressing said gene in a host cell and of replicating itself therein along with the replication of the host chromosome after its integration on the chromosome. In general, the vector contains a marker sequence which enables selection of a phenotype from transformed cells.

Figure 10:
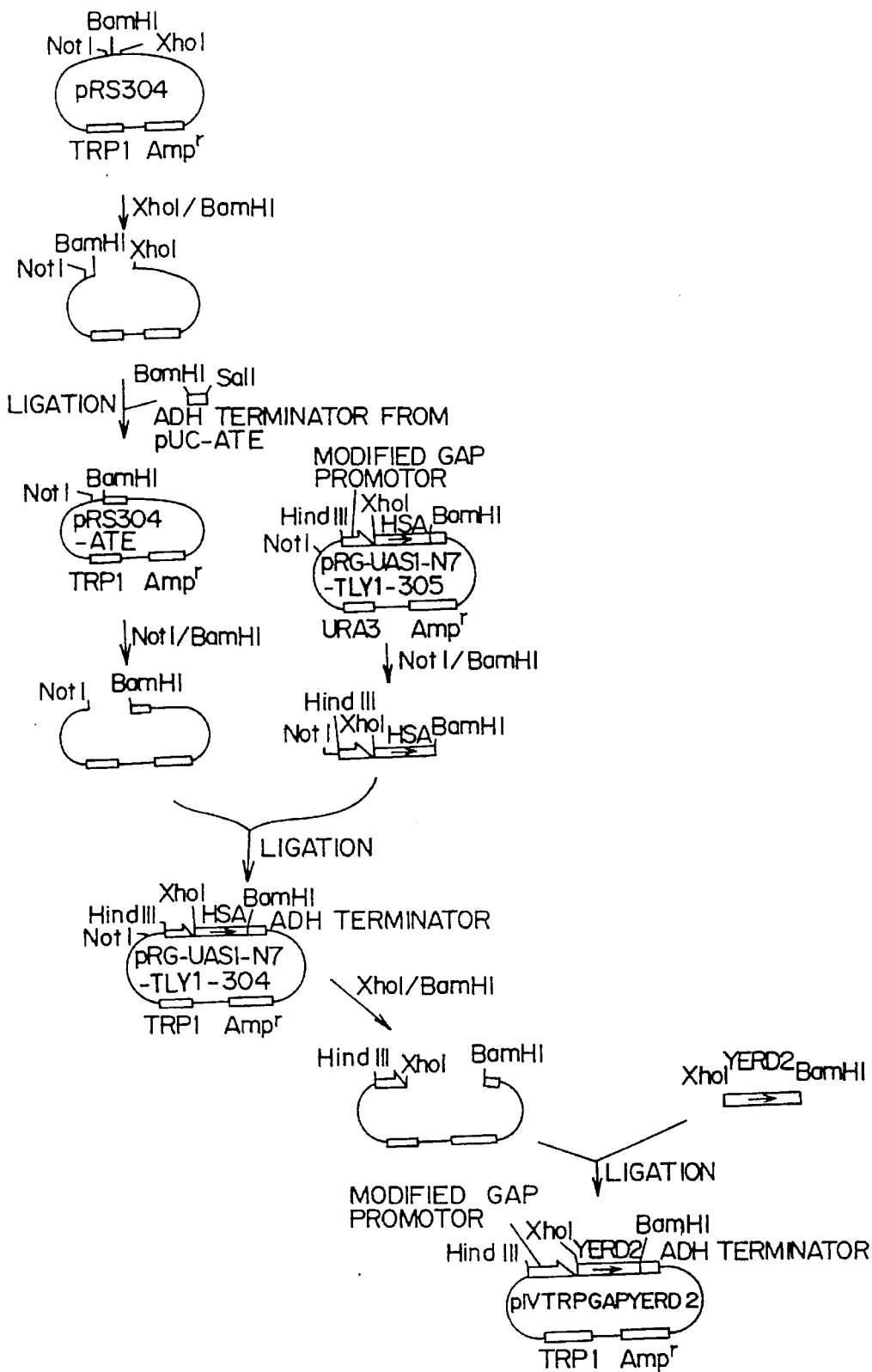
FIG. 10 illustrates a construction of the expression plasmid pIVTRPGAPYERD2.
Figure 11:
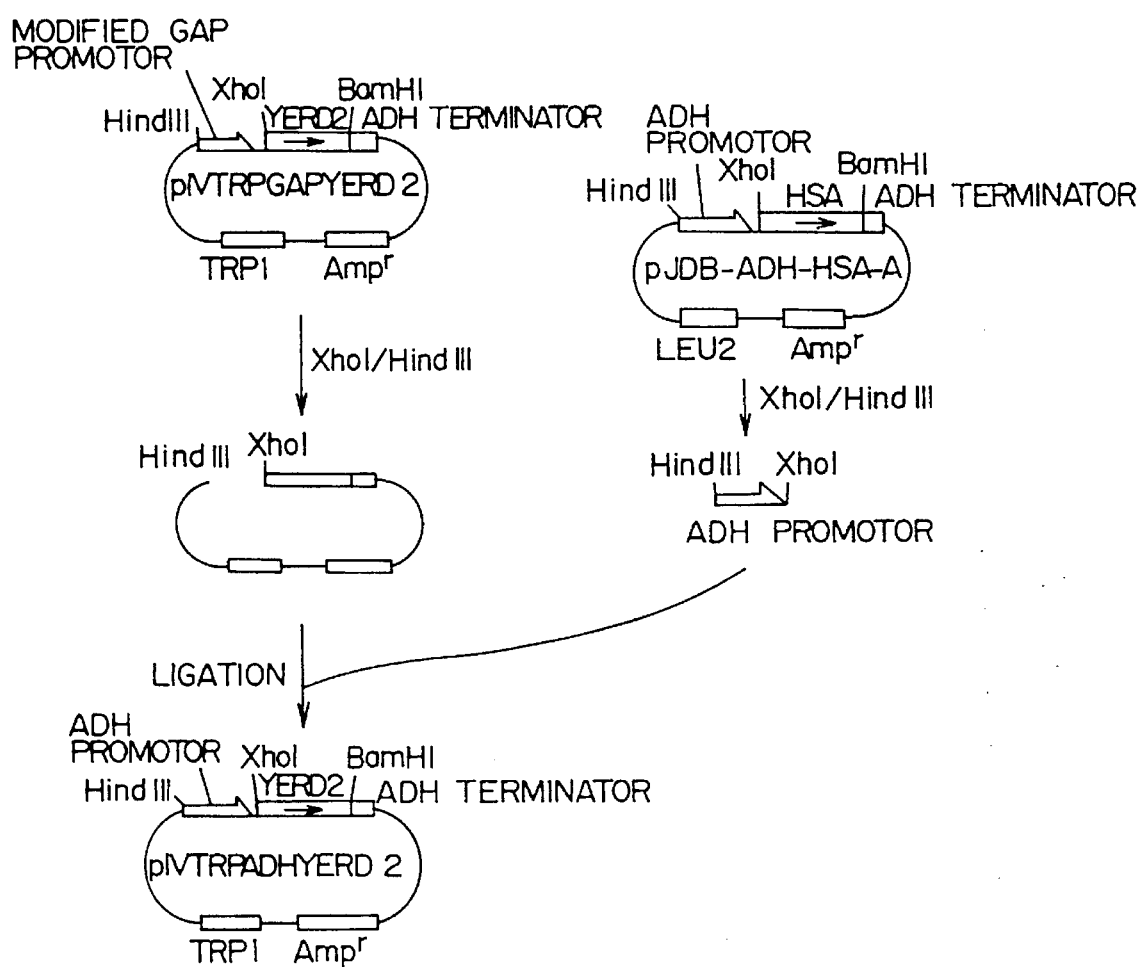
FIG. 11 illustrates a construction of the expression plasmid pIVTRPADHYERD2.

As a vector for use in a construction of the expression vector of the present invention, plasmid pRG-UAS1-N7-TLY1-304 may be used conveniently (A procedure for constructing the plasmid will be described in detail in Examples.). This plasmid contains human serum albumin (HSA) cDNA, as well as a modified promoter derived from a yeast glyceraldehyde-3-phosphate dehydrogenase (GAP) promoter, a yeast alcohol dehydrogenase I (ADH) terminator, an ampicillin resistance gene (Amp$^r$) and a TRP1 gene. The HSA cDNA is removed from this plasmid by digesting it with XhoI and BamHI, which is then ligated with the yeast ERD2 gene to give the vector pIVTRPGAPYERD2 (FIG. 10). Thereafter, the pIVTRPGAPYERD2 can be converted into expression plasmid pIVTRPADHYERD2 by digesting pIVTRPGAPYERD2 with HindIII and XhoI to remove the modified GAP promoter and by ligating the resultant fragment with a yeast ADH promoter (FIG. 11). Any other type of vectors which function for the expression of the ERD2 gene may be used instead of the pRG-UAS1-N7-TLY1-304.

In addition to the alcohol dehydrogenase I promoter, examples of other promoter sequences useful in the expression vector include 3-phosphoglycerate kinase promoter (Hitzenman et al., *J. Biol. Chem.*, vol.255, p.2073, 1980) and promoters for other glycolytic enzymes such as enolase, glyceraldehyde-3-phosphate dehydrogenase, hexokinase, etc (Hess et al., *J. Adv. Enzyme Reg.*, vol.7, p.149, 1968; Holland et al., *Biochemistry*, vol.17, p.4900, 1978). Any terminator sequence compatible with a yeast strain may be used in the expression vector, examples of which are terminators for the above enzymes.

The expression vector may further contain a yeast-originated gene such as the TRP1 gene. This gene can be used as a phenotype selection marker when a desired transformant is isolated, and it can also function in order to give rise to the homologous recombination of an ERD2 expression unit on yeast chromosome when the vector is integrated onto the chromosome. The expression vector may also contain a yeast-compatible replication origin, a ribosome binding site, a marker sequence such as antibiotic resistant gene, and other useful sequences.

A preferred example of the above-mentioned gene coding for a protein localizing in endoplasmic reticulum and having a signal for staying therein, is a PDI gene or a fused gene which is composed of the PDI gene and a HSA preprosequence. Examples of the PDI gene used in the present invention include an eukaryote PDI gene, particularly mammal PDI gene, more particularly human PDI gene, and its derivatives (substitution, addition, modification, deletion, etc). The human PDI gene or its derivative has for example a DNA sequence coding for the PDI amino acid sequence shown in SEQ ID NO:1 or SEQ ID NO:3. With respect to the construction of a PDI expression unit, the above descriptions about the construction of ERD2 expression system are applied thereto directly. Its illustrative procedures will be described in Examples.

Although not particularly limited, a strain belonging to the genus Saccharomyces, such as *Saccharomyces cerevisiae*, may be used as a yeast host. It is obvious that eukaryotes other than yeast, for example animal cells, can also be used as the host.

Transformation can be carried out easily by conventional techniques such as those with lithium chloride, protoplast(or spheroplast)-polyethylene glycol, electroporation, etc.

When the transformant of this invention contains TRP1 gene, it may be isolated by culturing the transformed cell on an SD (-Leu, -His, -Ade, -Ura, -Trp) plate and screening colonies on the plate.

The present invention also provides a transformant comprising the following expression units integrated on yeast chromosome in a co-expressible state:

an expression unit containing a gene coding for a receptor protein ERD2 from yeast or analog thereof which is capable of binding to a protein localizing in endoplasmic reticulum and having a signal for staying therein;

an expression unit containing a gene coding for said protein localizing in endoplasmic reticulum and having a signal for staying therein; and an expression unit containing a foreign gene coding for a polypeptide which is a subject of function of said protein localizing in endoplasmic reticulum and having a signal for staying therein.

The foregoing descriptions concerning the expression unit comprising a gene encoding a ERD2 or analog thereof and the expression unit; the expression unit comprising a gene encoding the aforesaid protein localizing in endoplasmic reticulum; the yeast host; and the transformation process, may directly be applied to this case.

With regard to the polypeptide to be expressed, any type of polypeptides which are susceptible to the PDI activity may be used. According to the embodiment of the present invention, HSA gene may preferably be used as the gene encoding a polypeptide.

The ERD2 gene and other above-described genes which are carried in the two types of the transformants of the present invention may be located on the same or different genome(s) in the host cell, provided that they are mutually present in a co-expressible state. For example, the ERD2 gene and other above-described genes may be inserted into the same vector or preferably different vectors, incorporated into the same host cell, and then integrated into the host chromosome by homologous recombination. Each of the expression units containing the ERD2 gene and other above-described genes may be contained in plural numbers in the chromosome, provided that they are mutually present in a co-expressible state.

According to another embodiment of the present invention, the transformant includes the HSA-highly producing yeast strain SN35A-1 PUAET.

Figure 13:
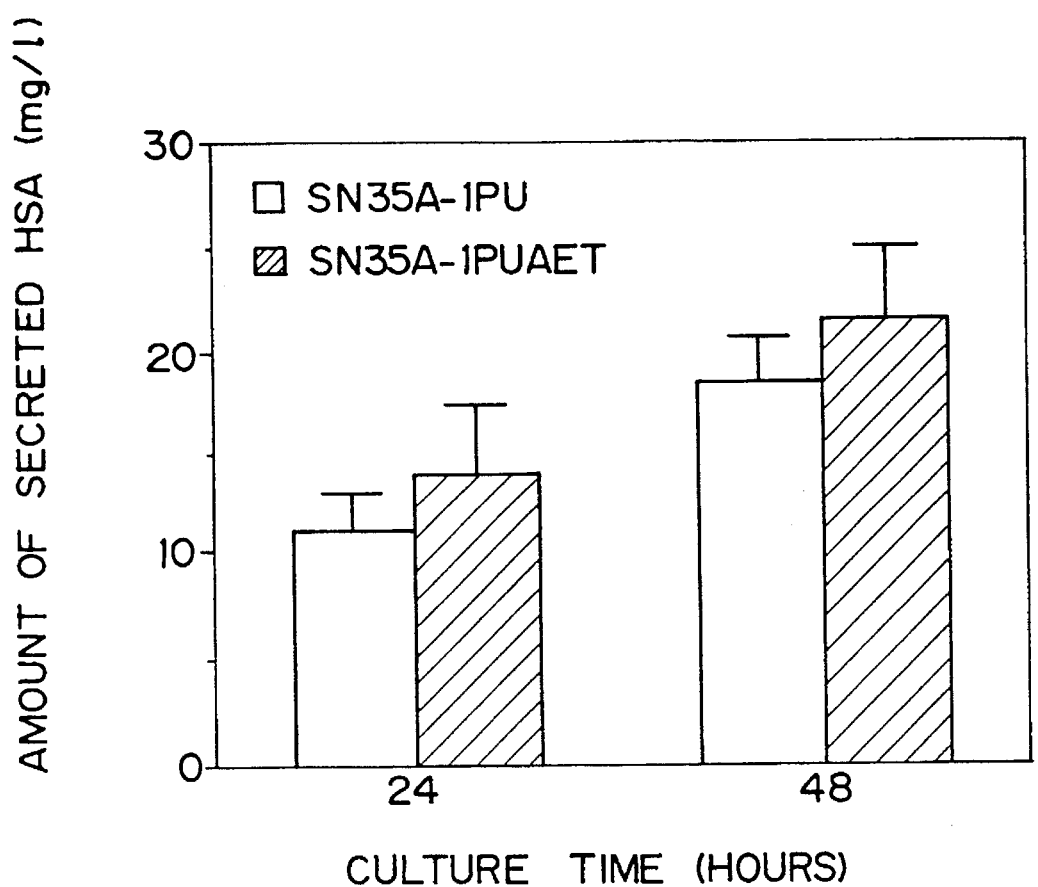
FIG. 13 shows the result of densitometric determination of an amount of HSA secreted from strains SN35A-1PU and SN35A-1PUAET using SDS-electrophoresis gels.
Figure 12:
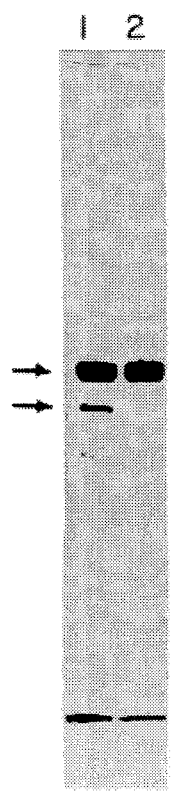
FIG. 12 is a photograph showing the results of SDS-polyacrylamide gel electrophoresis of human PDI and HSA which were secreted from the strain SN35A-1PU capable of expressing both human PDI and HSA and from the strain SN35A-1PUAET introduced a yeast ERD2 expression system into the SN35A-1PU, wherein lane 1 is a supernatant of the culture of SN35A-1PU and lane 2 is a supernatant of the culture of SN35A-1PUAET.

This yeast strain is obtained by incorporating an expression vector containing the yeast ERD2 gene into the SN35A-1PU (obtained by introducing a human PDI expression unit into the locus ura3 of a HSA-highly secreting yeast strain SN35A (Japanese Patent Application No. 3-226107); see Examples) and then by integrating the ERD2 gene into the trp1 site on the yeast chromosome by homologous recombination. The yeast transformant SN35A-1PUAET thus obtained can express the yeast ERD2, human PDI and HSA simultaneously. In comparison with the SN35A-1PU without a ERD2 expression system, the secretion of PDI into a culture medium is repressed significantly, and an average level of the secretion of expressed HSA increases by about 26% after culturing for 24 hours and by about 17% after culturing for 48 hours as compared with the control (FIGS. 12 and 13).

The present invention also provides a process for the production of a polypeptide, which comprises the following steps of:

culturing a transformant containing the aforementioned three expression units in an appropriate medium, and bringing about co-expression such that the polypeptide is predominantly secreted out of the transformant cell, the polypeptide being a subject of function of a protein which localizes in endoplasmic reticulum and has a signal for staying therein, while both a receptor protein ERD2 from yeast or analog thereof which is capable of associating with said protein localizing in endoplasmic reticulum, and said protein as a ligand for the ERD2 remain in endoplasmic reticulum; and recovering said polypeptide secreted.

According to the process of the present invention, in order to prevent leakage of said protein localizing in endoplasmic reticulum from a host cell, the expression levels of the ERD2 protein or analog thereof and of the protein localizing in endoplasmic reticulum are regulated by a promotor sequence fused to the gene of said protein.

Although we do not intend to restrict the present invention by theory, both the repressed secretion of PDI and the enhanced secretion of HSA by co-expression of the ERD2 may be explained as follows:

With regard to a retention mechanism of PDI in the endoplasmic reticulum, it is considered generally that the ERD2 localized in the endoplasmic reticulum acts as a receptor of said signal which is attached to the C-terminus of PDI. When PDI is expressed under control of a strong promoter (ex. modified GAP promoter herein), the amount of intracellularly expressed PDI exceeds the PDI-binding capacity of ERD2 present in endoplasmic reticulum, and accordingly the excess PDI molecules "over flow" outside the host cell. Such an "over flow" of PDI has been observed in the case of SN35A-1PU which in fact secrets the excess PDI out of yeast cells, by the present inventors expressing human PDI (Japanese Patent Application No. 2-295017 filed by the present applicant). On the other hand, the increase of the amount of secreted HSA in the case of SN35A-1PUAET can be explained by that the PDI expressed in large quantity, remains within the yeast cell because the PDI-accepting capacity of ERD2 is enhanced in the endoplasmic reticulum by allowing a large number of ERD2 to co-express under control of the ADH promoter.

In this case, it is assumed that the co-expression of ERD2 improves the aforesaid PDI-retention efficiency in the endoplasmic reticulum, and thereby an amount of secreted HSA as a substrate of PDI, is increased.

This indicates strongly that the effect of PDI on the enhanced secretion of HSA is not due to the extracellular stabilization of HSA by PDI, but due to the PDI activity to catalyze the formation of the higher-order structure (i.e., formation of S-S bond) of HSA in host cell (in the endoplasmic reticulum).

Therefor, the improvement of a PDI-retention efficiency in the endoplasmic reticulum by the co-expression of a yeast ERD2 gene provides a system in which the PDI can function maximally by allowing a large quantity of expressed PDI to localize within a suitable intracellular compartment where the PDI can function naturally.

The present invention has a general utility value for the purpose of allowing any polypeptide having a signal foe staying in endoplasmic reticulum which is acceptable by ERD2, to work efficiently on a foreign polypeptide as its substrate like the case of PDI.

The present invention has established for the first time a means in which the secretion of PDI is repressed and the effect of PDI to increase the secretion of serum albumin is improved, by constructing an expression system of a yeast ERD2 gene and by applying this system to expression systems of human PDI and HSA. The process of the present invention can be used as a means to improve the above-described retention efficiency in conjunction with an expression system of a protein localizing in the endoplasmic reticulum of an eukaryote, as well as a means to improve a production efficiency of a useful polypeptide by introducing the co-expression system into a production system of the polypeptide which is a substrate of said protein.

The following non-limited examples will be provided to further illustrate the present invention.

EXAMPLE 1

Cloning of human PDI (protein disulfide isomerase) cDNA

About 100,000 clones of human liver λgt11 cDNA library (Clontech) were mixed with 500 µl of a culture of *E. coli* strain Y1090 which has been precultured overnight at 37° C. in LB medium (1% Bacto-trypton, 1% NaCl and 0.5% yeast extract) supplemented with 0.2% maltose. After further adding 5 µl of 1M $MgCl_2$ solution thereto, the mixture was incubated at 37° C. for 10 minutes to infect the *E. coli* cells with the phage particles. The resulting cells were added to 50 ml of an LB top agar medium (LB medium, 10 mM $MgCl_2$ and 0.7% agarose), and then mixed and inoculated on a LB agar plate (23 cm×23 cm). After solidifying the top agar medium, the plate was incubated overnight at 37° C. so as to grow the phage particles. The phage particles obtained were transferred onto a filter (Hybond-N, Amersham). With the phage-attached side upward, the filter was put for 1 minute on a 3 MM filter paper (Whatman) which has been soaked in an alkaline solution (0.5N NaOH and 0.15M NaCl), and then for further 1 minute on the same filter paper which has been soaked in a neutral solution (1M Tris-HCl (pH 7.5) and 1.5M NaCl). Thereafter, the filter was washed with 2×SSC solution (20×SSC=3M NaCl+0.3M trisodium citrate), air-dried and then exposed to UV ray for 2 minutes so as to fix the phage DNA on the filter. Using the filter thus obtained, a screening of human PDI cDNA was carried out according to the following procedure:

As a probe to be used, a 40 mer oligomer DNA (5'-TGGCGTCCACCTTGGCCAACCT-GATCTCGGAACCTTCTGC-3' (SEQ ID NO:18)) which corresponds to the complementary chain of the 243–282 base sequence of human proline-4-hydroxylase (the same protein as PDI) cDNA (Pihlajaniemi, T. et al., *EMBO J.*, vol. 6, p. 643, 1987) was synthesized using an automatic DNA synthesizer (Model 380B, Applied Biosystems).

The 5'-end of the synthesized DNA was labeled by phosphorylation, by incubating 20 pmoles of the DNA at 37° C. for 60 minutes in 50 μl of 50 mM Tris-HCl (pH 7.5) buffer containing 10 mM $MgCl_2$, 5 mM dithiothreitol, 100 μCi [$\gamma$-$^{32}$P] ATP (~3000 Ci/mmol, Amersham) and 12 units of T4 polynucleotide kinase (Takara Shuzo, Japan). The filter obtained above was soaked at 37° C. for 1 hour in the prehybridization solution which consists of 5×Denhardt solution (100×Denhardt solution=2% bovine serum albumin+2% Ficol 400+2% polyvinyl pyrrolidone), 1M NaCl, 50 mM Tris-HCl (pH 7.5), 10 mM EDTA (pH 8.0), 0.1% sodium dodecyl sarcosinate and 20 μg/ml of an ultrasonic-treated salmon sperm DNA. The filter was further soaked in a hybridization solution (prepared by supplementing the prehybridization solution with about $10^6$ cpm/ml of the aforementioned labeled DNA) for 15 hours at 37° C. The resulting filter was washed with 2×SSC solution at room temperature and then with 2×SSC+0.1% sodium dodecyl sarcosinate solution at 42° C. for 30 minutes, followed by its exposure to an X-ray film (XAR-5, Kodak) overnight at −80° C. After development of the film, 8 positive signals were detected by the primary screening. Phage particles corresponding to those signals were recovered from the aforesaid plate by cutting it out as gel sections, soaked each of the gel sections in 1 ml of SM buffer (100 mM NaCl, 10 mM $MgCl_2$, 50 mM Tris-HCl (pH 7.5) and 0.01% gelatin), and left overnight at 4° C. so as to recover the phage from the gel into the solution. When the 8 positive phages from the primary screening were further subjected to a second screening under the same conditions as those of the primary screening, only one of them remained as a positive clone. This clone was further subjected to a third screening in order to isolate it as a homogeneous positive clone.

A phage DNA was prepared from the positive clone obtained finally by the method of Leder et al. (Leder, P., Tiemeir, D. and Enquist, L., *Science*, vol. 196, p. 175, 1977). The thus prepared phage DNA (1/5 vol) was digested at 37° C. for 1 hour in 50 μl of the digestion solution consisting of 100 mM Tris-HCl (pH 7.5), 100 mM NaCl, 6 mM $MgCl_2$, 6 mM mercaptoethanol, 0.1% gelatin, 20 μg/ml of ribonuclease A and 20 units of EcoRI (Nippon Gene, Japan). By 0.8% agarose gel electrophoresis of the resulting digest, it was found that this positive clone contains an insert DNA fragment of about 150 bp. The insert DNA was separated and purified using glass powder (Gene Clean™, Bio-101). About 20 ng of the recovered DNA fragment and about 100 ng of pUC19 vector which has been digested with EcoRI were added to the mixture of Liquid A 20 μl and Liquid B 4 μl from the DNA ligation kit (Takara Shuzo, Japan), and the resulting mixture was then incubated at 16° C. for 15 hours to obtain a recombinant plasmid in which both DNA fragments were linked together. Using 10 μl of this reaction mixture, transformation of *E. coli* strain TG1 was carried out by the Mandel's method (Mandel, M. and Higa, A., *J. Mol. Biol.*, vol. 53, p. 154, 1970). The transformant thus obtained was cultured overnight at 37° C. in 100 ml of LB medium supplemented with 25 μg/ml of ampicillin, and a plasmid DNA was purified from the cultured cells by alkaline lysis method (Birnboim, H. C. and Doly, J., *Nucleic Acids Res.*, vol.7, p.1513, 1979). 10 μg of the plasmid DNA was digested at 37° C. for 1 hour in 200 μl of the digestion solution consisting of 100 mM Tris-HCl (pH 7.5), 100 mM NaCl, 6 mM $MgCl_2$, 6 mM mercaptoethanol, 0.1% gelatin and 100 units of EcoRI (Nippon Gene, Japan). The digest was extracted with phenol, concentrated by ethanol precipitation and then subjected to 0.8% agarose gel electrophoresis. Thereafter, an insert DNA fragment of about 150 bp was recovered by glass powder technique, for use as a probe in the following PDI cDNA screening.

In order to obtain a clone which contains the full length human PDI cDNA, screenings were carried out again from about 50,000 clones of human liver λgt11 cDNA library and about 50,000 clones of human placenta λgt11 cDNA library (Clontech). Filters on which phage DNA molecules of the two libraries were fixed were prepared in the same manner as described in the foregoing. In this instance, about 100 ng of the aforementioned 150 bp human PDI cDNA fragment was isotope-labeled using [$\alpha$-$^{32}$P] dCTP (>400 Ci/mmol, Amersham) and a nick translation kit (Amersham), and the labeled cDNA fragment was used as a probe in the screening. After soaking the above two filters in the aforementioned prehybridization solution for 1 hour at 60° C. the filters were further soaked in a hybridization solution (prepared by supplementing the prehybridization solution with about $10^6$ cpm/ml of the labeled DNA) for 15 hours at 60° C. The resulting filters were washed with 2×SSC solution at room temperature and then with 0.5×SSC+0.1% sodium dodecyl sarcosinate solution at 65° C. for 1 hour, followed by their exposure to X-ray films (XAR-5, Kodak) overnight at −80° C. After development of the films, 6 positive signals were found from the liver cDNA library, and 5 positive signals from the placenta cDNA library. By subjecting these clones to second and third screenings, 4 positive clones were isolated from the liver cDNA library, and 3 positive clones from the placenta cDNA library. The EcoRI insert DNA fragments of the obtained 7 clones were separately subcloned into an EcoRI site of plasmid vector pUC19 in the same manner as described above in order to make restriction maps for the inserts of the 7 clones. As the results, 4 clones obtained from the liver cDNA library and 2 clones from the placenta cDNA library were found to overlap one another. In addition, it was estimated that the full length human PDI cDNA desired is covered by one of the liver-originated clones (pHDPI16) and one of the placenta-originated clones (pHDPIp4) based upon the comparison of restriction maps of these clones with that reported by Pihlajaniemi et al. DNA base sequences of the two clones were determined using M13 SEQUENCING KIT (Toyobo, Japan.), M13 Sequencing Kit (Takara Shuzo) and an automatic DNA sequencer (370A, Applied Biosystems). Comparison of the thus determined sequences with the data reported by Pihlajaniemi et al. confirmed that the full length human PDI cDNA which consists of 2454 base pairs is encoded by these two clones (SEQ ID No:1).

Construction of plasmid for human PDI expression in yeast

A plasmid for use in the expression of human PDI in yeast was constructed by the following procesure, using the above two clones, pHPDI16 and pHPDIp4, which encode human PDI cDNA (FIG. 1):

About 1 μg of pHPDI16 DNA prepared by the alkaline lysis method was digested at 37° C. for 1 hour in 20 μl of the digestion solution consisting of 10 mM Tris-HCl (pH 7.5), 100 mM NaCl, 6 mM $MgCl_2$, 6 mM mercaptoethanol, 0.1% gelatin, 10 units of EcoRI (Nippon Gene) and 10 units of PstI (Nippon Gene). The resulting digest was subjected to 0.8% agarose gel electrophoresis and then to the glass powder method to separate and purify a DNA fragment of about 490 bp which corresponds to a 5'-end EcoRI-PstI fragment of the PDI cDNA Separately from this, about 1 µg of pHPDIp4 DNA was digested at 37° C. for 1 hour in 20 µl of the digestion solution consisting of 10 mM Tris-HCl (pH 7.5), 100 mM NaCl, 6 mM MgCl$_2$, 6 mM mercaptoethanol, 0.1% gelatin, 10 units of PstI (Nippon Gene) and 10 units of BamHI (Nippon Gene). The resulting digest was treated in the same manner as described above to separate and purify a DNA fragment of about 1.3 kb which corresponds to a 3'-end PstI-BamHI fragment of the PDI cDNA. The thus recovered two DNA fragments (about 50 ng for each) were ligated with about 20 ng of plasmid vector pUC 119 which has been digested in a linear form with EcoRI and BamHI, by incubating these DNA samples at 16° C. for 15 hours in the mixture of 25 µl of Liquid A and 5 µl of Liquid B of the DNA ligation kit (Takara Shuzo). With 10 µl of the reaction mixture obtained, a competent E. coli strain MV1190 cell was transformed by the calcium chloride technique. The transformed cell was cultured overnight at 37° C. on an X-Gal plate (LB medium containing 1.5% agar further supplemented with 50 µg/ml of 5-bromo-4-chloro-3-indolyl-β-D-galactopyranoside, 80 µg/ml of isopropyl-β-D-thiogalactopyranoside and 25 µg/ml of ampicillin) of 90 mm in diameter. White colonies grown on the plate were picked up, plasmid DNAs were prepared from the colonies by the alkaline lysis method, and the DNAs were analyzed using restriction enzymes, thereby selecting a transformant which carries a target plasmid. The thus obtained plasmid was named phPDIEB.

Using the plasmid phPDIEB, a NaeI cleavage site was introduced into the boundary region between the PDI signal sequence and the PDI sequence itself on the cDNA by the method of Kunkel (Kunkel, T. A., Proc. Natl. Acad. Sci., U.S.A., vol.82, p.488, 1985). E. coli strain BW313 competent cell was transformed with the phPDIEB DNA by calcium chloride technique. A single colony of the resultant transformant was pre-cultured overnight at 37° C. in 2×YT medium (1.6% Bactotrypton, 0.5% NaCl and 1% Bacto-Yeast Extract) supplemented with 150 µg/ml of ampicillin. One ml of the pre-culture was inoculated into 50 ml of the 2×YT medium supplemented with 150 µg/ml of ampicillin, followed by its culture at 37° C. When turbidity (OD$_{600}$) of the medium reached around 0.3, M13K07 phage (m.o.i.=2) was added to the medium, and the infection was carried out by incubating the mixture at 37° C. for 30 minutes without shaking. To this cell suspension was added kanamycin to a final concentration of 70 µg/ml, followed by culturing at 37° C. for 20 hours with shaking. The obtained culture was subjected to centrifugation, and the supernatant recovered was mixed with 1/5 volume of a solution containing 2.5M NaCl and 20% polyethylene glycol #6000. After stirring, the mixture was left for 15 minutes at room temperature. The precipitate obtained by centrifugation was dissolved in 5 ml of the TE buffer (pH 8.0) consisting of 10 mM Tris-HCl and 1 mM EDTA, mixed with an equal volume of neutral phenol with stirring, and then centrifuged to recover an aqueous layer. To the layer was added an equal volume of chloroform with stirring. The mixture was further subjected to centrifugation to recover an aqueous layer. The aqueous layer was then mixed with 1/10 volume of 3M sodium acetate and 2.5 volume of ethanol. After stirring, the mixture was left for 30 minutes at −80° C. followed by centrifugation in order to recover DNA as precipitate. The DNA was washed with 70% ethanol, dried under a reduced pressure and then dissolved in 100 µl of the TE buffer.

Using the resulting phPDIEB-originated single-stranded DNA containing dU, a desired mutation, i.e., introduction of a NaeI site, was carried out in the following manner:

10 pmol of a synthetic oligonucleotide (5'-CGGGGGCGCCGGCGCGC-3', Takara Shuzo) for use in the introduction of a mutation was incubated at 37° C. for 15 minutes in 10 µl of the phosphorylation solution which consists of 100 mM Tris-HCl (pH 8.0), 10 mM MgCl$_2$, 7 mM dithiothreitol, 1 mM ATP and 10 units of T4 polynucleotide kinase (Takara Shuzo), followed by heating at 70° C. for 10 minutes in order to deactivate the T4 polynucleotide kinase. Separately from this, 0.2 pmol of the above-described phPDIEB-originated single-stranded DNA and 1 µl of an annealing buffer (Site-directed mutagenesis system Mutan™-K, Takara Shuzo) were mixed with sterile water to a final volume of 10 µl. One µl of this solution was mixed with 1 µl of the phosphorylated synthetic oligonucleotide solution obtained above, and the mixture was left at 65° C. for 15 minutes and then at 37° C. for 15 minutes. Thereafter, a complementary chain synthesis was carried out by mixing the reaction mixture with 25 µl of a chain elongation solution (Site-directed mutagenesis system Mutan™-K, Takara Shuzo), 60 units of E. coli DNA ligase (Mutan™-K, Takara Shuzo) and 1 unit of T4 DNA polymerase (Mutan™-K, Takara Shuzo), and by incubating the resulting mixture at 25° C. for 2 hours. The reaction was terminated by adding 3 µl of 0.2M EDTA (pH 8.0) and heating the mixture at 65° C. for 5 minutes. 3 µl of the DNA solution obtained was mixed with 30 µl of a suspension of E. coli strain BMH71-18mutS competent cell, and the cell suspension was left for 30 minutes in an ice bath, for 45 seconds at 42° C. and then for 1 minute in an ice bath. To the cell suspension was then added 300 µl of SOC medium (2% Bacto-trypton, 0.5% yeast extract, 10 mM NaCl, 2.5 mM KCl, 10 mM MgSO$_4$, 10 mM MgCl$_2$ and 20 mM glucose), and the mixture was shaken at 37° C. for 1 hour. 10 µl of M13K07 phage was further added thereto, and the mixture was left for 30 minutes at 37° C. After adding 1 ml of 2×YT medium containing 150 µg/ml of ampicillin and 70 µg/ml of kanamycin to the mixture, the mixture was shaken at 37° C. for 20 hours. The resulting culture was centrifuged to recover 20 µl of supernatant which was subsequently mixed with 80 µl of a culture of E. coli strain MV1190. After incubation at 37° C. for 10 minutes, the resulting mixture was inoculated onto a LB plate supplemented with 150 µg/ml of ampicillin and cultured overnight at 37° C. Among colonies grown on the plate, a transformant carrying a NaeI site-introduced plasmid was identified by DNA-sequencing using M13 SEQUENCING KIT (Toyobo). This plasmid was named phPDINae.

2 µg of the phPDINae DNA prepared by the alkaline lysis method was digested at 37° C. for 4 hours in 30 µl of the digestion solution consisting of 10 mM Tris-HCl (pH 8.0), 20 mM NaCl, 7 mM MgCl$_2$, 7 units of NaeI (Nippon Gene) and 10 units of HindIII (Takara Shuzo). The resulting digest was subjected to 0.8% agarose gel electrophoresis and then treated by the glass powder technique so as to separate and purify a DNA fragment of about 1.7 kb.

A plasmid, pUC119Sig, containing a DNA fragment which encodes a human serum albumin prepro-sequence and is composed of codons often utilized in yeast was constructed in the following manner (FIG. 1):

One µg of plasmid vector pUC119 DNA was digested at 37° C. for 1 hour in 20 µl of the digestion solution which consists of 100 mM Tris-HCl (pH 7.5), 10 mM MgCl$_2$, 50 mM NaCl and 12 units of EcoRI (Nippon Gene), followed by heating at 70° C. for 5 minutes in order to deactivate the enzyme. To the reaction mixture was added 38 µl of sterile water and 1 unit of bacterial alkaline phosphatase (Takara Shuzo), and the mixture was incubated at 37° C. for 1 hour, followed by phenol extraction and ethanol precipitation to recover DNA. The DNA was then incubated overnight at 16° C. in 30 µl of the ligation solution which consisted of 66 mM Tris-HCl (pH 7.5), 6.6 mM MgCl$_2$, 10 mM dithiothreitol, 0.1 mM ATP and 300 units of T4 DNA ligase (Takara Shuzo), together with an equal molar amount of a XhoI linker containing a XhoI site and consisting of the following sequence:

| | |
|---|---|
| 5'-AATTCTCGAG | (SEQ ID NO: 19) |
| GAGCTCTTAA-5'. | (SEQ ID NO: 20) |

Using 10 µl of this solution, transformation of *E. coli* JM107 competent cell was carried out by the calcium chloride method. The transformed cell was cultured overnight at 37° C. on a LB plate supplemented with 50 µg/ml of ampicillin. Plasmid DNAs were prepared by the alkaline lysis method from the colonies on the plate and analyzed using restriction enzymes. In this way, a plasmid DNA molecule in which the XhoI linker has been inserted into pUC119 EcoRI site was selected.

The following four types of oligonucleotides:

(1) 5'-TCGAGAATTCATGAAGTGGGTTACCT-TCATCTCTTTGTTGTT-3' (SEQ ID NO:21);
(2) 5'-AACAAGAACAACAAAGAGATGAAGG-TAACCCACTTCATGAATTC-3' (SEQ ID NO:22);
(3) 5'-CTTGTTCTCTTCTGCTTACTCTAGAGGT-GTTTTCAGAAGGCCTG-3' (SEQ ID NO:23); and
(4) 5'-GATCCAGGCCTTCTGAAAACACCTCTA-GAGTAAGCAGAAGAG-3' (SEQ ID NO:24)

were synthesized using an automatic DNA synthesizer (380B, Applied Biosystems).

Each 5'-end of these oligonucleotides was phosphorylated by incubating about 30 pmol of each sample at 37° C. for 1 hour in the solution consisting of 50 mM Tris-HCl (pH 7.6), 10 mM MgCl$_2$, 5 mM dithiothreitol, 0.2 mM ATP and 6 units of T4 polynucleotide kinase (Takara Shuzo). The oligonucleotide solutions obtained were combined (100 µl in total volume) and annealed by leaving the combined solution for 5 minutes in a water bath of 100° C. followed by cooling down to room temperature. To the solution was then added 600 units of T4 DNA ligase (Takara Shuzo), and the mixture was left overnight at 16° C. to ligate these fragments. The double-stranded DNA preparation thus obtained was subjected to phenol extraction in order to remove proteins, and then to ethanol precipitation to recover the DNA.

One µg of the above XhoI linker-introducing vector plasmid was digested at 37° C. for 1 hour in 20 µl of the digestion solution consisting of 100 mM Tris-HCl (pH 7.5), 10 mM MgCl$_2$, 100 mM NaCl, 10 units of BamHI (Nippon Gene) and 12 units of XhoI (Takara Shuzo), followed by phenol extraction and ethanol precipitation to recover a DNA fragment. The fragment obtained was incubated overnight at 16° C. in 30 µl of the ligation solution which consists of 66 mM Tris-HCl (pH 7.5), 6.6 mM MgCl$_2$, 10 mM dithiothreitol, 0.1 mM ATP and 300 units of T4 DNA ligase (Takara Shuzo), together with an equal molar amount of the double-stranded DNA fragment obtained by ligating the four oligonucleotides. Using 10 µl of the thus prepared solution, transformation of *E. coli* JM107 competent cells was carried out by the calcium chloride method. The transformed cells were cultured overnight at 37° C. on LB medium containing 50 µg/ml of ampicillin. Plasmid DNAs prepared from colonies on the plate were analyzed using restriction enzymes so as to select a transformant containing a desired recombinant plasmid. The obtained plasmid was named pUC119Sig.

A DNA was prepared from plasmid pUC119Sig by the alkaline lysis method. 2 µg of the DNA was digested at 37° C. for 4 hours in the digestion solution which consists of 10 mM Tris-HCl (pH 8.0), 100 mM NaCl, 7 mM MgCl$_2$, 8 units of StuI (Nippon Gene) and 10 units of HindIII (Takara Shuzo), subjected to 0.8% agarose gel electrophoresis and then treated by the glass powder technique to separate and purify a DNA fragment of about 3.2 kb. The 1.7 kb DNA fragment (about 50 ng) derived from phPDINae was reacted with the 3.2 kb DNA fragment (about 50 ng) from pUC119Sig at 16° C. for 30 minutes in the ligation kit solution of Takara Shuzo(Japan) (a mixture of Liquid A 30 µl+Liquid B 6 µl ). Using 10 µl of its reaction mixture, transformation of *E. coli* HB101 competent cells (Takara Shuzo) was carried out by the calcium chloride method. The transformed cells were cultured overnight at 37° C. on a LB plate supplemented with 50 µg/ml of ampicillin. Plasmid DNAs were prepared by the alkaline lysis method from colonies grown on the plate and analyzed using restriction enzymes to select a recombinant plasmid in which the human PDI itself was linked to the downstream side of the human serum albumin prepro-sequence (FIG. 2). The obtained plasmid was named phPDILyl.

A human PDI expression plasmid was constructed in the following manner, such that the leader sequence modified type PDI can express under the control of a promoter of yeast alcohol dehydrogenase I gene:

7 µl of phPDILyl DNA prepared by the alkaline lysis method was digested at 37° C. for 2 hours in 100 µl of the digestion solution which consists of 100 mM Tris-HCl (pH 8.0), 100 mM NaCl, 7 mM MgCl$_2$ and 40 units of EcoRI (Nippon Gene). The resulting solution was mixed with an equal volume of a phenol/chloroform mixture (a mixture of saturated phenol with an equal volume of chloroform). After stirring, the mixture was centrifuged to recover an aqueous layer. The phenol/chloroform extraction was repeated, and the aqueous layer obtained was mixed with 1/10 volume of 3M sodium acetate (pH 5.3) and 2.5 volume of ethanol. The mixture was left for 2 hours at −40° C. and then subjected to centrifugation. The pellet was washed with 70% ethanol, dried under a reduced pressure and then dissolved in 50 µl of Klenow buffer solution (Deletion Kit for Kilo-Sequence, Takara Shuzo). Thereafter, to the solution obtained was added 4 units of Klenow fragment (Takara Shuzo), and the mixture was incubated at 37° C. for 45 minutes to blunt-end the EcoRI cleavage site. The thus prepared solution was subjected twice to phenol/chloroform extraction, and the resulting aqueous layer was mixed with 1/10 volume of 3M sodium acetate (pH 5.3) and 2.5 volume of ethanol. The mixture was left for 1 hour at −40° C. and then subjected to centrifugation. The pellet was washed with 70% ethanol, dried under a reduced pressure and then dissolved in 50 µl of Klenow buffer solution (Deletion Kit for Kilo-Sequence, Takara Shuzo). Thereafter, to the solution obtained was added 4 units of Klenow fragment (Takara Shuzo), and the mixture was incubated at 7° C. for 45 minutes to blunt the EcoRI cleavage site. The reaction mixture was then subjected twice to phenol/chloroform extraction, and the resulting aqueous layer was mixed with 1/10 volume of 3M sodium acetate (pH 5.3) and 2.5 volume of ethanol. The mixture was left for 1 hour at −40° C. and then centrifuged. The pellet was washed with 70% ethanol, dried under a reduced pressure and then dissolved in 40 µl of the solution which consists of 10 mM Tris-HCl (pH 8.0), 60 mM NaCl, 7 mM MgCl$_2$ and 10 units of BamHI (Nippon Gene). Thereafter, the DNA solution obtained was subjected to 0.8% agarose gel electrophoresis and then treated by the glass powder technique so as to separate and purify a DNA fragment of about 1.8 kb. Separately from this, 5 µl of pJDB-ADH-HSA-A DNA (Japanese Patent Application Laying-Open (KOKAI) No. 2-117384) prepared by the alkaline lysis method was digested at 37° C. for 2 hours in 100 µl of the digestion solution which consists of 10 mM Tris-HCl (pH 8.0), 100 mM NaCl, 7 mM MgCl$_2$ and 24 units of XhoI (Takara Shuzo). The reaction mixture was then subjected twice to phenol/chloroform extraction, and the aqueous layer separated was mixed with 1/10 volume of 3M sodium acetate (pH 5.3) and 2.5 volume of ethanol. The mixture was left for 2 hours at −40° C. and then centrifuged to recover DNA as precipitate. The DNA precipitate was washed with 70% ethanol, dried under a reduced pressure and then dissolved in 50 µl of Klenow buffer solution (Deletion Kit for Kilo-Sequence, Takara Shuzo). Thereafter, to the solution obtained was added 4 units of Klenow fragment (Takara Shuzo), and the mixture was incubated at 37° C. for 45 minutes to blunt the XhoI cleavage site. The reaction mixture was then subjected twice to phenol/chloroform extraction, and the aqueous layer separated was mixed with 1/10 volume of 3M sodium acetate (pH 5.3) and 2.5 volume of ethanol. This mixture was left for 1 hour at −40° C. before centrifugation. The DNA pellet removed was washed with 70% ethanol, dried under a reduced pressure and then dissolved in 40 µl of the solution which consists of 10 mM Tris-HCl (pH 8.0), 60 mM NaCl, 7 mM MgCl$_2$ and 10 units of BamHI (Nippon Gene). The solution obtained was incubated at 37° C. for 75 minutes to digest the DNA. To the reaction mixture was then added 10 µl of 2M Tris-HCl (pH 8.0), 110 µl of sterile water and 1 unit of alkaline phosphatase from *E. coli* strain C75 (Takara Shuzo), and the mixture was incubated at 60° C. for 1 hour in order to carry out a 5′-end dephosphorylation of the restriction enzyme-formed cleavage site. To the reaction mixture was added 1/10 volume of 3M sodium acetate (pH 5.3) and 2.5 volume of ethanol. The mixture obtained was left for 1 hour at −40° C. before centrifugation. The DNA pellet separated was dried under a reduced pressure and then dissolved in 20 µl of the TE buffer. Thereafter, the prepared DNA solution was subjected to 0.8% agarose gel electrophoresis and then treated by the powder glass technique so as to separate and purify a DNA fragment of about 8 kb. The thus obtained phPDILyl-originated 1.8 kb DNA fragment (about 50 ng) and PJDB-ADH-HSA-A-originated 8 kb DNA fragment (about 50 ng) were incubated at 16° C. for 2.5 hours in the DNA ligation kit solution of Takara Shuzo (a mixture of Liquid A 30 µl+Liquid B 6 µl ) in order to ligate the two DNA fragments. Using 10 µl of the prepared DNA solution, transformation of *E. coli* strain C600 was carried out by the calcium chloride technique. The transformed cells were cultured overnight at 37° C. on a LB plate supplemented with 50 µg/ml of ampicillin. Plasmid DNAs were prepared by the alkaline lysis method from colonies grown on the plate and analyzed using restriction enzymes in order to select a transformant carrying a plasmid in which the leader sequence modified type PDI sequence was linked to the downstream side of the alcohol dehydrogenase I promoter. The constructed PDI expression plasmid was named pAH-hPDILyl. As the results of the plasmid construction, the N-terminal amino acid of the mature PDI protein was changed from Asp to Gly.

A control plasmid for use in experiments of the human PDI expression was constructed in the following manner:

5 µl of pJDB-ADH-HSA-A DNA prepared by the alkaline lysis method was digested at 37° C. for 2 hours in 100 µl of the digestion solution which consists of 10 mM Tris-HCl, 100 mM NaCl, 7 mM MgCl$_2$, 24 units of XhoI (Takara Shuzod) and 29 units of BamHI (Nippon Gene). The reaction mixture obtained was subjected twice to phenol/chloroform extraction, and to the aqueous layer was added 1/10 vol of 3M sodium acetate (pH 5.3) and 2.5 vol of ethanol. The mixture obtained was then left for 2 hours at −40° C. and then centrifuged to recover DNA as pellet. The DNA pellet was washed with 70% ethanol, dried under a reduced pressure and then dissolved in 50 µl of Klenow buffer solution (Deletion Kit for Kilo-Sequence, Takara Shuzo). Thereafter, to the obtained solution was added a 4 units of Klenow fragment (Takara Shuzo), and the mixture was incubated at 37° C. for 45 minutes ho blunt the XhoI and BamHI cleavage sites. The reaction mixture was then subjected twice to phenol/chloroform extraction, and the aqueous layer separated was mixed with 1/10 vol of 3M sodium acetate (pH 5.3) and 2.5 vol of ethanol. The mixture was left for 1 hour at −40° C. before centrifugation. The DNA pellet removed was dried under a reduced pressure and dissolved in 20 µl of the TE buffer. Thereafter, the DNA solution was subjected to 0.8% agarose gel electrophoresis and then treated by the glass powder technique to separate and purify a DNA fragment of about 8 kb. The thus obtained DNA fragment (about 50 ng) was mixed with the mixture of Liquid A 30 µl+Liquid B 6 µl from the DNA ligation kit (Takara Shuzo), and incubated overnight at 16° C. so as to cyclize it by self-ligation. Using 10 µl of the prepared DNA solution, transformation of *E. coli* 101 competent cells (Takara Shuzo) was carried out by the calcium chloride technique. The transformed cells were cultured overnight at 37° C. on a LB plate supplemented with 50 µg/ml of ampicillin. Plasmid DNAs were prepared by the alkaline lysis technique from the colonies grown on the plate, and analyzed using restriction enzymes in order to select a desired control plasmid. The constructed plasmid was named pAH.

Expression of human PDI in yeast

Figure 3:
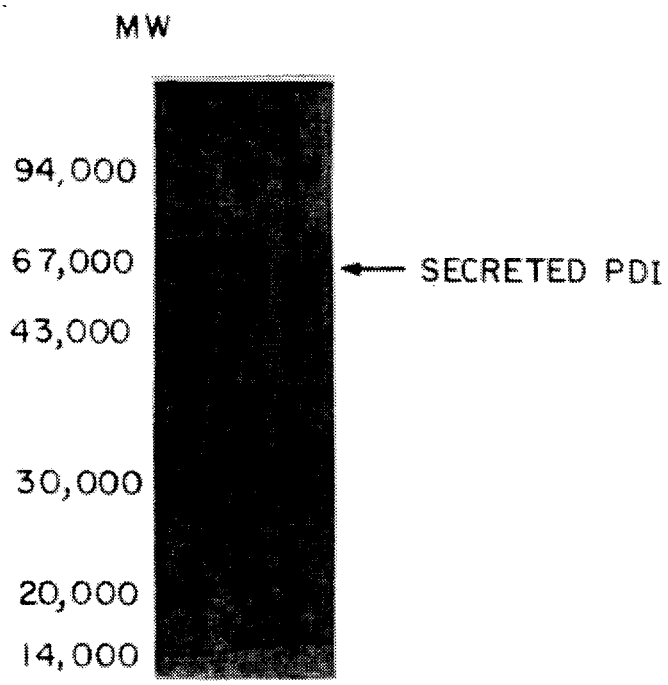
FIG. 3 is a photograph showing the result of SDS-polyacrylamide gel electrophoresis of an expressed and secreted crude recombinant human PDI, wherein lane 1 is a molecular weight marker, lane 2 is pAH/AH22 (control) and lane 3 is pAHhPDILyl/AH22.
Figure 5:
FIG. 5 shows the result of SDS-polyacrylamide gel electrophoresis of a purified recombinant human PDI, wherein the numbers at the bottom correspond to the fraction numbers of the hydrophobic column chromatography shown in FIG. 4, and M is a molecular weight marker.

Using the human PDI expression plasmid pAHhPDILyl constructed above, an expression of human PDI in yeast was carried out in the following manner:

A single colony of yeast strain AH22 obtained by culturing it on a YPD plate (2% Bacto-pepton, 1% yeast extract, 2% glucose and 1.5% agar) was inoculated into 5 µl of a YPD medium (2% Bactopepton, 1% yeast extract and 2% glucose) and cultured at 30° C. for 24 hours with shaking. This pre-culture (0.9 ml) was then inoculated into 45 ml of the YPD medium and cultured at 30° C. with shaking. When turbidity at OD$_{600}$ reached about 0.5, the main culture was subjected to a low speed centrifugation to recover yeast cells as precipitate. The cells removed were suspended in 3 ml of 0.2M LiSCN, and the cell suspension (1 ml) was centrifuged to recover the cells. To the cells were subsequently added 46 µl of 50% PEG #4000, 10 µl of LiSCN and 10 µl of a pAHhPDILyl DNA solution (27 µg as DNA) prepared by the alkaline lysis method. After mixing them by pipetting, the mixture was left overnight at 30° C. followed by its suspension in 1 ml of sterile water. The suspension was then centrifuged to recover cells as pellet. The pellet was resuspended in 100 µl of sterile water and cultured at 30° C. after the inoculation of its suspension onto a SD(-Leu) plate (SD(-Leu) medium (0.67% Bacto-nitrogen base, 2% glucose, 20 mg/l of adenine, 20 mg/l of uracil, 20 mg/l of tryptophan, 20 mg/l of histidine, 20 mg/l of arginine, 20 mg/l of methionine, 30 mg/l of tyrosine, 30 mg/l of isoleucine, 30 mg/l of lysine, 50 mg/l of phenylalanine, 100 mg/l of aspartic acid, 100 mg/l of glutamic acid, 150 mg/l of valine, 200 mg/l of threonine and 375 mg/l of serine (amino acids from Wako Pure Chemical Industries, Japan))+1.5% agar). A transformant from the 5-days culture was inoculated into 5ml of the SD (-Leu) medium and cultured at 30° C. for 2 days with shaking. 100 µl of the obtained pre-culture was then inoculated into 5 ml of the YPD medium and cultured at 30° C. for 24 hours with shaking. 1.5 ml of the resulting main culture was centrifuged to recover 500 µl of supernatant which was subsequently mixed with the equal volume of ethanol and then left for 1 hour in an ice bath. The mixture was centrifuged so as to recover products secreted out of the yeast cells as a pellet which was then dried under a reduced pressure. The pellet was dissolved in 10 µl of a sample buffer for SDS-PAGE (125 mM Tris-HCl (pH 6.8), 4% SDS, 20% glycerol, 10% β-mercaptoethanol and 0.01% Bromophenol Blue). After boiling for 5 minutes, the treated sample was subjected to electrophoresis on SDS/PAGE Plate 10/20 (Daiichi Kagaku Yakuhin, Japan). The resulting gel was stained with a staining solution (0.15% Coomassie Brilliant Blue, 10% acetic acid and 40% methanol) and then soaked in a decoloring solution (10% acetic acid and 40% methanol) to visualize an expressed product. In this instance, a control sample obtained by the same procedure, except that pAHhPDILyl was replaced by the aforementioned control plasmid pAH, was run at the same time during the electrophoresis. As standard molecular weight markers, phosphorylase b (molecular weight, 94,000), bovine serum albumin (67,000), ovalbumin (43,000), carbonic anhydrase (30,000), soybean trypsin inhibitor (20,000) and α-lactalbumin (14,000) were used (FIG. 3). As the results, an expression product having a molecular weight of about 55K was found. Since this molecular weight coincided with that of the mature PDI protein, it was assumed that a desired human PDI was expressed and secreted. Next, a large-scale culture was carried out in the following manner in order to examine chemical properties of the expressed and secreted protein:

A single colony of the pAHhPDILyl-carrying yeast strain AH22 was inoculated into 80 ml of the SD (-Leu) medium and cultured at 30° C. for 2 days with shaking. The obtained pre-culture was then inoculated into 4 liters of a YPD-phosphate medium (YPD medium, 6 g/l of $Na_2HPO_4$, and 3 g/l of $KH_2PO_4$, pH 7.0) and cultured at 30° C. for 24 hours with shaking. The resulting main culture was centrifuged to removed the supernatant which was used for the purification of the secreted expression product.
Isolation of recombinant human PDI from the culture and its characterization The culture (4 liters) obtained by culturing the recombinant yeast was concentrated to 1/40 (final volume, 100 ml) using a Millipore-Millitan ultrafiltration apparatus (nominal molecular weight, 30,000 cut-off), and then subjected to TSK-gel Phenyl-5PW hydrophobic column chromatography so as to isolate human PDI. The elution was carried out in 10 mM borate-10 mM KCl buffer (pH 8.0) containing 0.05% $NAN_3$, with a linear gradient from 0.85M to 0M of ammonium sulfate over 125 minutes. The flow rate was 2 ml/min. The result is shown in FIG. 4. In FIG. 5 the result of SDS-electrophoresis of the isolated human PDI is illustrated. As shown in the figures, the human PDI was purified almost homogeneously by the hydrophobic column chromatography without a loss of its activity. Any UV-absorbing substance in the YPD medium could be removed markedly efficiently by the chromatography.
PDI assaX PDI assay was carried out by measuring its effect to enhance the refolding of scrambled ribonuclease A (RNase A) which has been prepared by reduction, denaturation and re-oxidation steps. Refolding degree of the scrambled RNase A was determined by measuring a degree of the restoration of its enzyme activity. The following describes the assay procedure illustratively:
(A) Preparation of scrambled RNase A:

120 mg of RNase A was dissolved in 3 ml of 0.1M Tris-HCl buffer (pH 8.6) containing 6M guanidine hydrochloride and 0.15M dithiothreitol, and then reduced under nitrogen atmosphere at room temperature for 15 hours. The reduced product was applied to a Sephadex G-25 column (15 mmø×38 cm) equilibrated with 0.01N HCl, thereby removing the reducing agent. To the desalting product was added guanidine hydrochloride to a final concentration of 6M. After adjusting its pH value to 9.0 with Tris, the mixture was subjected to an exchange reaction of a S—S bond(s) in the dark at 4° C. for 14 days. The thus prepared sample was stored at −80° C. for use as the scrambled RNase A.
(B) PDI assay:

10 µl of 1M dithiothreitol is added to 20 ml of 55 mM phosphate buffer (pH 7.5) in which any dissolving air was replaced with nitrogen gas. 10 µl of this solution is added to 420 µl of 55 mM phosphate buffer (pH 7.5) mixed with 20 µl of an enzyme sample, and the mixture is left for 5.5 minutes at 30° C. To this solution is added 50 µl of the scrambled RNase A solution prepared above, followed by the enzymatic reaction at 30° C. for 15.5 minutes. Separately from this, 1.945 ml of degassed 50 mM Tris-HCl buffer (pH 7.5) containing 5 mM $MgCl_2$, 25 mM KCl and 50 µl of a yeast RNA solution (dissolved in 10 mM Tris-HCl buffer, pH 7.5, containing 1 mM EDTA; adjusted to such a concentration that absorbance at 280 nm becomes 80) is placed into a quartz cell (1 cm×1 cm). With stirring, a temperature of the resulting mixture is maintained at 45° C. In this instance, absorbance at 260 nm should not be changed by the treatment. Thereafter, 5 µl of the dithiothreitol-treated scrambled RNase A solution is added to the buffer in the quartz cell and, with stirring, a change in the absorbance of the reaction mixture at 260 nm are measured over 2 minutes at 0.2 minute intervals. The PDI activity is calculated from an initial velocity of the changing rate of absorbance at 260 nm.

EXAMPLE 2

Transformation of yeast strain HIS23 with human PDI expression plasmid pAHhPDILyl Using the aforementioned human PDI expression plasmid pAHhPDILyl, transformation of the HSA-producing yeast strain HIS23 (Japanese Patent Application No. 2-57885 filed by the present applicant, Bikoken-Kin-Ki No. 11351 (FERM P-1138)) was carried out in the following manner:

A single colony of the HSA-expressing yeast strain HIS23 obtained by culturing it on a YPD plate (2% Bacto-trypton, 1% Bactoyeast extracts, 2% glucose and 1.5% agar) was inoculated into 5 ml of a YPD medium (2% Bacto-trypton, 1% yeast extract and 2% glucose) and cultured at 30° C. for 24 hours with shaking. One ml of the obtained pre-culture was inoculated into 50 ml of the YPD medium and cultured at 30° C. with shaking. When turbidity at $OD_{600}$ reached about 0.5, the main culture was subjected to a low speed centrifugation to recover the yeast cells as pellet. To the pellet were added 46 µl of 50% polyethylene glycol #4000, 10 µl of LiSCN and 10 µl of the human PDI expression plasmid pAHhPDILyl DNA solution (about 20 µg as DNA) prepared by the alkaline lysis method (Birnboim, H. C. and Doly, J., *Nucleic Acids Res.*, vol.7, p.1513, 1979). After mixing them by pipetting, the mixture was left overnight at 30° C. The resulting mixture was suspended in 1 ml of sterile water and centrifuged to recover cells as pellet. The pellet was suspended in 100 μl of sterile water and cultured at 30° C. after inoculating the cell suspension onto a SD (-His,-Leu) plate (0.67% Bacto-nitrogen base, 2% glucose, 20 mg/l of adenine, 20 mg/l of uracil, 20 mg/l of tryptophan, 20 mg/l of arginine, 20 mg/l of methionine, 30 mg/l of tyrosine, 30 mg/l of isoleucine, 30 mg/l of lysine, 50 mg/l of phenylalanine, 100 mg/l of aspartic acid, 100 mg/l of glutamic acid, 150 mg/l of valine, 200 mg/l of threonine and 375 mg/l of serine (amino acids from Wako Pure Chemical Industries))+ 1.5% agar). A transformant was obtained as a colony grown on the plate on the day 5 after the culture.

Figure 6:
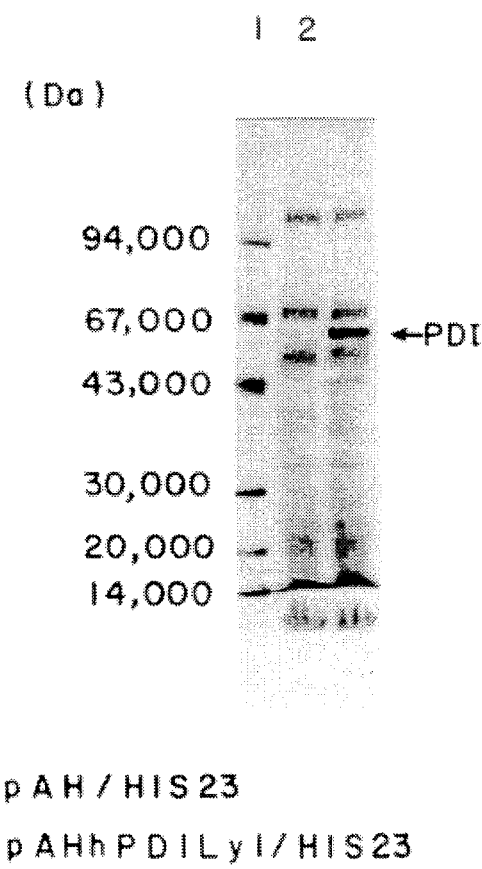
FIG. 6 is a photograph of SDS electrophoresis showing expression of human PDI in the yeast strain HIS23.

Expression of PDI in the obtained transformant (pAHhPDILyl/HIS23) was examined in the following manner:

In this instance, a transformant (pAH/HIS23) obtained using the plasmid pAH which has been prepared by removing the PDI cDNA moiety from pAHhPDILyl was used as a control. The single colony grown on the plate was inoculated into 5 ml of the SD (-His, -Leu) medium and cultured at 30° C. for 2 days with shaking. 100 μl of the pre-culture was then inoculated into 5 ml of the YPD medium and cultured at 30° C. for 24 hours with shaking. 1.5 ml of the resulting main culture was centrifuged to recover 500 μl of supernatant which was subsequently mixed with the equal volume of ethanol and then left for 1 hour in an ice bath. The mixture was centrifuged to recover products secreted out of the yeast cells as a precipitate which was then dried under a reduced pressure using an evaporator. The precipitate was dissolved in 10 μl of a sample buffer for SDS-PAGE (62.5 mM Tris-HCl (pH 6.8), 2% SDS, 5% β-mercaptoethanol, 0.005% Bromophenol Blue and 20% glycerol). After boiling for 5 minutes, the sample was subjected to electrophoresis on SDS-PAGE Plate 4/20-1010 (Daiichi Kagaku Yakuhin). The resulting gel was stained with a staining solution (0.15% Coomassie Brilliant Blue, 10% acetic acid and 40% methanol) and then soaked in a decoloring solution (10% acetic acid and 40% methanol) to visualize an expressed product. In this instance, phosphorylase b (molecular weight, 94,000 daltons), bovine serum albumin (67,000), ovalbumin (43,000), carbonic anhydrase (30,000), soybean trypsin inhibitor (20,000) and α-lactalbumin (14,000) were used as standard molecular weight markers (FIG. 6). As the results, the secretion of an expressed PDI having a molecular weight of about 55,000 daltons was detected in the yeast strain HIS23 transformed with pAHhPDILyl.

Effect Of human PDI on the expression and secretion of HSA

Figure 7:
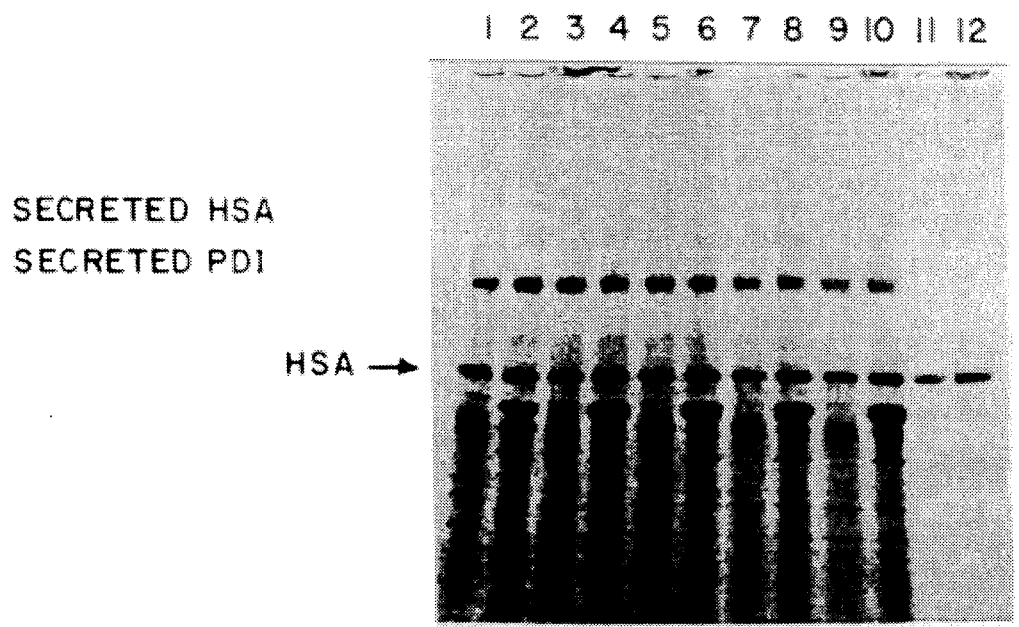
FIG. 7 is a photograph of SDS-polyacrylamide gel electrophoresis showing secretion of HSA by co-expression of human PDI and HSA in the yeast strain HIS23.

Using the above-described co-expression system of HSA and PDI in a yeast cell, effects of human PDI on the expression and secretion of HSA were examined in the following manner:

Five single colonies were isolated from strain pAH/HIS23 which has been obtained by transforming the yeast strain HIS23 with the control plasmid pAH, and other 5 single colonies were isolated from strain pAHhPDILyl/HIS23 obtained by transforming the HIS23 with the human PDI expression plasmid pAHhPDILyl. Each of the thus isolated single colonies was inoculated into 5 ml of the SD (-His, -Leu) medium and cultured at 30° C. for 24 hours. Each of the pre-cultures (100 μl) was inoculated into 5 ml of the YPD medium and cultured at 30° C. for 24 hours with shaking. From the main cultures obtained, samples for SDS-PAGE were prepared in accordance with the aforementioned procedure. Results of the SDS-PAGE are shown in FIG. 7. Using the gels subjected to the SDS-PAGE, the amount of secreted HSA from each strain was determined using a densitometer (IMAGE ANALYSIS SYSTEM, TEFCO, Japan) in order to examine effects of the co-expression of PDI on the secreted amount of expressed HSA (FIG. 8). As shown in the figure, the strains pAH/HIS23 and pAHhPDILyl secreted HSA in average amounts of 0.93 mg/l and 1.50 mg/l, respectively. In other words, secretion of HSA was increased by about 60% in average due to the co-expression of PDI in the yeast strain HIS23.

EXAMPLE 3

Cloning of yeast ERD2 gene

Cloning of yeast ERD2 gene was carried out through the polymerase chain reaction (PCR) technique (Mullis, K. B. and Faloona, F., *Meth. Enzymol.*, vol.155, p.335, 1987) as follows:

A single colony of yeast strain S288C was inoculated into 2 ml of YPD medium (2% Bacto-trypton, 1% Bacto-yeast extracts and 2% glucose) and cultured at 30° C. for24 hours. Yeast cells recovered by centrifugation from the culture were washed with 1 ml of a sorbitol solution (1M sorbitol and 50 mM $K_2HPO_4/KH_2PO_4$, pH 6.85) and then subjected again to centrifugation. The cells collected were suspended in 1 ml of the sorbitol solution, and the cell suspension was mixed with 40 μl of Zymolyase solution (10 mg/ml) and 1 μl of β-mercaptoethanol, and maintained at 37° C. for 30 minutes. Next, cells recovered by centrifugation were suspended in 200 μl of 50 mM Tris-HCl (pH 7.5) containing 20 mM EDTA, and to the cell suspension was added 200 μl of an NDS buffer solution (0.5M EDTA, 10 mM Tris-HCl (pH 7.5), 1% sodium dodecyl sarcosinate, 7.5% β-mercaptoethanol and 1 mg/ml of Pronase K). After incubation at 50° C. for 1 hour, the mixture was extracted with a phenol/chloroform solution, and to the aqueous layer separated was added 1/10 vol of 3M sodium acetate (pH 5.2) and 2.5 vol of ethanol. After cooling at −80° C. for 20 minutes, the precipitate obtained by ethanol precipitation was recovered by centrifugation. The precipitat was dissolved in 400 μl of TE buffer (10 mM Tris-HCl, pH 8.0, and 1 mM EDTA), and the solution was mixed with 240 μl of 20% PEG solution (20% polyethylene glycol and 2.5M NaCl). After cooling for 1 hour in an ice bath, the precipitate was recovered by centrifugation which was subsequently washed with 70% ethanol and dissolved in 400 μl of the TE buffer. The solution obtained was extracted twice with phenol/chloroform, and a genomic DNA of the yeast strain S288C was recovered by ethanol precipitation of the separated aqueous layer.

Using the thus obtained genomic DNA as a template, cloning of the yeast ERD2 gene was carried out.

A reaction mixture for PCR reaction was prepared by mixing together 10 μl of S228C genomic DNA (0.02 μg), 5 μl of primer I (0.25 μg), 5 μl of primer II (0.25 μg), 0.5 μl of TaqI polymerase (Gene Amp™ DNA Amplification Reagent Kit, Perkin Elmer Cetus), 10 μl of the reaction buffer concentrated to 1/10 (the same kit just described), dNTP mixture (1.25 mM for each, the same kit just described) and 53.5 μl of sterile water. A PCR reaction was carried out in the mixture using a DNA Thermal Cycler (Perkin Elmer Cetus). The reaction conditions employed are: denaturation of DNA, 94° C. for 1 minute; annealing, 50° C. for 2 minutes; and polymerase chain elongation reaction, 72° C. for 3 minutes. After 30 cycles of the reaction steps, the final reaction was carried out at 72° C. for 7 minutes. The primers I and II have the following sequences:

primer I: (SEQ ID NO: 16)
5'-TTTTTCTCGAGTAAGCAATGAATCCGTT-3';
and
primer II: (SEQ ID NO: 17)
5'-AAAAAGGATCCTGCGAACACTATTTAAA-3'.

The reaction mixture obtained was extracted with phenol/chloroform, and the aqueous layer separated was subjected to ethanol precipitation to recover DNA. The DNA was incubated at 37° C. for 2 hours in 20 μl of the digestion solution which consists of 10 mM Tris-HCl (pH 8.0), 100 mM NaCl, 7 mM MgCl$_2$, 5 units of XhoI (Takara Shuzo) and 5 units of BamHI (Takara Shuzo). After the reaction, the digest was. subjected to 0.8% agarose gel electrophoresis and then treated by the glass powder technique (Gene Clean™, Bio-101) to separate and purify a DNA fragment of about 0.7 kb. About 50 ng of the recovered DNA fragment and about 20 ng of a plasmid vector BluescriptII SK+ which has been digested with XhoI and BamHI were mixed with a ligation solution (Liquid A 30 μl+ Liquid B 6 μl from the DNA ligation kit, Takara Shuzo), and the mixture was incubated at 16° C. for 2 hours so as to ligate the DNA fragment with the plasmid vector. Using the obtained recombinant plasmid (named pYERD2, FIG. 9), transformation of E. coli strain XL1-Blue was carried out.

The DNA fragment thus subcloned was further subcloned into small fragments before its DNA sequencing. As the results, it was confirmed that the DNA fragment contained the yeast ERD2 gene. The base sequence and deduced amino acid sequence coincided with those reported by Semenza et al. (Semenza, J. C., Hardwick, K. G., Dean, N. and Pelham, H. R. B., *Cell,* vol.61, p.1349, 1990), except that the reported codon for the Leu of position 52 was "TTG" while that of the clone of this invention was "TTA".

Construction of vector for use in the integration of ERD2 expression unit into yeast chromosome TRP1 site A vector for use in the integration of ERD2 expression unit into yeast chromosome was constructed using the aforementioned plasmid pYERD2 by the following procedure (FIGS. 9 to 11):

0.5 μg of the plasmid vector pRS304 DNA (Sikorski, R. S. and Hieter, P., *Genetics,* vol.122, p.1, 1989) prepared by the alkaline lysis method (Birnboim, H. C. and Doly, J., *Nucleic Acids Res.,* vol.7, p.1513, 1979) was digested at 37° C. for 2 hours in 30 μl of a digestion solution which consists of 10 mM Tris-HCl (pH 8.0), 100 mM NaCl, 7 mM MgCl$_2$, 5 units of XhoI (Takara Shuzo) and 5 units of BamHI (Takara Shuzo). The resulting digest was subjected to 0.7% agarose gel electrophoresis and then treated by the glass powder technique to separate and purify a DNA fragment of about 4.3 kb. Separately from this, 0.5 μg of the ADH I transcription terminator cassette vector pUC-ATE DNA (Japanese Patent Application Laying-Open (KOKAI) No. 2-117384 filed by the present applicant) was digested at 37° C. for 2 hours in 30 μl of the digestion solution which consists of 10 mM Tris-HCl (pH 8.0), 150 mM NaCl, 7 mM MgCl$_2$, 5 units of SalI (Takara Shuzo) and 5 units of BamHI (Takara Shuzo). The resulting digest was subjected to 1% agarose gel electrophoresis and then treated by the glass powder technique to separate and purify a DNA fragment of about 0.4 kb. The thus recovered DNA fragments (about 50 ng for each) were mixed with a ligation solution (Liquid A 30 μl Liquid B 6 μl from the DNA ligation kit, Takara Shuzo), and incubated at 16° C. for 2 hours to ligate and cyclize the DNA fragments. With the obtained recombinant plasmid (named pRS304ATE), the E. coli strain XL1-Blue was transformed.

Next, 0.5 μg of the HSA expression vector pRG-UAS1-N7-TLY1-305 DNA (Japanese Patent Application No. 3-188794 filed by the present applicant) was digested at 37° C. for 2 hours in 30 μl of the digestion solution which consists of 10 mM Tris-HCl (pH 8.0), 100 mM NaCl, 7 mM MgCl$_2$, 10 units of NotI (Toyobo) and 5 units of BamHI (Takara Shuzo). The resulting digest was subjected to 0.7% agarose gel electrophoresis and then treated by the glass powder technique to separate and purify a DNA fragment of about 4 kb. Separately from this, 0.5 μg of the pRS304-ATE DNA was digested at 37° C. for 2 hours in 30 μl of the digestion solution which consists of 10 mM Tris-HCl (pH 8.0), 100 mM NaCl, 7 mM MgCl$_2$, 10 units of NotI (Toyobo) and 5 units of BamHI (Takara Shuzo). The resulting digest was subjected to 0.7% agarose gel electrophoresis and then treated by the glass powder technique to separate and purify a DNA fragment of about 5 kb. The thus recovered DNA fragments (about 50 ng for each) were mixed with a ligation solution (Liquid A 30 μl+Liquid B 6 μl from the DNA ligation kit, Takara Shuzo), and incubated at 16° C. for 2 hours to ligate and cyclize the DNA fragments. Using the obtained recombinant plasmid (named pRG-UAS1-N7-TLY1-304), transformation of the E. coli strain XL1-Blue was carried out.

0.5 μg of the aforementioned plasmid pYERD2 DNA prepared by the alkaline lysis method was digested at 37° C. for 2 hours in 30 μl of the digestion solution which consists of 10 mM Tris-HCl (pH 8.0), 100 mM NaCl, 7 mM MgCl$_2$, 5 units of XhoI (Takara Shuzo) and 5 units of BamHI (Takara Shuzo). The resulting digest was subjected to 0.8% agarose gel electrophoresis and then treated by the glass powder technique to separate and purify a DNA fragment of about 0.7 kb. Separately from this, 0.5 μg of the DNA prepared by the alkaline lysis method from the aforementioned human HSA integration vector pRG-U1-N7-TLY-304 was digested at 37° C. for 2 hours in 30 μl of the digestion solution which consists of 10 mM Tris-HCl (pH 8.0), 100 mM NaCl, 7 mM MgCl$_2$, 5 units of XhoI (Takara Shuzo) and 5 units of BamHI (Takara Shuzo). Following 0.8% agarose gel electrophoresis of the resultant digest, a DNA fragment of about 6.3 kb was purified by the glass powder technique. The thus recovered DNA fragments (about 50 ng for each) were mixed with the ligation solution (Liquid A 30 μl+Liquid B 6 μl, Takara Shuzo), and incubated at 16° C. for 2 hours to ligate the DNA fragments. With the obtained recombinant plasmid (named pIVTRPGAPYERD2), the E. coli strain HB101 was transformed.

One μg of the pIVTRPGAPYERD2 DNA prepared by the alkaline lysis method was digested at 37° C. for 4 hours in 30 μl of the digestion solution which consists of 10 mM Tris-HCl (pH 8.0), 100 mM NaCl, 7 mM MgCl$_2$, 5 units of XhoI (Takara Shuzo) and 5 units of HindIII (Takara Shuzo). The resulting digest was subjected to 0.8% agarose gel electrophoresis and then treated by the glass powder technique to separate and purify a DNA fragment of about 6.8 kb. Separately from this, 1 μg of DNA prepared by the alkaline lysis method from the HSA expression vector pJDB-ADH-HSA-A (Japanese Patent Application Laying-Open (KOKAI) No. 2-117384) was digested at 37° C. for 4 hours in 30 μl of the digestion solution which consists of 10 mM Tris-HCl (pH 8.0), 100 mM NaCl, 7 mM MgCl$_2$, 5 units of XhoI (Takara Shuzo) and 5 units of HindIII (Takara Shuzo). The resulting digest was subjected to 0.8% agarose gel electrophoresis and then treated by the glass powder technique to separate and purify a DNA fragment (yeast alcohol dehydrogenase I promoter) of about 1.4 kb. The thus recovered DNA fragments (about 50 ng for each) were mixed with the ligation solution (Liquid A 30 μl+Liquid B 6 μl from the DAN ligation kit, Takara Shuzo), and then incubated at t6° C. for 2 hours so as to ligate the DNA fragments. Using the thus obtained recombinant plasmid (named pIVTRPADHYERD2), transformation of the E. coli strain HB101 was carried out.

Preparation of strain SN35A

The HSA expression-vector pRG-UAS1-N7-TLY1-305 (Japanese Patent Application No. 3-188794) was digested with HindIII and XhoI, and the digest was subjected to 0.7% agarose gel electrophoresis to separate a DNA fragment of about 10 kb which was subsequently purified using Gene Clean. Separately from this, the plasmid pSNAD3AX (Japanese Patent Application No. 3-136657 filed by the present applicant) was digested with HindIII and XhoI, and the digest was subjected to 1% agarose gel electrophoresis to separate a DNA fragment of about 0.5 kb which was subsequently purified using Gene Clean. The plasmid pSNAD3AX contains a promoter which is composed of a hybrid UAS consisting of a UAS fragment from E. coli chromosome and ADH II UAS and an ADH I transcription initiation region. The 0.5 kb fragment was-then ligated with the above 10 kb fragment using T4 DNA ligase to give a cyclized product, and the aforementioned E. coli strain XL1-Blue was transformed with the product to prepare a transformant carrying the HSA expression vector pRG-SNAD3AX-TLY1-305.

On the other hand, the plasmid vector pRS303 (Sikorski and Hieter, 1989) was digested with BamHI and XhoI, and the digest was subjected to 0.7% agarose gel electrophoresis to separate a DNA fragment of about 4.3 kb which was subsequently purified using Gene Clean. Separately from this, the ADH I transcription terminator cassette vector pUC-ATE (Japanese Patent Application Laying-Open (KOKAI) No. 2-117384) was digested with BamHI and SalI, and the digest was subjected to 1% agarose gel electrophoresis to separate a DNA fragment of about 0.4 kb which was further purified using Gene Clean. The 0.4 kb fragment was ligated with the above 4.3 kb fragment using T4 DNA ligase to give a cyclized product, and the E. coli strain XL1-Blue was transformed with the product to prepare a transformant carrying the plasmid pRS303-ATE.

Next, the HSA expression vector pRG-SNAD3AX-TLY1-305 obtained above was digested with NotI and BamHI, and the digest was subjected to 0.7% agarose gel electrophoresis to isolate a DNA fragment of about 4 kb which was subsequently purified using glass powder (Gene Clean™, Bio 101). Separately from this, the plasmid pRS303-ATE obtained above was digested with NotI and BamHI, and the digest was subjected to 0.7% agarose gel electrophoresis to separate a DNA fragment of about 4 kb which was subsequently purified using Gene Clean. This fragment was ligated with the above 4 kb fragment from the pRG-SNAD3AX-TLY1-305 using T4 DNA ligase to give a cyclized product, and the E. coli strain XL1-Blue was transformed with the product to prepare a transformant carrying the HSA expression vector pRG-SNAD3AX-TLY1-305.

10 μg of the thus-obtained HSA expression vector pRG-SNAD3AXTLY-1-305 was digested with SpII in 20 μl of a digestion buffer, followed by heating of the resulting reaction mixture at 65° C. for 10 minutes in order to deactivate the enzyme. Separately from this, the yeast strain YY35A (FERM P-12480) was cultured overnight in a YPD medium (1% yeast extract, 2% peptone and 2% glucose). 0.1 ml of the obtained pre-culture was inoculated into 5 ml of the YPD medium, and cultured until turbidity at $OD_{600}$ reached 1.0.

The main culture obtained was subjected to centrifugation to recover cells which were subsequently washed with 0.5 ml of 0.1M lithium acetate solution containing 10 mM Tris-HCl (pH 7.5) and 1 mM EDTA. The cells suspended were again collected by centrifugation, resuspended in 70 μl of the 0.1M lithium acetate solution, and then incubated at 30° C. for 1 hour.

The thus treated cell suspension was mixed with 20 μl of the just described heat-treated reaction mixture, and the mixture was incubated at 30° C. for 30 minutes. To the mixture was added 500 μl of 0.1M lithium acetate solution containing 40% polyethylene glycol (average molecular weight, 4000), followed by fully mixing using a Pipetteman. After incubation at 30° C. for 45 minutes, the cell suspension was warmed at 42° C. for 5 minutes, mixed with 500 μl of sterile water, and then centrifuged to recover the cells. The obtained cells were resuspended in 100 μl of sterile water and spreaded over the SD (-His) agar medium which consists of 20 μg/ml of adenine sulfate, 20 μg/ml of arginine hydrochloride, 20 μg/ml of methionine, 20 μg/ml of tryptophan, 20 μg/ml of uracil, 30 μg/ml of isoleucine, 30 μg/ml of lysine hydrochloride, 30 μg/ml of tyrosine, 50 μg/ml of phenylalanine, 60 μg/ml of leucine, 150 μg/ml of valine, 0.67% amino acid-free Yeast Nitrogen Base, 2% glucose and 2% agar. After culturing the cells at 30° C. for 5 days, One of the colonies grown on the plate was picked up and cultured again on the SD (-His) agar medium in the same manner to obtain a purified HSA-highly producing strain SN35A.

Preparation of yeast strain SN35A-1PU (A) Construction of human PDI expression unit using TDH3 promoter:

4 μg of the plasmid phPDILy1 DNA (Japanese Patent Application No. 3-114074 filed by the present applicant) prepared by the alkaline lysis technique was digested at 37° C. for 2 hours in 100 μl of the digestion solution which consists of 10 mM Tris-HCl (pH 8.0), 60 mM NaCl, 7 mM $MgCl_2$ and 20 units of EcoRI (Nippon Gene). The reaction mixture was subjected to phenol/chloroform extraction and then to ethanol precipitation to recover the digested DNA. The DNA precipitate was dissolved in 50 μl of Klenow buffer solution (Deletion Kit for Kilo-Sequence, Takara Shuzo), mixed with 4 units of Klenow fragment (Takara Shuzo), and then incubated at 37° C. for 45 minutes to blunt the EcoRI cleavage site. This reaction mixture was subjected to phenol/chloroform extraction and then to ethanol precipitation to recover DNA. The DNA obtained was dissolved in 30 μl of a digestion solution which consists of 10 mM Tris-HCl (pH 8.0), 100 mM NaCl, 7 mM $MgCl_2$ and 10 units of BamHI (Nippon Gene), and then incubated at 37° C. for 2 hours so as to digest the DNA. Thereafter, the resulting digest was subjected to 0.8% agarose gel electrophoresis to separate a DNA fragment of about 1.8 kb which was further purified using Gene Clean.

Separately from this, 3 μg of the plasmid pRG-UAS1-N7-TLY1-305 DNA prepared by the alkaline lysis technique was digested at 37° C. for 2 hours in 100 μl of the digestion solution which consists of 10 mM Tris-HCl (pH 8.0), 100 mM NaCl, 7 mM $MgCl_2$ and 24 units of XhoI (Takara Shuzo). The resulting digest was subjected to phenol/chloroform extraction and then to ethanol precipitation to recover the digested DNA. The DNA precipitate was dissolved in 50 μl of the Klenow buffer solution. The solution obtained was mixed with 4 units of the Klenow fragment and incubated at 37° C. for 45 minutes to blunt the XhoI cleavage site. The reaction mixture was then subjected to phenol/chloroform extraction and to ethanol precipitation so as to recover DNA. The DNA was dissolved in 40 µl of the digestion solution which consists of 10 mM Tris-HCl (pH 8.0), 100 mM NaCl, 7 mM MgCl$_2$ and 10 units of BamHI (Nippon Gene), and then incubated at 37° C. for 2 hours to digest the DNA. After ethanol precipitation, the digested DNA precipitate was subjected to 0.8% agarose gel electrophoresis to separate a DNA fragment of about 8 kb which was subsequently purified using Gene Clean.

The thus recovered 1.8 kb DNA fragment from phPDILy1 (about 50 ng) and 8 kb DNA fragment from pRG-UAS1-N7-TLY1-305 (about 50 ng) were mixed with the ligation solution (Liquid A 30 µl+Liquid B 6 µl, Takara Shuzo), and then incubated at 16° C. for 1 hour to ligate the DNA fragments. Using 10 µl of the resulting DNA solution, transformation of the E. coli strain HB101 was carried out by the calcium chloride technique (Mandel, M. and Higa, A., J. Mol. Biol., vol.53, p.154, 1970). Thereafter, a transformant containing the desired plasmid (named pIV-LEUGAPhPDILy1) was selected by restriction analysis.

2 µg of the pIVLEUGAPhPDILy1 plasmid DNA prepared by the alkaline lysis technique was digested at 37° C. for 2 hours in 40 µl of the digestion solution which consists of 10 mM Tris-HCl (pH 8.0), 60 mM NaCl, 7 mM MgCl$_2$, 10 units of BamHI (Nippon Gene) and 10 units of HindIII (Nippon Gene). The resulting digest was subjected to 0.8% agarose gel electrophoresis to separate a DNA fragment of about 2.5 kb which was subsequently purified using Gene Clean. Separately from this, 2 µg of the plasmid pJDB-ADH-HSA-A DNA (Japanese Patent Application Laying-Open (KOKAI) No. 2-117384) prepared by the alkaline lysis technique was digested under the similar conditions to those in the digestion of pIVLEUGAPhPDILy1 DNA. The resulting digest was subjected to 0.8% agarose gel electrophoresis to separate a DNA fragment of about 8.5 kb which was subsequently purified using glass powder (Gene Clean™, Bio 101). The two DNA fragments (about 50 ng for each) were mixed with the ligation solution (Liquid A 30 µl+Liquid B 6 µl from the DNA ligation kit, Takara Shuzo), and then incubated at 16° C. for 1 hour so as to ligate the DNA fragments. Using 10 µl of the obtained DNA solution, transformation of the E. coli strain JM109 was carried out by the calcium chloride technique. A transformant carrying the desired plasmid (named pGAPhPDILy1) was selected for use in the following vector construction.

(B) Construction of a vector for use in the integration of human PDI expression unit into the locus ura3 on yeast chromosome:

Using the plasmid pGAPhPDILy1 prepared above, a vector for use in the integration of human PDI expression unit into yeast chromosome was constructed in the following manner:

Plasmid vector pRS306 (Sikorski and Hierter, 1989) was digested with BamHI and XhoI, and the resulting digest was subjected to 0.7% agarose gel electrophoresis to separate a DNA fragment of 4.3 kb which was subsequently purified using glass powder (Gene Clean™, Bio 101). Separately from this, the ADH transcription terminator cassette vector pUC-ATE DNA (Japanese Patent Application Laying-Open (KOKAI) No. 2-117384) was digested with BamHI and SalI, and the resulting digest was subjected to 1% agarose gel electrophoresis to separate a DNA fragment of about 0.4 kb which was subsequently purified using Gene Clean. The thus recovered 0.4 kb DNA fragment was ligated with the above 4.3 kb fragment using T4 DNA ligase to give a cyclized procuct. The E. coli strain XL1-Blue was transformed with the cyclized product to give a transformant carrying the plasmid pRS306-ATE.

Next, the HSA expression vector pRG-UAS1-N7-TLY1-305 was digested with NotI and BamHI, and the resulting digest was subjected to 0.7% agarose gel electrophoresis to separate a DNA fragment of about 4 kb which was subsequently purified using Gene Clean. Using T4 DNA ligase, the thus recovered DNA fragment was ligated with a NotI-BamHI fragment of about 5 kb prepared from the above plasmid pRS306-ATE. Using the cyclized product, transformation of the E. coli strain XL1-Blue was carried out to prepare a transformant carrying the HSA expression vector pRG-UAS1-N7-TLY1-306.

One µg of the HSA integration vector pRG-UAS1-N7-TLY1-306 DNA prepared by the alkaline technique was digested at 37° C. for 2 hours in 30 µl of the digestion solution which consists of 10 mM Tris-HCl (pH 8.0), 60 mM NaCl, 7 mM MgCl$_2$, 5 units of BamHI (Nippon Gene) and 5 units of HindIII (Nippon Gene). The resulting digest was subjected to 0.8% agarose gel electrophoresis and then treated by the glass powder technique to separate and purify a DNA fragment of about 8.5 kb. Separately from this, 2 µg of the plasmid, pIVLEUGAPhPDILy1 DNA prepared by the alkaline lysis technique was digested at 37° C. for 2 hours in 30 µl of the digestion solution which consists of 10 mM Tris-HCl (pH 8.0), 60 mM NaCl, 7 mM MgCl$_2$, 5 units of BamHI (Nippon Gene) and 5 units of HindIII (Nippon Gene). The resulting digest was subjected to 0.8% agarose gel electrophoresis and then treated by the glass powder technique to separate and purify a DNA fragment of about 2.5 kb. The two DNA fragments thus prepared (about 50ng for each) were mixed with the ligation solution (Liquid A 30 µl+Liquid B 6 µl, Takara Shuzo), and then incubated at 16° C. for 1.5 hours so as to ligate the DNA fragments. Using the recombinant plasmid (named pIVURAGAPhPDILy1) obtained, transformation of the E. coli strain MV1190 was carried out.

(C) Introduction of a human PDI expression unit into the locus ura3 of the HSA-highly secreting yeast strain SN35A:

Using the integration plasmid pIVURAGAPhPDILy1 prepared above, transformation of the HSA-highly producing yeast strain SN35A was carried out in the following manner:

30 µg of the plasmid pIVURAGAPhPDILy1 DNA prepared by the alkaline lysis technique was digested overnight at 37° C. in 400 µl of the digestion solution which consists of 10 mM Tris-HCl (pH 8.0), 100 mM NaCl, 7 mM MgCl$_2$ and 100 units of EcoRV (Takara Shuzo Co., Ltd.). The reaction mixture was subjected to phenol/chloroform extraction and to ethanol precipitation so as to recover the digested DNA fragment which was then dissolved in 10 µl of TE buffer.

A single colony of the HSA-highly secreting strain SN35A was inoculated into 5 ml of YPD medium and cultured overnight at 30° C. with shaking. 100 µl of th pre-culture was inoculated into 10 ml of the YPD medium, and cultured at 30° C. with shaking until turbidity at OD$_{600}$ reached about 0.5. The main culture obtained was subjected to centrifugation to recover the yeast cells which were subsequently washed with 1 ml of 0.1M lithium acetate solution. The cells were then collected by centrifugation, resuspended in 50 µl of the 0.1M lithium acetate solution and then incubated at 30° C. for 1 hour. The cell suspension (70 µl) was mixed with 10 µl of the just described DNA solution, and the mixture was incubated at 30° C. for 30 minutes. To the mixture was then added 500 µl of the aforementioned PEG solution. After incubation at 30° C. for 45 minutes, the mixture was warmed at 42° C. for 5 minutes, mixed with 500 µl of sterile water and then subjected to centrifugation to recover the cells. The collected cells were plated onto the SD (-Leu, -His, -Ade, -Ura) agar medium which consists of 20 μg/ml of arginine hydrochloride, 20 μg/ml of methionine, 20 μg/ml of tryptophan, 30 μg/ml of isoleucine, 30 μg/m of lysine hydrochloride, 30 μg/ml of tyrosine, 50 μg/ml of phenylalanine, 100 μg/ml. of aspartic acid, 100 μg/ml of glutamic acid, 150 μg/ml of valine, 200 μg/ml of threonine, 375 μg/ml of serine, 0.67% Bacto-yeast nitrogen base, 2% glucose and 1.5% agar. After the culture of the yeast cells at 30° C. for 3 days, a colony grown on the plate was picked up as a transformant which was named SN35A-1PU.

Introduction of ERD2 expression unit into the locus TRP1 on the chromosome of the HSA/human PDI co-expression yeast strain; SN35A-1PU Using the aforementioned integration plasmid pIVTR-PADHYERD2, transformation of the HSA/human PDI co-expression yeast strain SN35A-1PU was carried out in the following manner:

A single colony of the strain SN35A-1PU was inoculated into YPD medium and cultured overnight at 30° C. with shaking. 100 μl of the obtained pre-culture was inoculated into 10 ml of the YPD medium, and cultured at 30° C. with shaking until turbidity at $OD_{600}$ reached about 0.5. The main culture was subjected to centrifugation to recover the yeast cells which were subsequently washed with 1 ml of 0.1M lithium acetate solution (0.1M lithium acetate, 10 mM Tris-HCl (pH 7.5) and 1 mM EDTA). The cells were then collected by centrifugation, suspended in 50 μl of the 0.1M lithium acetate solution and then incubated at 30° C. for 1 hour. To the cell suspension (70 μl ) was added 30 μg of the ERD2 expression unit integration vector DNA (pIVTR-PADHYERD2), and the mixture was incubated at 30° C. for 30 minutes. A sample of pIVTRPADHYERD2 was deposited on Jun. 3, 1994 with the National Institute of Bioscience and Human-Technology Agency of Industrial Science and Technology 1–3, Higashi 1-chome, Tsukubashi, Ibarakiken, 305 Japan, and received Accession No. FERM BP-4686. To the mixture was further added 500 μl of a PEG solution (40% polyethylene glycol #4000, 0.1M lithium acetate, 10 mM Tris-HCl (pH 7.5) and 1 mM EDTA), followed by mixing. After incubation at 30° C. for 45 minutes, the cell suspension was warmed at 42° C. for 5 minutes, mixed with 500 μl of sterile water and then centrifuged to recover the yeast cells. The cells collected were plated and cultured on the SD (-Leu, -His, -Ade, -Ura, -Trp) plate which consists of 20 μg/ml of arginine hydrochloride, 20 μg/ml of methionine, 30 μg/ml of tyrosin, 30 μg/ml of isoleucine, 30 μg/ml of lysine hydrochloride, 50 μg/ml of phenylalanine, 100 μg/ml of aspartic acid, 100 μg/ml of glutamic acid, 150 μg/ml of valine, 200 μg/ml of threonine, 375 μg/ml of serine, 0.67% Bacto-nitrogen Base, 2% glucose and 1.5% agar. These amino acids used were supplied from Wako Pure Chemical Industries. After culturing the cells at 30° C., a colony grown on the plate was picked up as a transformant which was named SN35A-1PUAET. A sample of SN35A-1PUAET was deposited on Jun. 3, 1994 with the National Institute of Bioscience and Human-Technology Agency of Industrial Science and Technology 1–3, Higashi 1-chome, Tsukubashi, Ibaraki-ken, 305 Japan, and received Accession No. FERM BP-4687.

Effect of the co-expression of ERD2 on the intracellular retention of human PDI, and enhancement accompanied thereby of the expression and secretion of HSA Using the transformant prepared above, effect of the co-expression of ERD2 on the intracellular retensiong of human PDI and enhancement accompanied thereby of the expression and secretion of HSA were examined in the following manner:

6 single colonies of the transformant SN35A-1PUAET were removed from the SD plate. Each of the colonies was inoculated into 5 ml of the SD (-His, -Leu, -Ade, -Ura, -Trp) medium and precultured at 30° C. for 24 hours with shaking. 100 μl of the pre-culture obtained was inoculated into 5 ml of the YPD medium and cultured at 30° C. for 24 hours. 200 μl of each culture was centrifuged to recover 100 μl of supernatant which was then mixed with the equal volume of ethanol and left for 3 hours on ice. After centrifugation of the precipitates, the pellets collected were separately dried under a reduced pressure, and dissolved in 8 μl of a sample buffer for SDS-PAGE (62.5 mM TriS-HCl (pH 6.8), 2% SDS, 10% glycerol, 0.72M β-mercaptoethanol and 0.005% Bromophenol Blue). After boiling for 5 minutes, the samples were subjected to SDS-PAGE on SDS/PAGE Plate 4/20 (Daiichi Kagaku Yakuhin) with 4–20% gradient. At the same time, 0.5 μg of HSA (Sigma) was run as a standard for quantifying a HSA level. The resulting gel was stained with a staining solution (0.15% Coomassie Brilliant Blue, 10% acetic acid and 40% methanol) and then soaked in a decoloring solution (10% acetic acid and 40% methanol) so as to visualize the expressed product in the culture medium. The same procedure was repeated for a main culture sample after culturing for 48 hours, except that 50 μl of the culture was used for the ethanol precipitation. The same procedure was also repeated using the SN35A-1PU as control. Using the gels after SDS-PAGE, the amount of secreted HSA from each strain was determined using a densitometer (IMAGE ANALYSIS SYSTEM, TEFCO). As shown in FIGS. 12 and 13, the amount of PDI secreted into the medium decreased sharply due to the co-expression of ERD2 while the secretion of HSA was increased by 26% in average after culturing for 24 hours and by 17% in average after culturing for 48 hours.

What is claimed is:

1. A transformed yeast cell comprising the following expression units integrated on a yeast chromosome in a co-expressible state:

a first expression unit containing a gene coding for a receptor for an endoplasmic reticulum retention signal, wherein the receptor is either the yeast receptor protein ERD2 or a protein which is obtainable from a yeast or a mammal and which is capable of binding to a retention signal selected from the group consisting of KDEL (SEQ ID NO: 5), HDEL (SEQ ID NO: 6), DDEL (SEQ ID NO: 7), ADEL (SEQ ID NO: 8), SDEL (SEQ ID NO: 9), RDEL (SEQ ID NO: 10), KEEL (SEQ ID NO: 11), QEDL (SEQ ID NO: 12), HIEL (SEQ ID NO: 13), HTEL (SEQ ID NO: 14), and KQDL (SEQ ID NO: 15); and a second expression unit containing a gene encoding a protein disulfide isomerase, wherein said isomerase comprises an endoplasmic reticulum retention signal, or a gene encoding a fusion protein comprising the amino acid sequence of said isomerase and a human serum albumin prepro-sequence.

2. A transformed yeast cell according to claim 1, wherein said first expression unit is the expression plasmid pIVTR-PADHYERD2.

3. A transformed yeast cell according to claim 1, wherein said fusion protein has the amino acid sequence of the polypeptide encoded by the nucleotide sequence shown in SEQ ID NO: 2.

4. A transformed yeast cell according to claim 3, wherein the gene encoding said fusion protein has the nucleotide sequence shown in SEQ ID NO: 2.

5. A transformed yeast cell according to claim 1, wherein said gene encoding a protein disulfide isomerase (PDI) is a human PDI gene.

6. A transformed yeast cell comprising the following expression units integrated on a yeast chromosome in a co-expressible state:

a first expression unit containing a gene coding for a receptor for an endoplasmic reticulum retention signal, wherein the receptor is either the yeast receptor protein ERD2 or a protein which is obtainable from a yeast or a mammal and which is capable of binding to a retention signal selected from the group consisting of KDEL (SEQ ID NO: 5), HDEL (SEQ ID NO: 6), DDEL (SEQ ID NO: 7), ADEL (SEQ ID NO: 8), SDEL (SEQ ID NO: 9), RDEL (SEQ ID NO: 10), KEEL (SEQ ID NO: 11), QEDL (SEQ ID NO: 12), HIEL (SEQ ID NO: 13), HTEL (SEQ ID NO: 14), and KQDL (SEQ ID NO: 15); and a second expression unit containing a gene encoding a protein having protein disulfide isomerase activity, wherein said polypeptide comprises an endoplasmic reticulum retention signal, or a gene encoding a fusion protein comprising the amino acid sequence of said protein having isomerase activity and a human serum albumin prepro-sequence.

7. A transformed yeast cell comprising the following expression units integrated on a yeast chromosome in a co-expressible state:
   a first expression unit containing a gene coding for a receptor for an endoplasmic reticulum retention signal, wherein the receptor is either the yeast receptor protein ERD2 or a protein which is obtainable from a yeast or a mammal and which is capable of binding to a retention signal selected from the group consisting of KDEL (SEQ ID NO: 5), HDEL (SEQ ID NO: 6), DDEL (SEQ ID NO: 7), ADEL (SEQ ID NO: 8), SDEL (SEQ ID NO: 9), RDEL (SEQ ID NO: 10), KEEL (SEQ ID NO: 11), QEDL (SEQ ID NO: 12), HIEL (SEQ ID NO: 13), HTEL (SEQ ID NO: 14), and KQDL (SEQ ID NO: 15); and
   a second expression unit containing a gene encoding a protein disulfide isomerase, wherein said isomerase comprises an endoplasmic reticulum retention signal, or a gene encoding a fusion protein comprising the amino acid sequence of said isomerase and a human serum albumin prepro-sequence; and
   a third expression unit containing a foreign gene encoding a polypeptide which is a substrate of said protein disulfide isomerase.

8. A transformed yeast cell according to claim 7, wherein said first expression unit is the expression plasmid pIVTR-PADHYERD2.

9. A transformed yeast cell according to claim 7, wherein said fusion protein has the amino acid sequence of the polypeptide encoded by the nucleotide sequence shown in SEQ ID NO: 2.

10. A transformed yeast cell according to claim 7, wherein the gene encoding said fusion protein has the nucleotide sequence shown in SEQ ID NO: 2.

11. A transformed yeast cell according to claim 7, wherein said gene encoding a protein disulfide isomerase (PDI) is a human PDI gene.

12. A transformed yeast cell according to claim 7, wherein said foreign gene encodes human serum albumin.

13. A transformed yeast cell according to claim 7, which is a yeast strain SN35A-1PUAET.

14. A process for producing the polypeptide encoded by the foreign gene of any one of claims 6, 7, 9, 10, 11, or 12, which comprises the steps of:
   culturing said transformed yeast cell in an appropriate medium;
   bringing about the co-expression of said expression units such that said polypeptide is predominately secreted by the transformed yeast cell, while both said receptor and said isomerase or fusion protein remain in the endoplasmic reticulum; and
   recovering said secreted polypeptide.

15. A process according to claim 14, wherein said polypeptide is human serum albumin.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 2454
( B ) TYPE: nucleic acid
( C ) STRANDEDNESS: double
( D ) TOPOLOGY: linear ( i i ) MOLECULE TYPE: cDNA to mRNA ( i x ) IMMEDIATE SOURCE: human liver and placenta lgt11 cDNA
libraries (ex Clontech Inc., USA)

( x i ) SEQUENCE DESCRIPTION: SEQ ID NO:1:

```
GAATTCCGGG GGCGACGAGA GAAGCGCCCC GCCTGATCCG TGTCCGAC ATG CTG CGC      57
                                                     Met Leu Arg
                                                         -15

CGC GCT CTG CTG TGC CTG GCC GTG GCC GCC CTG GTG CGC GCC GAC GCC     105
Arg Ala Leu Leu Cys Leu Ala Val Ala Ala Leu Val Arg Ala Asp Ala
            -10                  -5                               1

CCC GAG GAG GAG GAC CAC GTC CTG GTG CTG CGG AAA AGC AAC TTC GCG     153
Pro Glu Glu Glu Asp His Val Leu Val Leu Arg Lys Ser Asn Phe Ala
         5                  10                  15

GAG GCG CTG GCG GCC CAC AAG TAC CTG CTG GTG GAG TTC TAT GCC CCT     201
Glu Ala Leu Ala Ala His Lys Tyr Leu Leu Val Glu Phe Tyr Ala Pro
     20                  25                  30

TGG TGT GGC CAC TGC AAG GCT CTG GCC CCT GAG TAT GCC AAA GCC GCT     249
Trp Cys Gly His Cys Lys Ala Leu Ala Pro Glu Tyr Ala Lys Ala Ala
 35                  40                  45                  50

GGG AAG CTG AAG GCA GAA GGT TCC GAG ATC AGG TTG GCC AAG GTG GAC     297
Gly Lys Leu Lys Ala Glu Gly Ser Glu Ile Arg Leu Ala Lys Val Asp
                     55                  60                  65

GCC ACG GAG GAG TCT GAC CTG GCC CAG CAG TAC GGC GTG CGC GGC TAT     345
Ala Thr Glu Glu Ser Asp Leu Ala Gln Gln Tyr Gly Val Arg Gly Tyr
                 70                  75                  80

CCC ACC ATC AAG TTC TTC AGG AAT GGA GAC ACG GCT TCC CCC AAG GAA     393
Pro Thr Ile Lys Phe Phe Arg Asn Gly Asp Thr Ala Ser Pro Lys Glu
             85                  90                  95

TAT ACA GCT GGC AGA GAG GCT GAT GAC ATC GTG AAC TGG CTG AAG AAG     441
Tyr Thr Ala Gly Arg Glu Ala Asp Asp Ile Val Asn Trp Leu Lys Lys
        100                 105                 110

CGC ACG GGC CCG GCT GCC ACC ACC CTG CCT GAC GGC GCA GCT GCA GAG     489
Arg Thr Gly Pro Ala Ala Thr Thr Leu Pro Asp Gly Ala Ala Ala Glu
115                 120                 125                 130

TCC TTG GTG GAG TCC AGC GAG GTG GCT GTC ATC GGC TTC TTC AAG GAC     537
Ser Leu Val Glu Ser Ser Glu Val Ala Val Ile Gly Phe Phe Lys Asp
                135                 140                 145

GTG GAG TCG GAC TCT GCC AAG CAG TTT TTG CAG GCA GCA GAG GCC ATC     585
Val Glu Ser Asp Ser Ala Lys Gln Phe Leu Gln Ala Ala Glu Ala Ile
            150                 155                 160

GAT GAC ATA CCA TTT GGG ATC ACT TCC AAC AGT GAC GTG TTC TCC AAA     633
Asp Asp Ile Pro Phe Gly Ile Thr Ser Asn Ser Asp Val Phe Ser Lys
        165                 170                 175

TAC CAG CTC GAC AAA GAT GGG GTT GTC CTC TTT AAG AAG TTT GAT GAA     681
Tyr Gln Leu Asp Lys Asp Gly Val Val Leu Phe Lys Lys Phe Asp Glu
180                 185                 190

GGC CGG AAC AAC TTT GAA GGG GAG GTC ACC AAG GAG AAC CTG CTG GAC     729
Gly Arg Asn Asn Phe Glu Gly Glu Val Thr Lys Glu Asn Leu Leu Asp
195                 200                 205                 210

TTT ATC AAA CAC AAC CAG CTG CCC CTT GTC ATC GAG TTC ACC GAG CAG     777
Phe Ile Lys His Asn Gln Leu Pro Leu Val Ile Glu Phe Thr Glu Gln
            215                 220                 225

ACA GCC CCG AAG ATT TTT GGA GGT GAA ATC AAG ACT CAC ATC CTG CTG     825
Thr Ala Pro Lys Ile Phe Gly Gly Glu Ile Lys Thr His Ile Leu Leu
        230                 235                 240

TTC TTG CCC AAG AGT GTG TCT GAC TAT GAC GGC AAA CTG AGC AAC TTC     873
Phe Leu Pro Lys Ser Val Ser Asp Tyr Asp Gly Lys Leu Ser Asn Phe
        245                 250                 255

AAA ACA GCA GCC GAG AGC TTC AAG GGC AAG ATC CTG TTC ATC TTC ATC     921
```

|     |     |     |     |     |     |     |     |     |     |     |     |     |     |     |     |
| --- | --- | --- | --- | --- | --- | --- | --- | --- | --- | --- | --- | --- | --- | --- | --- |
| Lys | Thr | Ala | Ala | Glu | Ser | Phe | Lys | Gly | Lys | Ile | Leu | Phe | Ile | Phe | Ile |
|     | 260 |     |     |     | 265 |     |     |     |     | 270 |     |     |     |     |     |

```
GAC AGC GAC CAC ACC GAC AAC CAG CGC ATC CTC GAG TTC TTT GGC CTG      969
Asp Ser Asp His Thr Asp Asn Gln Arg Ile Leu Glu Phe Phe Gly Leu
275             280                 285                 290

AAG AAG GAA GAG TGC CCG GCC GTG CGC CTC ATC ACC CTG GAG GAG GAG     1017
Lys Lys Glu Glu Cys Pro Ala Val Arg Leu Ile Thr Leu Glu Glu Glu
                295                 300                 305

ATG ACC AAG TAC AAG CCC GAA TCG GAG GAG CTG ACG GCA GAG AGG ATC     1065
Met Thr Lys Tyr Lys Pro Glu Ser Glu Glu Leu Thr Ala Glu Arg Ile
            310                 315                 320

ACA GAG TTC TGC CAC CGC TTC CTG GAG GGC AAA ATC AAG CCC CAC CTG     1113
Thr Glu Phe Cys His Arg Phe Leu Glu Gly Lys Ile Lys Pro His Leu
        325                 330                 335

ATG AGC CAG GAG CTG CCG GAG GAC TGG GAC AAG CAG CCT GTC AAG GTG     1161
Met Ser Gln Glu Leu Pro Glu Asp Trp Asp Lys Gln Pro Val Lys Val
340                 345                 350

CTT GTT GGG AAG AAC TTT GAA GAC GTG GCT TTT GAT GAG AAA AAA AAC     1209
Leu Val Gly Lys Asn Phe Glu Asp Val Ala Phe Asp Glu Lys Lys Asn
355                 360                 365                 370

GTC TTT GTG GAG TTC TAT GCC CCA TGG TGT GGT CAC TGC AAA CAG TTG     1257
Val Phe Val Glu Phe Tyr Ala Pro Trp Cys Gly His Cys Lys Gln Leu
                375                 380                 385

GCT CCC ATT TGG GAT AAA CTG GGA GAG ACG TAC AAG GAC CAT GAG AAC     1305
Ala Pro Ile Trp Asp Lys Leu Gly Glu Thr Tyr Lys Asp His Glu Asn
            390                 395                 400

ATC GTC ATC GCC AAG ATG GAC TCG ACT GCC AAC GAG GTG GAG GCC GTC     1353
Ile Val Ile Ala Lys Met Asp Ser Thr Ala Asn Glu Val Glu Ala Val
        405                 410                 415

AAA GTG CAC AGC TTC CCC ACA CTC AAG TTC TTT CCT GCC AGT GCC GAC     1401
Lys Val His Ser Phe Pro Thr Leu Lys Phe Phe Pro Ala Ser Ala Asp
    420                 425                 430

AGG ACG GTC ATT GAT TAC AAC GGG GAA CGC ACG CTG GAT GGT TTT AAG     1449
Arg Thr Val Ile Asp Tyr Asn Gly Glu Arg Thr Leu Asp Gly Phe Lys
435                 440                 445                 450

AAA TTC CTG GAG AGC GGT GGC CAG GAT GGG GCA GGG GAT GAT GAC GAT     1497
Lys Phe Leu Glu Ser Gly Gly Gln Asp Gly Ala Gly Asp Asp Asp Asp
                455                 460                 465

CTC GAG GAC CTG GAA GAA GCA GAG GAG CCA GAC ATG GAG GAA GAC GAT     1545
Leu Glu Asp Leu Glu Glu Ala Glu Glu Pro Asp Met Glu Glu Asp Asp
            470                 475                 480

GAT CAG AAA GCT GTG AAA GAT GAA CTG TAA TACGCAAAGC CAGACCCGGG       1595
Asp Gln Lys Ala Val Lys Asp Glu Leu *
        485                 490

CGCTGCCGAG ACCCCTCGGG GGCTGCACAC CCAGCAGCAG CGCACGCCTC CGAAGCCTGC   1655
GGCCTCGCTT GAAGGAGGGC GTCGCCGGAA ACCCAGGGAA CCTCTCTGAA GTGACACCTC   1715
ACCCCTACAC ACCGTCCGTT CACCCCCGTC TCTTCCTTCT GCTTTTCGGT TTTTGGAAAG   1775
GGATCCATCT CCAGGCAGCC CACCCTGGTG GGGCTTGTTT CCTGAAACCA TGATGTACTT   1835
TTTCATACAT GAGTCTGTCC AGAGTGCTTG CTACCGTGTT CGGAGTCTCG CTGCCTCCCT   1895
CCCGCGGGAG GTTTCTCCTC TTTTTGAAAA TTCCGTCTGT GGGATTTTTA GACATTTTTC   1955
GACATCAGGG TATTTGTTCC ACCTTGGCCA GGCCTCCTCG GAGAAGCTTG TCCCCCGTGT   2015
GGGAGGGACG GAGCCGGACT GGACATGGTC ACTCAGTACC GCCTGCAGTG TCGCCATGAC   2075
TGATCATGGC TCTTGCATTT TTGGGTAAAT GGAGACTTCC GGATCCTGTC AGGGTGTCCC   2135
CCATGCCTGG AAGAGGAGCT GGTGGCTGCC AGCCCTGGGG CCCGGCACAG GCCTGGGCCT   2195
TCCCCTTCCC TCAAGCCAGG GCTCCTCCTC CTGTCGTGGG CTCATTGTGA CCACTGGCCT   2255
```

```
CTCTACAGCA  CGGCCTGTGG  CCTGTTCAAG  GCAGAACCAC  GACCCTTGAC  TCCCGGGTGG    2315

GGAGGTGGCC  AAGGATGCTG  GAGCTGAATC  AGACGCTGAC  AGTTCTTCAG  GCATTTCTAT    2375

TTCACAATCG  AATTGAACAC  ATTGGCCAAA  TAAAGTTGAA  ATTTTACCCA  CCCAAAAAAA    2435

AAAAAAAAAA  CCCGAATTC                                                     2454
```

( 2 ) INFORMATION FOR SEQ ID NO:2:

( i ) SEQUENCE CHARACTERISTICS:
 ( A ) LENGTH: 1545
 ( B ) TYPE: nucleic acid
 ( C ) STRANDEDNESS: double
 ( D ) TOPOLOGY: linear ( i i ) MOLECULE TYPE: other nucleic acid (semi-synthetic DNA)

( x i ) SEQUENCE DESCRIPTION: SEQ ID NO:2:

```
                        ATG  AAG  TGG  GTT  ACC  TTC  ATC  TCT  TTG  TTG      30
                        Met  Lys  Trp  Val  Thr  Phe  Ile  Ser  Leu  Leu
                                            -20                       -15

TTC  TTG  TTC  TCT  TCT  GCT  TAC  TCT  AGA  GGT  GTT  TTC  AGA  AGG  GGC  GCC      78
Phe  Leu  Phe  Ser  Ser  Ala  Tyr  Ser  Arg  Gly  Val  Phe  Arg  Arg  Gly  Ala
              -10                       -5                              1

CCC  GAG  GAG  GAG  GAC  CAC  GTC  CTG  GTG  CTG  CGG  AAA  AGC  AAC  TTC  GCG     126
Pro  Glu  Glu  Glu  Asp  His  Val  Leu  Val  Leu  Arg  Lys  Ser  Asn  Phe  Ala
          5                        10                      15

GAG  GCG  CTG  GCG  GCC  CAC  AAG  TAC  CTG  CTG  GTG  GAG  TTC  TAT  GCC  CCT     174
Glu  Ala  Leu  Ala  Ala  His  Lys  Tyr  Leu  Leu  Val  Glu  Phe  Tyr  Ala  Pro
         20                        25                      30

TGG  TGT  GGC  CAC  TGC  AAG  GCT  CTG  GCC  CCT  GAG  TAT  GCC  AAA  GCC  GCT     222
Trp  Cys  Gly  His  Cys  Lys  Ala  Leu  Ala  Pro  Glu  Tyr  Ala  Lys  Ala  Ala
 35                       40                      45                      50

GGG  AAG  CTG  AAG  GCA  GAA  GGT  TCC  GAG  ATC  AGG  TTG  GCC  AAG  GTG  GAC     270
Gly  Lys  Leu  Lys  Ala  Glu  Gly  Ser  Glu  Ile  Arg  Leu  Ala  Lys  Val  Asp
                     55                       60                     65

GCC  ACG  GAG  GAG  TCT  GAC  CTG  GCC  CAG  CAG  TAC  GGC  GTG  CGC  GGC  TAT     318
Ala  Thr  Glu  Glu  Ser  Asp  Leu  Ala  Gln  Gln  Tyr  Gly  Val  Arg  Gly  Tyr
                70                       75                    80

CCC  ACC  ATC  AAG  TTC  TTC  AGG  AAT  GGA  GAC  ACG  GCT  TCC  CCC  AAG  GAA     366
Pro  Thr  Ile  Lys  Phe  Phe  Arg  Asn  Gly  Asp  Thr  Ala  Ser  Pro  Lys  Glu
               85                       90                     95

TAT  ACA  GCT  GGC  AGA  GAG  GCT  GAT  GAC  ATC  GTG  AAC  TGG  CTG  AAG  AAG     414
Tyr  Thr  Ala  Gly  Arg  Glu  Ala  Asp  Asp  Ile  Val  Asn  Trp  Leu  Lys  Lys
         100                      105                     110

CGC  ACG  GGC  CCG  GCT  GCC  ACC  ACC  CTG  CCT  GAC  GGC  GCA  GCT  GCA  GAG     462
Arg  Thr  Gly  Pro  Ala  Ala  Thr  Thr  Leu  Pro  Asp  Gly  Ala  Ala  Ala  Glu
115                      120                     125                    130

TCC  TTG  GTG  GAG  TCC  AGC  GAG  GTG  GCT  GTC  ATC  GGC  TTC  TTC  AAG  GAC     510
Ser  Leu  Val  Glu  Ser  Ser  Glu  Val  Ala  Val  Ile  Gly  Phe  Phe  Lys  Asp
                    135                      140                    145

GTG  GAG  TCG  GAC  TCT  GCC  AAG  CAG  TTT  TTG  CAG  GCA  GCA  GAG  GCC  ATC     558
Val  Glu  Ser  Asp  Ser  Ala  Lys  Gln  Phe  Leu  Gln  Ala  Ala  Glu  Ala  Ile
              150                      155                     160

GAT  GAC  ATA  CCA  TTT  GGG  ATC  ACT  TCC  AAC  AGT  GAC  GTG  TTC  TCC  AAA     606
Asp  Asp  Ile  Pro  Phe  Gly  Ile  Thr  Ser  Asn  Ser  Asp  Val  Phe  Ser  Lys
         165                      170                     175

TAC  CAG  CTC  GAC  AAA  GAT  GGG  GTT  GTC  CTC  TTT  AAG  AAG  TTT  GAT  GAA     654
Tyr  Gln  Leu  Asp  Lys  Asp  Gly  Val  Val  Leu  Phe  Lys  Lys  Phe  Asp  Glu
180                      185                     190

GGC  CGG  AAC  AAC  TTT  GAA  GGG  GAG  GTC  ACC  AAG  GAG  AAC  CTG  CTG  GAC     702
Gly  Arg  Asn  Asn  Phe  Glu  Gly  Glu  Val  Thr  Lys  Glu  Asn  Leu  Leu  Asp
```

| | | | | | | | | | | | | | | | | |
|---|---|---|---|---|---|---|---|---|---|---|---|---|---|---|---|---|
|195| | | | |200| | | | |205| | | | |210| |
|TTT|ATC|AAA|CAC|AAC|CAG|CTG|CCC|CTT|GTC|ATC|GAG|TTC|ACC|GAG|CAG|750|
|Phe|Ile|Lys|His|Asn|Gln|Leu|Pro|Leu|Val|Ile|Glu|Phe|Thr|Glu|Gln| |
| | | | |215| | | | |220| | | | |225| | |
|ACA|GCC|CCG|AAG|ATT|TTT|GGA|GGT|GAA|ATC|AAG|ACT|CAC|ATC|CTG|CTG|798|
|Thr|Ala|Pro|Lys|Ile|Phe|Gly|Gly|Glu|Ile|Lys|Thr|His|Ile|Leu|Leu| |
| | | |230| | | | |235| | | | |240| | | |
|TTC|TTG|CCC|AAG|AGT|GTG|TCT|GAC|TAT|GAC|GGC|AAA|CTG|AGC|AAC|TTC|846|
|Phe|Leu|Pro|Lys|Ser|Val|Ser|Asp|Try|Asp|Gly|Lys|Leu|Ser|Asn|Phe| |
| | |245| | | | |250| | | | |255| | | | |
|AAA|ACA|GCA|GCC|GAG|AGC|TTC|AAG|GGC|AAG|ATC|CTG|TTC|ATC|TTC|ATC|894|
|Lys|Thr|Ala|Ala|Glu|Ser|Phe|Lys|Gly|Lys|Ile|Leu|Phe|Ile|Phe|Ile| |
| |260| | | | |265| | | | |270| | | | | |
|GAC|AGC|GAC|CAC|ACC|GAC|AAC|CAG|CGC|ATC|CTC|GAG|TTC|TTT|GGC|CTG|942|
|Asp|Ser|Asp|His|Thr|Asp|Asn|Gln|Arg|Ile|Leu|Glu|Phe|Phe|Gly|Leu| |
|275| | | | |280| | | | |285| | | | |290| |
|AAG|AAG|GAA|GAG|TGC|CCG|GCC|GTG|CGC|CTC|ATC|ACC|CTG|GAG|GAG|GAG|990|
|Lys|Lys|Glu|Glu|Cys|Pro|Ala|Val|Arg|Leu|Ile|Thr|Leu|Glu|Glu|Glu| |
| | | | |295| | | | |300| | | | |305| | |
|ATG|ACC|AAG|TAC|AAG|CCC|GAA|TCG|GAG|GAG|CTG|ACG|GCA|GAG|AGG|ATC|1038|
|Met|Thr|Lys|Tyr|Lys|Pro|Glu|Ser|Glu|Glu|Leu|Thr|Ala|Glu|Arg|Ile| |
| | | |310| | | | |315| | | | |320| | | |
|ACA|GAG|TTC|TGC|CAC|CGC|TTC|CTG|GAG|GGC|AAA|ATC|AAG|CCC|CAC|CTG|1086|
|Thr|Glu|Phe|Cys|His|Arg|Phe|Leu|Glu|Gly|Lys|Ile|Lys|Pro|His|Leu| |
| | |325| | | | |330| | | | |335| | | | |
|ATG|AGC|CAG|GAG|CTG|CCG|GAG|GAC|TGG|GAC|AAG|CAG|CCT|GTC|AAG|GTG|1134|
|Met|Ser|Gln|Glu|Leu|Pro|Glu|Asp|Trp|Asp|Lys|Gln|Pro|Val|Lys|Val| |
| |340| | | | |345| | | | |350| | | | | |
|CTT|GTT|GGG|AAG|AAC|TTT|GAA|GAC|GTG|GCT|TTT|GAT|GAG|AAA|AAA|AAC|1182|
|Leu|Val|Gly|Lys|Asn|Phe|Glu|Asp|Val|Ala|Phe|Asp|Glu|Lys|Lys|Asn| |
|355| | | | |360| | | | |365| | | | |370| |
|GTC|TTT|GTG|GAG|TTC|TAT|GCC|CCA|TGG|TGT|GGT|CAC|TGC|AAA|CAG|TTG|1230|
|Val|Phe|Val|Glu|Phe|Tyr|Ala|Pro|Trp|Cys|Gly|His|Cys|Lys|Gln|Leu| |
| | | | |375| | | | |380| | | | |385| | |
|GCT|CCC|ATT|TGG|GAT|AAA|CTG|GGA|GAG|ACG|TAC|AAG|GAC|CAT|GAG|AAC|1278|
|Ala|Pro|Ile|Trp|Asp|Lys|Leu|Gly|Glu|Thr|Tyr|Lys|Asp|His|Glu|Asn| |
| | | |390| | | | |395| | | | |400| | | |
|ATC|GTC|ATC|GCC|AAG|ATG|GAC|TCG|ACT|GCC|AAC|GAG|GTG|GAG|GCC|GTC|1326|
|Ile|Val|Ile|Ala|Lys|Met|Asp|Ser|Thr|Ala|Asn|Glu|Val|Glu|Ala|Val| |
| | |405| | | | |410| | | | |415| | | | |
|AAA|GTG|CAC|AGC|TTC|CCC|ACA|CTC|AAG|TTC|TTT|CCT|GCC|AGT|GCC|GAC|1374|
|Lys|Val|His|Ser|Phe|Pro|Thr|Leu|Lys|Phe|Phe|Pro|Ala|Ser|Ala|Asp| |
| |420| | | | |425| | | | |430| | | | | |
|AGG|ACG|GTC|ATT|GAT|TAC|AAC|GGG|GAA|CGC|ACG|CTG|GAT|GGT|TTT|AAG|1422|
|Arg|Thr|Val|Ile|Asp|Tyr|Asn|Gly|Glu|Arg|Thr|Leu|Asp|Gly|Phe|Lys| |
|435| | | | |440| | | | |445| | | | |450| |
|AAA|TTC|CTG|GAG|AGC|GGT|GGC|CAG|GAT|GGG|GCA|GGG|GAT|GAT|GAC|GAT|1470|
|Lys|Phe|Leu|Glu|Ser|Gly|Gly|Gln|Asp|Gly|Ala|Gly|Asp|Asp|Asp|Asp| |
| | | | |455| | | | |460| | | | |465| | |
|CTC|GAG|GAC|CTG|GAA|GAA|GCA|GAG|GAG|CCA|GAC|ATG|GAG|GAA|GAC|GAT|1518|
|Leu|Glu|Asp|Leu|Glu|Glu|Ala|Glu|Glu|Pro|Asp|Met|Glu|Glu|Asp|Asp| |
| | | |470| | | | |475| | | | |480| | | |
|GAT|CAG|AAA|GCT|GTG|AAA|GAT|GAA|CTG| | | | | | | |1545|
|Asp|Gln|Lys|Ala|Val|Lys|Asp|Glu|Leu| | | | | | | | |
| | |485| | | | |490| | | | | | | | | |

( 2 ) INFORMATION FOR SEQ ID NO:3:

( i ) SEQUENCE CHARACTERISTICS:
        ( A ) LENGTH: 491
        ( B ) TYPE: amino acid ( D ) TOPOLOGY: linear ( i i ) MOLECULE TYPE:
    ( A ) DESCRIPTION: protein ( x i ) SEQUENCE DESCRIPTION: SEQ ID NO:3:

```
Gly  Ala  Pro  Glu  Glu  Asp  His  Val  Leu  Val  Leu  Arg  Lys  Ser  Asn
 1                    5                   10                        15

Phe  Ala  Glu  Ala  Leu  Ala  Ala  His  Lys  Tyr  Leu  Leu  Val  Glu  Phe  Tyr
               20                        25                   30

Ala  Pro  Trp  Cys  Gly  His  Cys  Lys  Ala  Leu  Ala  Pro  Glu  Tyr  Ala  Lys
               35                        40                   45

Ala  Ala  Gly  Lys  Leu  Lys  Ala  Glu  Gly  Ser  Glu  Ile  Arg  Leu  Ala  Lys
     50                        55                        60

Val  Asp  Ala  Thr  Glu  Glu  Ser  Asp  Leu  Ala  Gln  Gln  Tyr  Gly  Val  Arg
 65                   70                        75                        80

Gly  Tyr  Pro  Thr  Ile  Lys  Phe  Phe  Arg  Asn  Gly  Asp  Thr  Ala  Ser  Pro
                    85                        90                        95

Lys  Glu  Tyr  Thr  Ala  Gly  Arg  Glu  Ala  Asp  Asp  Ile  Val  Asn  Trp  Leu
                   100                       105                  110

Lys  Lys  Arg  Thr  Gly  Pro  Ala  Ala  Thr  Thr  Leu  Pro  Asp  Gly  Ala  Ala
          115                       120                  125

Ala  Glu  Ser  Leu  Val  Glu  Ser  Ser  Glu  Val  Ala  Val  Ile  Gly  Phe  Phe
     130                       135                  140

Lys  Asp  Val  Glu  Ser  Asp  Ser  Ala  Lys  Gln  Phe  Leu  Gln  Ala  Ala  Glu
145                       150                  155                       160

Ala  Ile  Asp  Asp  Ile  Pro  Phe  Gly  Ile  Thr  Ser  Asn  Ser  Asp  Val  Phe
                    165                       170                  175

Ser  Lys  Tyr  Gln  Leu  Asp  Lys  Asp  Gly  Val  Val  Leu  Phe  Lys  Lys  Phe
               180                       185                  190

Asp  Glu  Gly  Arg  Asn  Asn  Phe  Glu  Gly  Glu  Val  Thr  Lys  Glu  Asn  Leu
          195                       200                  205

Leu  Asp  Phe  Ile  Lys  His  Asn  Gln  Leu  Pro  Leu  Val  Ile  Glu  Phe  Thr
     210                       215                  220

Glu  Gln  Thr  Ala  Pro  Lys  Ile  Phe  Gly  Gly  Glu  Ile  Lys  Thr  His  Ile
225                       230                  235                       240

Leu  Leu  Phe  Leu  Pro  Lys  Ser  Val  Ser  Asp  Tyr  Asp  Gly  Lys  Leu  Ser
                    245                       250                  255

Asn  Phe  Lys  Thr  Ala  Ala  Glu  Ser  Phe  Lys  Gly  Lys  Ile  Leu  Phe  Ile
               260                       265                  270

Phe  Ile  Asp  Ser  Asp  His  Thr  Asp  Asn  Gln  Arg  Ile  Leu  Glu  Phe  Phe
          275                       280                  285

Gly  Leu  Lys  Lys  Glu  Glu  Cys  Pro  Ala  Val  Arg  Leu  Ile  Thr  Leu  Glu
     290                       295                  300

Glu  Glu  Met  Thr  Lys  Tyr  Lys  Pro  Glu  Ser  Glu  Glu  Leu  Thr  Ala  Glu
305                       310                  315                       320

Arg  Ile  Thr  Glu  Phe  Cys  His  Arg  Phe  Leu  Glu  Gly  Lys  Ile  Lys  Pro
                    325                       330                  335

His  Leu  Met  Ser  Gln  Glu  Leu  Pro  Glu  Asp  Trp  Asp  Lys  Gln  Pro  Val
               340                       345                  350

Lys  Val  Leu  Val  Gly  Lys  Asn  Phe  Glu  Asp  Val  Ala  Phe  Asp  Glu  Lys
          355                       360                  365

Lys  Asn  Val  Phe  Val  Glu  Phe  Tyr  Ala  Pro  Trp  Cys  Gly  His  Cys  Lys
     370                       375                  380

Gln  Leu  Ala  Pro  Ile  Trp  Asp  Lys  Leu  Gly  Glu  Thr  Tyr  Lys  Asp  His
```

```
385                         390                         395                             400
Glu  Asn  Ile  Val  Ile  Ala  Lys  Met  Asp  Ser  Thr  Ala  Asn  Glu  Val  Glu
                    405                      410                      415

Ala  Val  Lys  Val  His  Ser  Phe  Pro  Thr  Leu  Lys  Phe  Phe  Pro  Ala  Ser
                    420                      425                      430

Ala  Asp  Arg  Thr  Val  Ile  Asp  Tyr  Asn  Gly  Glu  Arg  Thr  Leu  Asp  Gly
               435                      440                      445

Phe  Lys  Lys  Phe  Leu  Glu  Ser  Gly  Gly  Gln  Asp  Gly  Ala  Gly  Asp  Asp
          450                      455                      460

Asp  Asp  Leu  Glu  Asp  Leu  Glu  Glu  Ala  Glu  Glu  Pro  Asp  Met  Glu  Glu
465                      470                      475                           480

Asp  Asp  Asp  Gln  Lys  Ala  Val  Lys  Asp  Glu  Leu
                    485                      490
```

( 2 ) INFORMATION FOR SEQ ID NO:4:

( i ) SEQUENCE CHARACTERISTICS:
        ( A ) LENGTH: 96
        ( B ) TYPE: nucleic acid
        ( C ) STRANDEDNESS: double
        ( D ) TOPOLOGY: linear ( i i ) MOLECULE TYPE: Other nucleic acid ( x i ) SEQUENCE DESCRIPTION: SEQ ID NO:4:

```
ATG  AAG  TGG  GTT  ACC  TTC  ATC  TCT  TTG  TTG  TTC  TTG  TTC  TCT  TCT  GCT    48
Met  Lys  Trp  Val  Thr  Phe  Ile  Ser  Leu  Leu  Phe  Leu  Phe  Ser  Ser  Ala
 1                        5                        10                       15

TAC  TCT  AGA  GGT  GTT  TTC  AGA  AGG  GGC  GCC  CCC  GAG  GAG  GAG  GAC  CAC    96
Tyr  Ser  Arg  Gly  Val  Phe  Arg  Arg  Gly  Ala  Pro  Glu  Glu  Glu  Asp  His
               20                        25                       30
```

( 2 ) INFORMATION FOR SEQ ID NO:5:

( i ) SEQUENCE CHARACTERISTICS:
        ( A ) LENGTH: 4
        ( B ) TYPE: amino acid
        ( D ) TOPOLOGY: linear ( i i ) MOLECULE TYPE:
        ( A ) DESCRIPTION: peptide ( v ) FRAGMENT TYPE: C-terminal fragment ( i x ) FEATURE:
        ( A ) NAME/KEY: ER retension signal
        ( B ) LOCATION: C-terminus
        ( C ) IDENTIFICATION METHOD: ER retension of proteins having this signal
        ( D ) OTHER INFORMATION: located at the C-terminus of rat PDI ( x ) PUBLICATION INFORMATION:
        ( A ) AUTHORS: Edman, Jeffrey C., Ellis, Leland, Blacher,
                Russell W., Roth, Richard A. and Rutter,
                William J.
        ( B ) TITLE: Sequence of protein disulphide isomerase and
              implications of its relationship to thioredoxin
        ( C ) JOURNAL: Nature
        ( D ) VOLUME: 317
        ( F ) PAGES: 267-270
        ( G ) DATE: 19-Sep-1985
        ( H ) RELEVANT RESIDUES IN SEQ ID NO:2: FROM 486 to 489

( x i ) SEQUENCE DESCRIPTION: SEQ ID NO:5:

Lys  Asp  Glu  Leu ( 2 ) INFORMATION FOR SEQ ID NO:6:

( i ) SEQUENCE CHARACTERISTICS:
  ( A ) LENGTH: 4
  ( B ) TYPE: amino acid
  ( D ) TOPOLOGY: linear ( i i ) MOLECULE TYPE:
  ( A ) DESCRIPTION: peptide ( v ) FRAGMENT TYPE: C-terminal fragment ( i x ) FEATURE:
  ( A ) NAME/KEY: ER retention signal
  ( B ) LOCATION: C-terminus
  ( C ) IDENTIFICATION METHOD: ER retention of proteins having this signal
  ( D ) OTHER INFORMATION: located at the C-terminus of yeast BiP/GRP78

( x ) PUBLICATION INFORMATION:
  ( A ) AUTHORS: Rose, Mark D., Misra, Leanne M. and Vogel, Joseph P.
  ( B ) TITLE: KAR2, a Karyogamy gene, is the yeast homolog of the mammalian BiP/GR78 gene
  ( C ) JOURNAL: Cell
  ( D ) VOLUME: 57
  ( F ) PAGES: 1211-1221
  ( G ) DATE: 30-Jun-1989
  ( H ) RELEVANT RESIDUES IN SEQ ID NO:2: FROM 679 TO 683

( x i ) SEQUENCE DESCRIPTION: SEQ ID NO:6:

His Asp Glu Leu ( 2 ) INFORMATION FOR SEQ ID NO:7:

( i ) SEQUENCE CHARACTERISTICS:
    ( A ) LENGTH: 4
    ( B ) TYPE: amino acid
    ( D ) TOPOLOGY: linear ( i i ) MOLECULE TYPE:
    ( A ) DESCRIPTION: peptide ( v ) FRAGMENT TYPE: C-terminal fragment ( i x ) FEATURE:
    ( A ) NAME/KEY: ER retention signal
    ( B ) LOCATION: C-terminus
    ( C ) IDENTIFICATION METHOD: ER retention of proteins having this signal
    ( D ) OTHER INFORMATION: located at the C-terminus of *Kluyveromyces lactis* BiP ( x ) PUBLICATION INFORMATION:
    ( A ) AUTHORS: Lewis, M. J. and Pelham, H. R. B.
    ( B ) TITLE: The sequence of the BiP gene from *Kluyveromyces lactis*
    ( C ) JOURNAL: Nucleic Acids Res.
    ( D ) VOLUME: 18
    ( F ) PAGES: 6438-6438
    ( G ) DATE: 1990
    ( H ) RELEVANT RESIDUES IN SEQ ID NO:2: FROM 676 TO 679

( x i ) SEQUENCE DESCRIPTION: SEQ ID NO:7:

Asp Asp Glu Leu ( 2 ) INFORMATION FOR SEQ ID NO:8:

( i ) SEQUENCE CHARACTERISTICS:
    ( A ) LENGTH: 4
    ( B ) TYPE: amino acid
    ( D ) TOPOLOGY: linear ( i i ) MOLECULE TYPE:
    ( A ) DESCRIPTION: peptide ( v ) FRAGMENT TYPE: C-terminal fragment ( i x ) FEATURE:
            ( A ) NAME/KEY: ER retention signal
            ( B ) LOCATION: C-terminus
            ( C ) IDENTIFICATION METHOD: ER retention of proteins having
                                                                    this signal
            ( D ) OTHER INFORMATION: located at the C-terminus of
                                                        *Schizosaccharomyces pombe* BiP ( x ) PUBLICATION INFORMATION:
            ( A ) AUTHORS: Pidoux, A. L. and Armstrong, J.
            ( B ) TITLE: Analysis of the BiP gene and identification
                            of an ER retention signal in
                            *Schizosaccharomyces pombe*
            ( C ) JOURNAL: EMBO J
            ( D ) VOLUME: 11
            ( F ) PAGES: 1583-1591
            ( G ) DATE: 1992
            ( H ) RELEVANT RESIDUES IN SEQ ID NO:2: FROM 660 TO 663

( x i ) SEQUENCE DESCRIPTION: SEQ ID NO:8:

Ala Asp Glu Leu ( 2 ) INFORMATION FOR SEQ ID NO:9:

( i ) SEQUENCE CHARACTERISTICS:
            ( A ) LENGTH: 4
            ( B ) TYPE: amino acid
            ( D ) TOPOLOGY: linear ( i i ) MOLECULE TYPE:
            ( A ) DESCRIPTION: peptide ( v ) FRAGMENT TYPE: C-terminal fragment ( i x ) FEATURE:
            ( A ) NAME/KEY: ER retention signal
            ( B ) LOCATION: C-terminus
            ( C ) IDENTIFICATION METHOD: ER retention of proteins having
                                                                    this signal
            ( D ) OTHER INFORMATION: located at the C-terminus of
                                                        *Plasmodium falciparum* GRP78

( x ) PUBLICATION INFORMATION:
            ( A ) AUTHORS: Kumar, N., Syin, C., Carter, R., Quakyi, I.
                            and Miller, L. H.
            ( B ) TITLE: *Plasmodium falciparum* gene encoding a protein
                            similar to the 78-kDa rar glucose-regulated
                            stress protein
            ( C ) JOURNAL: Proc. Natl. Acad, Sci. U.S.A.
            ( D ) VOLUME: 85
            ( F ) PAGES: 6277-6281
            ( G ) DATE: 1988
            ( H ) RELEVANT RESIDUES IN SEQ ID NO:2: FROM 276 TO 279

( x i ) SEQUENCE DESCRIPTION: SEQ ID NO:9:

Ser Asp Glu Leu ( 2 ) INFORMATION FOR SEQ ID NO:10:

( i ) SEQUENCE CHARACTERISTICS:
            ( A ) LENGTH: 4
            ( B ) TYPE: amino acid
            ( D ) TOPOLOGY: linear ( i i ) MOLECULE TYPE:
            ( A ) DESCRIPTION: peptide ( v ) FRAGMENT TYPE: C-terminal fragment ( i x ) FEATURE:
            ( A ) NAME/KEY: ER retention signal
            ( B ) LOCATION: C-terminus
            ( C ) IDENTIFICATION METHOD: ER retention of proteins having
                                                                    this signal
            ( D ) OTHER INFORMATION: located at the C-terminus of rat collagen-binding protein ( x ) PUBLICATION INFORMATION:
  ( A ) AUTHORS: Clarke, E. P., Gates, G. A., Ball, E. H.
      and Sanwal, B. D.
  ( B ) TITLE: A collagen-binding protein in the endoplasmic
      reticulum of myoblasts exhibits relationship with
      serine protease inhibitory rat heat-shock
      collagen-binding protein (gp46)
  ( C ) JOURNAL: J. Biol. Chem.
  ( D ) VOLUME: 266
  ( F ) PAGES: 17230-17235
  ( G ) DATE: 1991
  ( H ) RELEVANT RESIDUES IN SEQ ID NO:2: FROM 397 TO 400

( x i ) SEQUENCE DESCRIPTION: SEQ ID NO:10:

Arg  Asp  Glu  Leu ( 2 ) INFORMATION FOR SEQ ID NO:11:

( i ) SEQUENCE CHARACTERISTICS:
    ( A ) LENGTH: 4
    ( B ) TYPE: amino acid
    ( D ) TOPOLOGY: linear ( i i ) MOLECULE TYPE:
    ( A ) DESCRIPTION: peptide ( v ) FRAGMENT TYPE: C-terminal fragment ( i x ) FEATURE:
    ( A ) NAME/KEY: ER retention signal
    ( B ) LOCATION: C-terminus
    ( C ) IDENTIFICATION METHOD: ER retention of proteins
        having this signal
    ( D ) OTHER INFORMATION: located at the C-terminus of mouse
        protein disulfide isomerase-related
        protein (ERp72)

( x ) PUBLICATION INFORMATION:
    ( A ) AUTHORS: Mazzarella, R. A., Srinivasan, M., HaugeJorden
        and S. M. and Green, M.
    ( B ) TITLE: ERp72, an abundant luminal endoplasmic reticulum
        protein, contains three copies of the active site
        sequences of protein disulfide isomerase
    ( C ) JOURNAL: J. Biol. Chem.
    ( D ) VOLUME: 265
    ( F ) PAGES: 1094-1101
    ( G ) DATE: 1990
    ( H ) RELEVANT RESIDUES IN SEQ ID NO:2: FROM 617 TO 620

( x i ) SEQUENCE DESCRIPTION: SEQ ID NO:11:

Lys  Glu  Glu  Leu ( 2 ) INFORMATION FOR SEQ ID NO:12:

( i ) SEQUENCE CHARACTERISTICS:
    ( A ) LENGTH: 4
    ( B ) TYPE: amino acid
    ( D ) TOPOLOGY: linear ( i i ) MOLECULE TYPE:
    ( A ) DESCRIPTION: peptide ( v ) FRAGMENT TYPE: C-terminal fragment ( i x ) FEATURE:
    ( A ) NAME/KEY: ER retention signal
    ( B ) LOCATION: C-terminus
    ( C ) IDENTIFICATION METHOD: ER retention of proteins having
        this signal
    ( D ) OTHER INFORMATION: located at the C-terminus of rat
        form- I phosphoinositide-specific
        phospholipase C ( x ) PUBLICATION INFORMATION:

(A) AUTHORS: Bennet, C. F., Balcarek, J. M., Varrichio, A.
and Crooke, S. T.
(B) TITLE: Molecular cloning and complete amino-acid
sequence of form-I phosphoinositide-specific
phospholipase C
(C) JOURNAL: Nature
(D) VOLUME: 334
(F) PAGES: 268-270
(G) DATE: 21-Jul-1988
(H) RELEVANT RESIDUES IN SEQ ID NO:2: FROM 501 TO 504

(xi) SEQUENCE DESCRIPTION: SEQ ID NO:12:

Gln Glu Asp Leu (2) INFORMATION FOR SEQ ID NO:13:

(i) SEQUENCE CHARACTERISTICS:
(A) LENGTH: 4
(B) TYPE: amino acid
(D) TOPOLOGY: linear (ii) MOLECULE TYPE:
(A) DESCRIPTION: peptide (v) FRAGMENT TYPE: C-terminal fragment (ix) FEATURE:
(A) NAME/KEY: ER retention signal
(B) LOCATION: C-terminus
(C) IDENTIFICATION METHOD: ER retention of proteins having
this signal
(D) OTHER INFORMATION: located at the C-terminus of rabbit
carboxy-esterase I (x) PUBLICATION INFORMATION:
(A) AUTHORS: Korza, G. and Ozols, J.
(B) TITLE: Complete covalent structure of 60-kDa esterase
isolated from 2,3,7,8- tetrachlorodibenzo-
p-dioxin-induced rabbit liver microsomes
(C) JOURNAL: J. Biol. Chem.
(D) VOLUME: 263
(F) PAGES: 3486-3495
(G) DATE: 1988
(H) RELEVANT RESIDUES IN SEQ ID NO:2: FROM 536 TO 539

(xi) SEQUENCE DESCRIPTION: SEQ ID NO:13:

His Ile Glu Leu (2) INFORMATION FOR SEQ ID NO:14:

(i) SEQUENCE CHARACTERISTICS:
(A) LENGTH: 4
(B) TYPE: amino acid
(D) TOPOLOGY: linear (ii) MOLECULE TYPE:
(A) DESCRIPTION: peptide (v) FRAGMENT TYPE: C-terminal fragment (ix) FEATURE:
(A) NAME/KEY: ER retention signal
(B) LOCATION: C-terminus
(C) IDENTIFICATION METHOD: ER retention of proteins having
this signal
(D) OTHER INFORMATION: located at the c-terminus of rabbit
carboxy-esterase II (x) PUBLICATION INFORMATION:
(A) AUTHORS: Ozols, J.
(B) TITLE: Covalent structure relationships in two
microsomal luminal carboxyesterases
(C) JOURNAL: J. Cell Biol.
(D) VOLUME: 107
(F) PAGES: 772a
(G) DATE: 1988

( H ) RELEVANT RESIDUES IN SEQ ID NO:2: FROM 529 TO 532

( x i ) SEQUENCE DESCRIPTION: SEQ ID NO:14:

His Thr Glu Leu ( 2 ) INFORMATION FOR SEQ ID NO:15:

( i ) SEQUENCE CHARACTERISTICS:
                ( A ) LENGTH: 4
                ( B ) TYPE: amino acid
                ( D ) TOPOLOGY: linear ( i i ) MOLECULE TYPE:
                ( A ) DESCRIPTION: peptide ( v ) FRAGMENT TYPE: C-terminal fragment ( i x ) FEATURE:
                ( A ) NAME/KEY: ER retention signal
                ( B ) LOCATION: C-terminus
                ( C ) IDENTIFICATION METHOD: ER retention of proteins having
                                                                        this signal
                ( D ) OTHER INFORMATION: located at the C-terminus of
                                                        trypanosoma bloodstream-specific prote
                                                        2 precursor ( x ) PUBLICATION INFORMATION:
                ( A ) AUTHORS: Hsu, M. P , Muhich, M. L. and Boothroyd,
                                                        J. C.
                ( B ) TITLE: A developmentally regulated gene of trypanosomes
                                                        encodes a homologue of rat protein-disulfide
                                                        isomerase and phosphoinisitol-phospholipase C
                ( C ) JOURNAL: Biochemistry
                ( D ) VOLUME: 28
                ( F ) PAGES: 6440-6446
                ( G ) DATE: 1989
                ( H ) RELEVANT RESIDUES IN SEQ ID NO:2: FROM 494 TO 497

( x i ) SEQUENCE DESCRIPTION: SEQ ID NO:15:

Lys Gln Asp Leu ( 2 ) INFORMATION FOR SEQ ID NO:16:

( i ) SEQUENCE CHARACTERISTICS:
                ( A ) LENGTH: 28
                ( B ) TYPE: nucleic acid
                ( C ) STRANDEDNESS: single
                ( D ) TOPOLOGY: linear ( i i ) MOLECULE TYPE: synthetic primer ( i i i ) HYPOTHETICAL: yes ( i v ) ANTI-SENSE: no ( v i ) ORIGINAL SOURCE:
                ( A ) ORGANISM: Sacharomyces cerevisiae
                ( B ) INDIVIDUAL ISOLATE: S288C
                ( C ) CELL TYPE: unicellular organism ( v i i ) IMMEDIATE SOURCE:
                ( A ) LIBRARY: genomic
                ( B ) CLONE: pYERD2

( x ) PUBLICATION INFORMATION:
                ( A ) AUTHORS: Jan C. Semenza, Kevin G. Hardwick, Neta Dean,
                                                        and Hugh R.B. Pelham
                ( B ) TITLE: ERD2, a Yeast Gene Required for the
                                                        Receptor-Mediated Retrieval of Luminal ER
                                                        Proteins from the Secretory Pathway
                ( C ) JOURNAL: Cell
                ( D ) VOLUME: 61
                ( F ) PAGES: 1349-1357
                ( G ) DATE: 29-Jun-1990
                ( K ) RELEVANT RESIDUES IN SEQ ID NO:1: FROM 1222 TO 1242

( x i ) SEQUENCE DESCRIPTION: SEQ ID NO:16:

TTTTTCTCGA GTAAGCAATG AATCCGTT            28

( 2 ) INFORMATION FOR SEQ ID NO:17:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) MOLECULE TYPE: synthetic primer ( i i i ) HYPOTHETICAL: yes ( i v ) ANTI-SENSE: yes ( v i ) ORIGINAL SOURCE:
        ( A ) ORGANISM: Sacharomyces cerevisiae
        ( B ) INDIVIDUAL ISOLATE: S288C
        ( C ) CELL TYPE: unicellular organism ( v i i ) IMMEDIATE SOURCE:
        ( A ) LIBRARY: genomic
        ( B ) CLONE: pYERD2

( x ) PUBLICATION INFORMATION:
        ( A ) AUTHORS: Jan C. Semenza, Kevin G. Hardwick, Neta Dean,
                and Hugh R.B. Pelham
        ( B ) TITLE: ERD2, a Yeast Gene Required for the Receptor-
                Mediated Retrieval of Luminal ER Proteins from
                the Secretory Pathway
        ( C ) JOURNAL: Cell
        ( D ) VOLUME: 61
        ( F ) PAGES: 1349-1357
        ( G ) DATE: 29-Jun-1990
        ( K ) RELEVANT RESIDUES IN SEQ ID NO:1: FROM 2000 TO 2017

( x i ) SEQUENCE DESCRIPTION: SEQ ID NO:17:

AAAAAGGATC CTGCGAACAC TATTTAAA            28

( 2 ) INFORMATION FOR SEQ ID NO:18:

( i ) SEQUENCE CHARACTERISTICS:
        ( A ) LENGTH: 40
        ( B ) TYPE: nucleic acid
        ( C ) STRANDEDNESS: single
        ( D ) TOPOLOGY: linear ( i i ) MOLECULE TYPE: synthetic probe ( i i i ) HYPOTHETICAL: yes ( i v ) ANTI-SENSE: yes ( v i ) ORIGINAL SOURCE:
        ( A ) ORGANISM: human
        ( B ) INDIVIDUAL ISOLATE:
        ( C ) CELL TYPE: multicellular organism ( v i i ) IMMEDIATE SOURCE:
        ( A ) LIBRARY: cDNA
        ( B ) CLONE: pHPDI16 and pHPDIp4

( x ) PUBLICATION INFORMATION:
        ( A ) AUTHORS: Pihalajaniemi, T., Helaakoski, T., Tasanen, K.,
                Myllyla, R., Huhtala, M.-L., Koivu, J. and
                Kivirikko, K.I.
        ( B ) TITLE: Molecular cloning of the β-subunit of human
                prolyl 4-hydroxylase. This subunit and protein
                disulphide isomerase are products of the same
                gene
        ( C ) JOURNAL: EMBO J
        ( D ) VOLUME: 6
        ( E ) ISSUE:3
        ( F ) PAGES: 643-649

(G) DATE: 1987
(K) RELEVANT RESIDUES IN SEQ ID NO:1: FROM 243 TO 282

(xi) SEQUENCE DESCRIPTION: SEQ ID NO:18:

TGGCGTCCAC CTTGGCCAAC CTGATCTCGG AACCTTCTGC 40

(2) INFORMATION FOR SEQ ID NO:19:

(i) SEQUENCE CHARACTERISTICS:
 (A) LENGTH: 10
 (B) TYPE: nucleic acid
 (C) STRANDEDNESS: single
 (D) TOPOLOGY: linear (ii) MOLECULE TYPE: synthetic gene fragment (iii) HYPOTHETICAL: yes (xi) SEQUENCE DESCRIPTION: SEQ ID NO:19:

AATTCTCGAG 10

(2) INFORMATION FOR SEQ ID NO:20:

(i) SEQUENCE CHARACTERISTICS:
 (A) LENGTH: 10
 (B) TYPE: nucleic acid
 (C) STRANDEDNESS: single
 (D) TOPOLOGY: linear (ii) MOLECULE TYPE: synthetic gene fragment (iii) HYPOTHETICAL: yes (xi) SEQUENCE DESCRIPTION: SEQ ID NO:20:

GAGCTCTTAA 10

(2) INFORMATION FOR SEQ ID NO:21:

(i) SEQUENCE CHARACTERISTICS:
 (A) LENGTH: 42
 (B) TYPE: nucleic acid (DNA fragment encoding a part of
  the prepropeptide of humuan serum albumin and
  designed using the yeast preferential codons)
 (C) STRANDEDNESS: single
 (D) TOPOLOGY: linear (ii) MOLECULE TYPE: synthetic gene fragment (iii) HYPOTHETICAL: yes (iv) ANTI-SENSE: no (vi) ORIGINAL SOURCE:
 (A) ORGANISM: human
 (B) INDIVIDUAL ISOLATE:
 (C) CELL TYPE: multicellular organism (vii) IMMEDIATE SOURCE:
 (A) LIBRARY:
 (B) CLONE:

(x) PUBLICATION INFORMATION:
 (A) AUTHORS: Lawn, R. M., Adelman, J., Bock, S. C., Franke,
  A. E., Houck, C. M., Najarian, R. C., Seeburg,
  P. H. and Wion, K. L.
 (B) TITLE: The sequence of human serum albumin cDNA and its
  expression in E.coli
 (C) JOURNAL: Nucleic Acids Res.
 (D) VOLUME: 9
 (F) PAGES: 6103-6114
 (G) DATE: 1981
 (K) RELEVANT RESIDUES IN SEQ ID NO:1: FROM 76 TO 107

(xi) SEQUENCE DESCRIPTION: SEQ ID NO:21:

TCGAGAATTC ATGAAGTGGG TTACCTTCAT CTCTTTGTTG TT    42

( 2 ) INFORMATION FOR SEQ ID NO:22:

( i ) SEQUENCE CHARACTERISTICS:
        ( A ) LENGTH: 44
        ( B ) TYPE: nucleic acid (DNA fragment encoding a part of the prepropeptide of human serum albumin with a linker and designed using the yeast preferential codons)
        ( C ) STRANDEDNESS: single
        ( D ) TOPOLOGY: linear ( i i ) MOLECULE TYPE: synthetic gene frgment ( i i i ) HYPOTHETICAL: yes ( i v ) ANTI-SENSE: yes ( v i ) ORIGINAL SOURCE:
        ( A ) ORGANISM: human
        ( B ) INDIVIDUAL ISOLATE:
        ( C ) CELL TYPE: multicellular organism ( v i i ) IMMEDIATE SOURCE:
        ( A ) LIBRARY:
        ( B ) CLONE:

( x ) PUBLICATION INFORMATION:
        ( A ) AUTHORS: Lawn, R. M., Adelman, J., Bock, S. C., Franke, A. E., Houck, C. M., Najarian, R. C., Seeburg, P. H. and Wion, K. L.
        ( B ) TITLE: The sequence of human serum albumin cDNA and its expression in E.coli
        ( C ) JOURNAL: Nucleic Acids Res.
        ( D ) VOLUME: 9
        ( F ) PAGES: 6103-6114
        ( G ) DATE: 1981
        ( K ) RELEVANT RESIDUES IN SEQ ID NO:1: FROM 76 TO 107

( x i ) SEQUENCE DESCRIPTION: SEQ ID NO:22:

AACAAGAACA ACAAAGAGAT GAAGGTAACC CACTTCATGA ATTC    44

( 2 ) INFORMATION FOR SEQ ID NO:23:

( i ) SEQUENCE CHARACTERISTICS:
        ( A ) LENGTH: 44
        ( B ) TYPE: nucleic acid (DNA fragment encoding a part of the prepropeptide of human serum albumin with a linker and designed using the yeast preferential codons)
        ( C ) STRANDEDNESS: single
        ( D ) TOPOLOGY: linear ( i i ) MOLECULE TYPE: synthetic gene fragment ( i i i ) HYPOTHETICAL: yes ( i v ) ANTI-SENSE: no ( v i ) ORIGINAL SOURCE:
        ( A ) ORGANISM: human
        ( B ) INDIVIDUAL ISOLATE:
        ( C ) CELL TYPE: multicellular organism ( v i i ) IMMEDIATE SOURCE:
        ( A ) LIBRARY:
        ( B ) CLONE:

( x ) PUBLICATION INFORMATION:
        ( A ) AUTHORS: Lawn, R. M., Adelman, J., Bock, S. C., Franke, A. E., Houck, C. M., Najarian, R. C., Seeburg, P. H. and Wion, K. L.
        ( B ) TITLE: The sequence of human serum albumin cDNA and its expression in E.coli
        ( C ) JOURNAL: Nucleic Acids Res.
        ( D ) VOLUME: 9
        ( F ) PAGES: 6103-6114

(G) DATE: 1981
(K) RELEVANT RESIDUES IN SEQ ID NO:1: FROM 108 TO 147

(xi) SEQUENCE DESCRIPTION: SEQ ID NO:23:

CTTGTTCTCT TCTGCTTACT CTAGAGGTGT TTTCAGAAGG CCTG    44

(2) INFORMATION FOR SEQ ID NO:24:

(i) SEQUENCE CHARACTERISTICS:
(A) LENGTH: 42
(B) TYPE: nucleic acid (DNA fragment encoding a part of the
prepropeptide of human serum albumin with a linker
and designed using the yeast preferential codons)
(C) STRANDEDNESS: single
(D) TOPOLOGY: linear (ii) MOLECULE TYPE: synthetic gene fragement (iii) HYPOTHETICAL: yes (iv) ANTI-SENSE: yes (vi) ORIGINAL SOURCE:
(A) ORGANISM: human
(B) INDIVIDUAL ISOLATE:
(C) CELL TYPE: multicellular organism (vii) IMMEDIATE SOURCE:
(A) LIBRARY:
(B) CLONE:

(x) PUBLICATION INFORMATION:
(A) AUTHORS: Lawn, R. M., Adelman, J., Bock, S. C., Franke,
A. E., Houck, C. M., Najarian, R. C., Seeburg,
P. H. and Wion, K. L.
(B) TITLE: The sequence of human serum albumin cDNA and its
expression in E.coli
(C) JOURNAL: Nucleic Acids Res.
(D) VOLUME: 9
(F) PAGES: 6103-6114
(G) DATE: 1981
(K) RELEVANT RESIDUES IN SEQ ID NO:1: FROM 108 TO 147

(xi) SEQUENCE DESCRIPTION: SEQ ID NO:24:

GATCCAGGCC TTCTGAAAAC ACCTCTAGAG TAAGCAGAAG AG    42